United States Patent
Vartak et al.

(10) Patent No.: US 11,007,256 B2
(45) Date of Patent: May 18, 2021

(54) SYNTHETIC LIPOPEPTIDE VACCINES AND IMMUNOTHERAPEUTICS

(71) Applicant: The University of Toledo, Toledo, OH (US)

(72) Inventors: Abhishek R. Vartak, Toledo, OH (US); Steven J. Sucheck, Toledo, OH (US); Katherine Ann Wall, Toledo, OH (US); Anthony Quinn, Toledo, OH (US); Marcia F. Mcinerney, Toledo, OH (US)

(73) Assignee: The University of Toledo, Toledo, OH (US)

( * ) Notice: Subject to any disclaimer, the term of this patent is extended or adjusted under 35 U.S.C. 154(b) by 69 days.

(21) Appl. No.: 16/333,704

(22) PCT Filed: Sep. 26, 2017

(86) PCT No.: PCT/US2017/053359
§ 371 (c)(1),
(2) Date: Mar. 15, 2019

(87) PCT Pub. No.: WO2018/058086
PCT Pub. Date: Mar. 29, 2018

(65) Prior Publication Data
US 2019/0231860 A1 Aug. 1, 2019

Related U.S. Application Data

(60) Provisional application No. 62/399,762, filed on Sep. 26, 2016.

(51) Int. Cl.
| | |
|---|---|
| *C07K 7/06* | (2006.01) |
| *A61K 39/00* | (2006.01) |
| *C07K 9/00* | (2006.01) |
| *A61K 47/69* | (2017.01) |
| *A61K 31/395* | (2006.01) |
| *A61P 3/10* | (2006.01) |
| *A61P 35/00* | (2006.01) |
| *A61K 47/26* | (2006.01) |
| *C07K 7/08* | (2006.01) |
| *C07K 16/30* | (2006.01) |
| *C07K 19/00* | (2006.01) |

(52) U.S. Cl.
CPC ...... *A61K 39/0011* (2013.01); *A61K 31/5545* (2017.08); *A61K 39/00117* (2018.08); *A61K 47/26* (2013.01); *A61K 47/6911* (2017.08); *A61P 3/10* (2018.01); *A61P 35/00* (2018.01); *C07K 7/06* (2013.01); *C07K 7/08* (2013.01); *C07K 9/00* (2013.01); *C07K 16/3092* (2013.01); *C07K 19/00* (2013.01); *A61K 2039/6018* (2013.01); *A61K 2039/6031* (2013.01)

(58) Field of Classification Search
CPC ........... A61K 39/0011; A61K 47/6911; A61K 31/5545; A61K 39/00117; A61K 47/26; A61K 2039/6018; A61K 2039/6031; C07K 9/00; C07K 7/08; C07K 16/3092; C07K 19/00; C07K 7/06; A61P 3/10; A61P 35/00
See application file for complete search history.

(56) References Cited

U.S. PATENT DOCUMENTS

| | | | |
|---|---|---|---|
| 2013/0330274 A1 | 12/2013 | Berr et al. | |
| 2015/0024037 A1* | 1/2015 | Sucheck | ............ A61K 39/0011 424/450 |
| 2015/0299290 A1 | 10/2015 | Boons et al. | |
| 2017/0095573 A1* | 4/2017 | Oh | .......................... A61P 11/00 |

FOREIGN PATENT DOCUMENTS

WO 2015187637 A1 12/2015

OTHER PUBLICATIONS

PCT International Search Report and Written Opinion, Application No. PCT/US2017/053359, dated Feb. 5, 2018.

\* cited by examiner

*Primary Examiner* — Sudhakar Katakam
(74) *Attorney, Agent, or Firm* — MacMillan, Sobanski & Todd, LLC

(57) ABSTRACT

Single molecules useful in vaccine compositions, and methods of making and using the same, are described.

20 Claims, 42 Drawing Sheets
Specification includes a Sequence Listing.

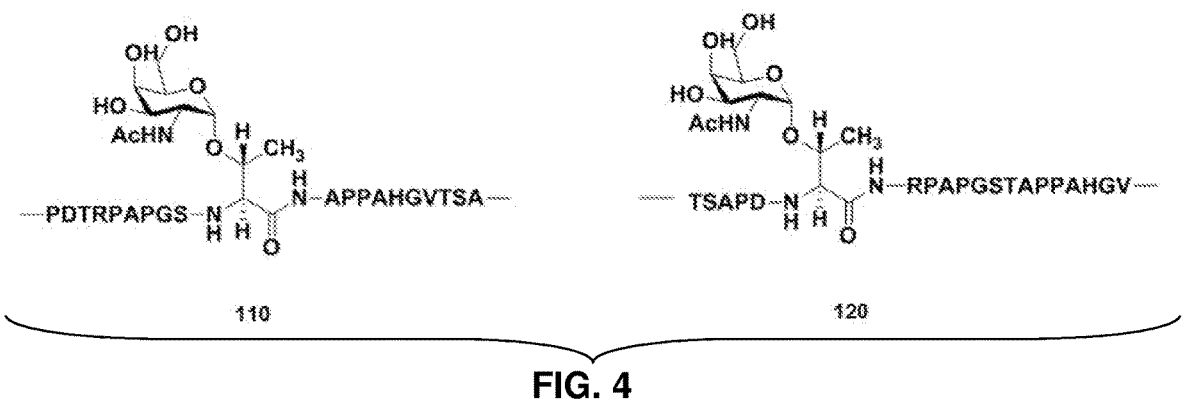
FIG. 4
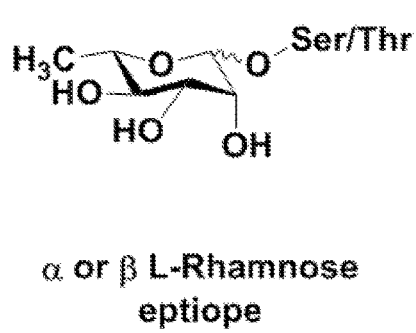
α or β L-Rhamnose eptiope
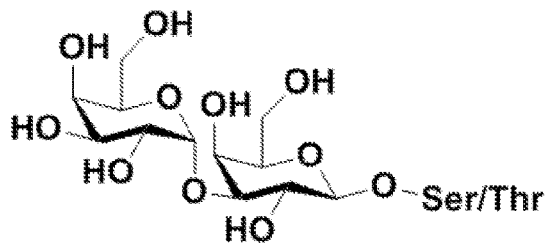
α-Gal disaccharide epitiope
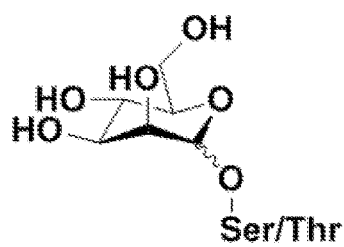
α or β -Mannose eptiope
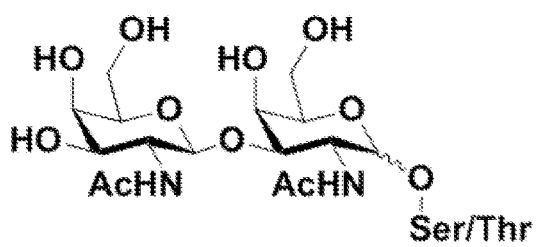
Forssman disaccharide epitiope
FIG. 5A

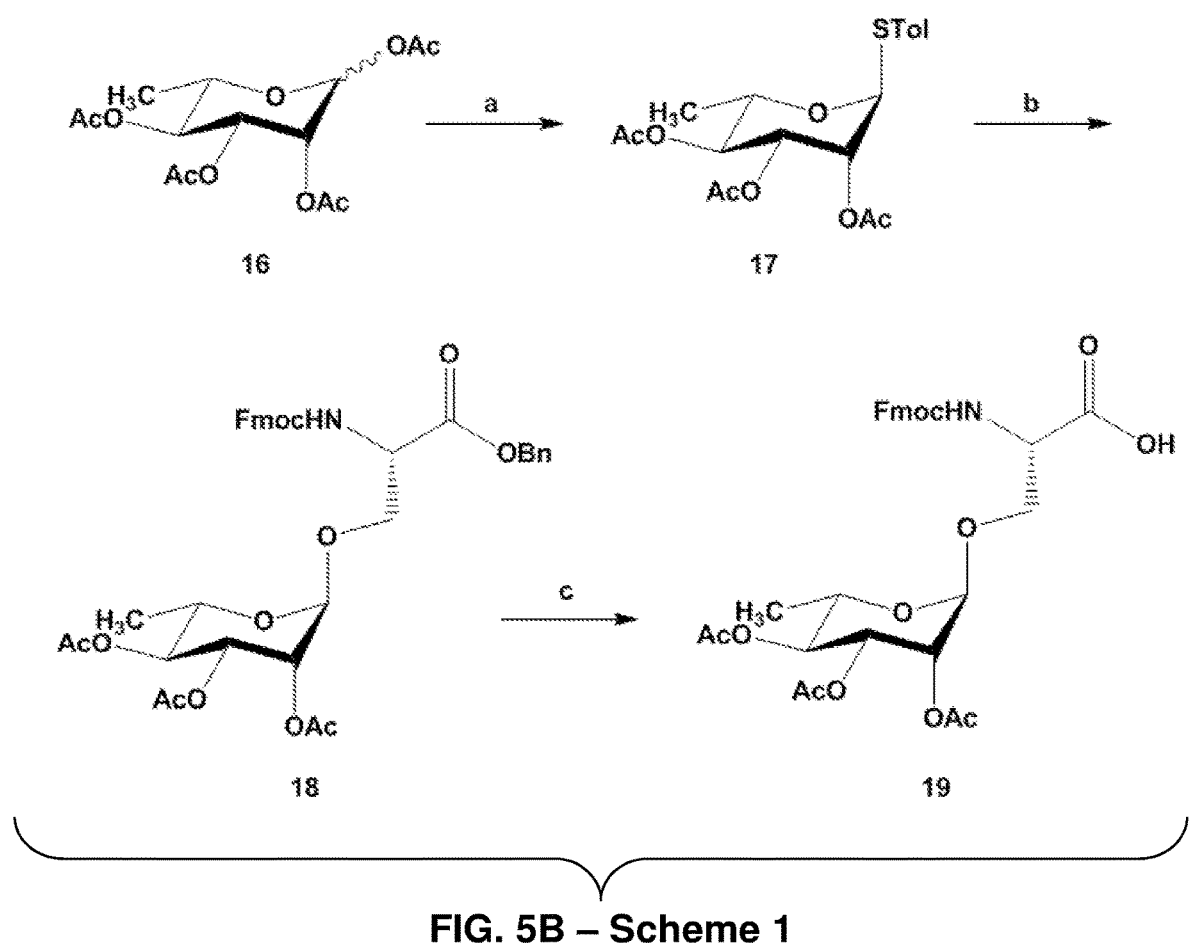
FIG. 5B – Scheme 1

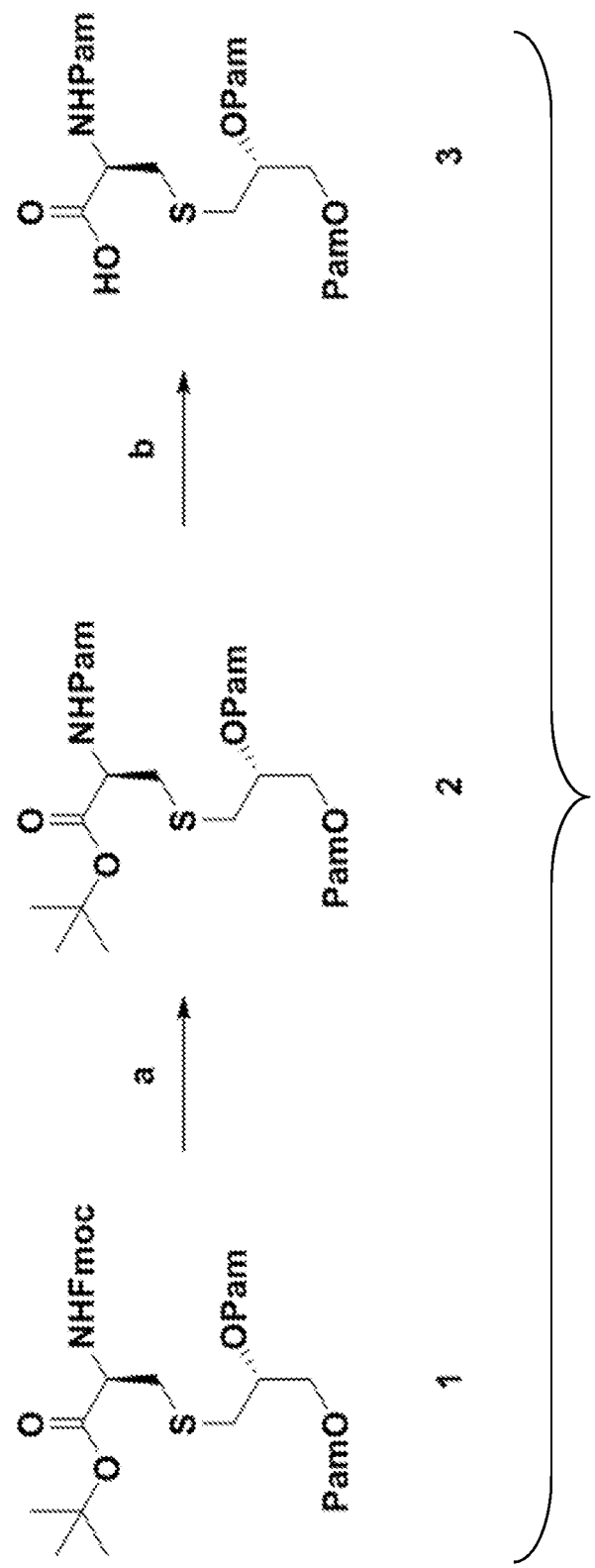
FIG. 6 – Scheme 2

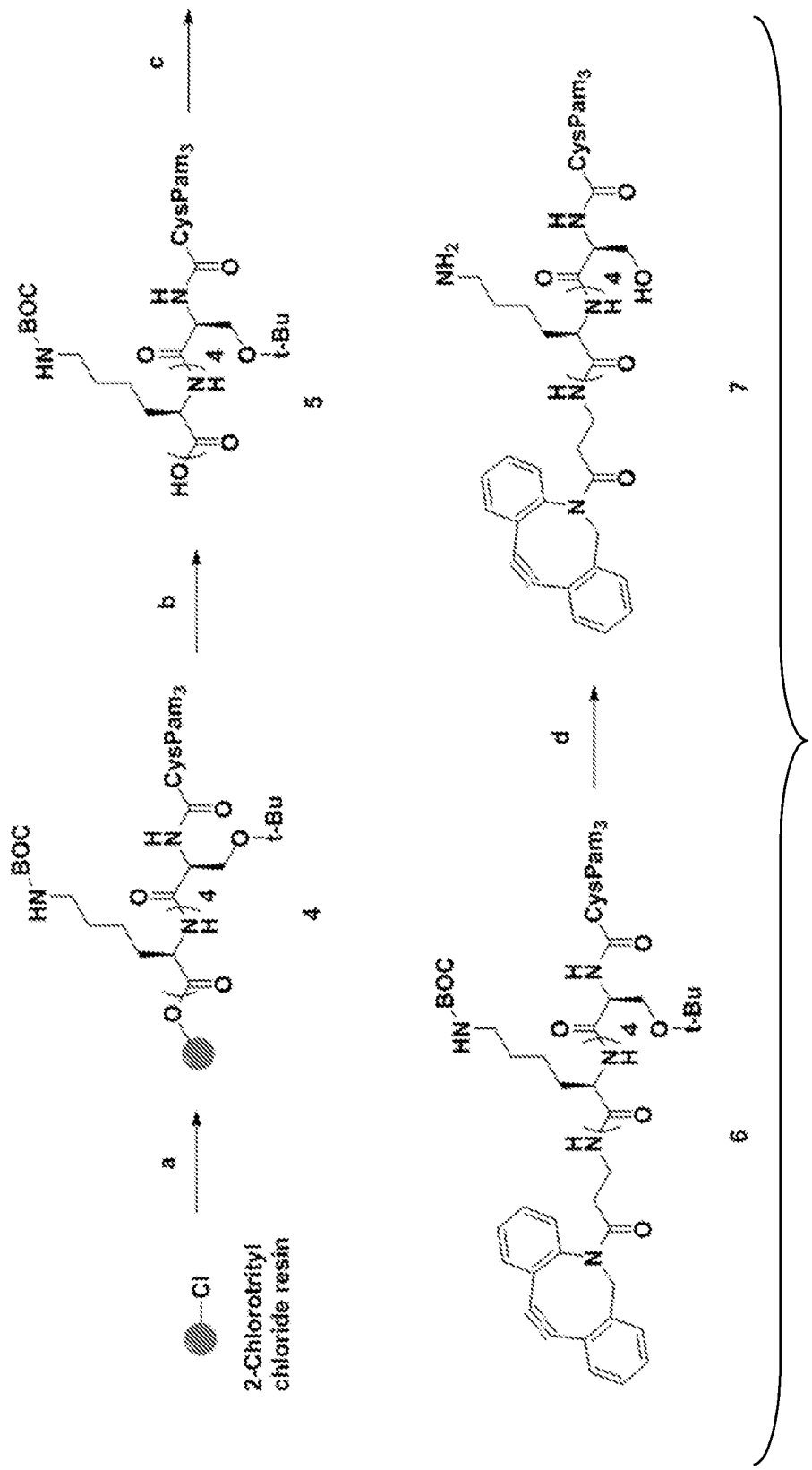
FIG. 7 – Scheme 3

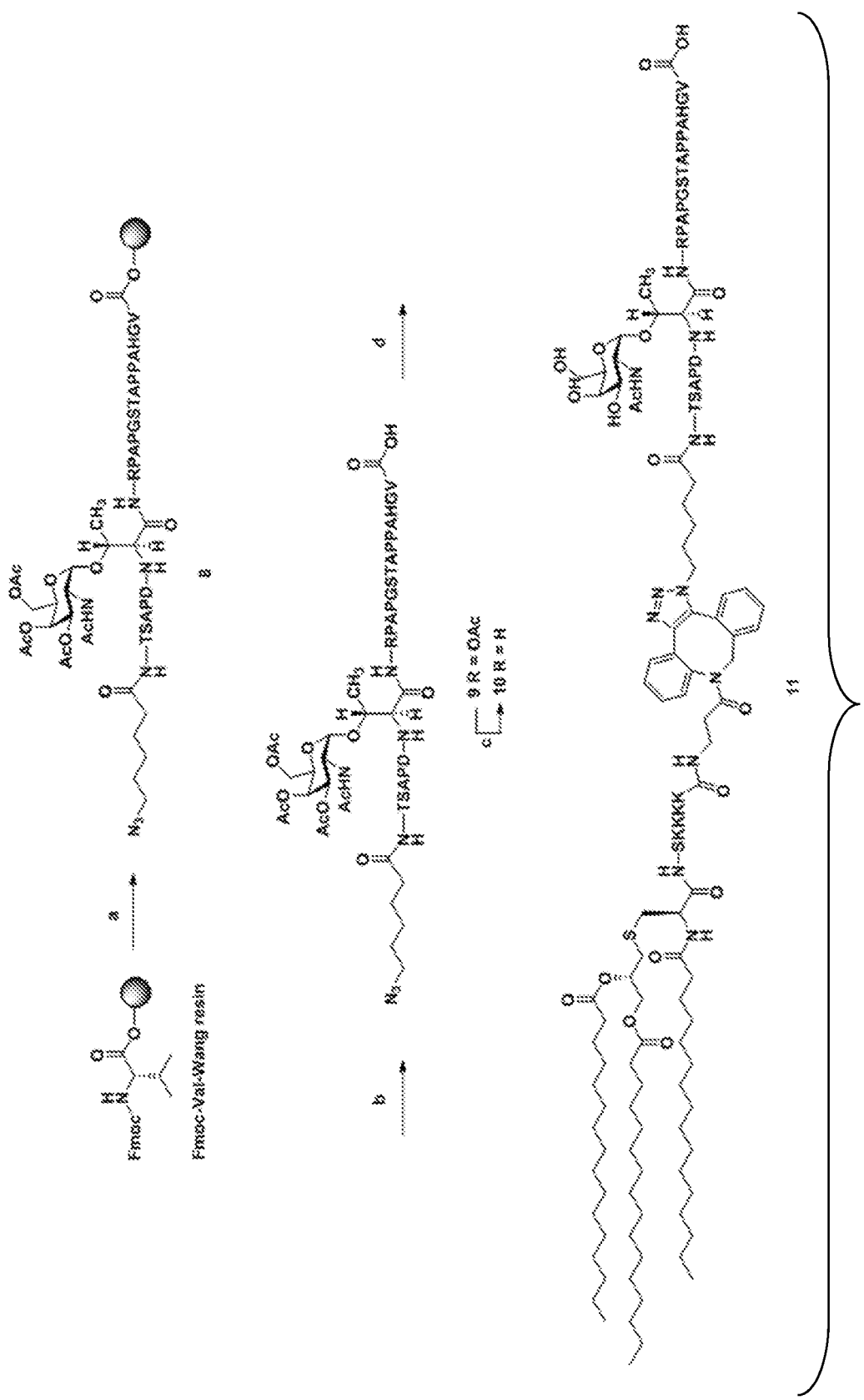
FIG. 8 – Scheme 4

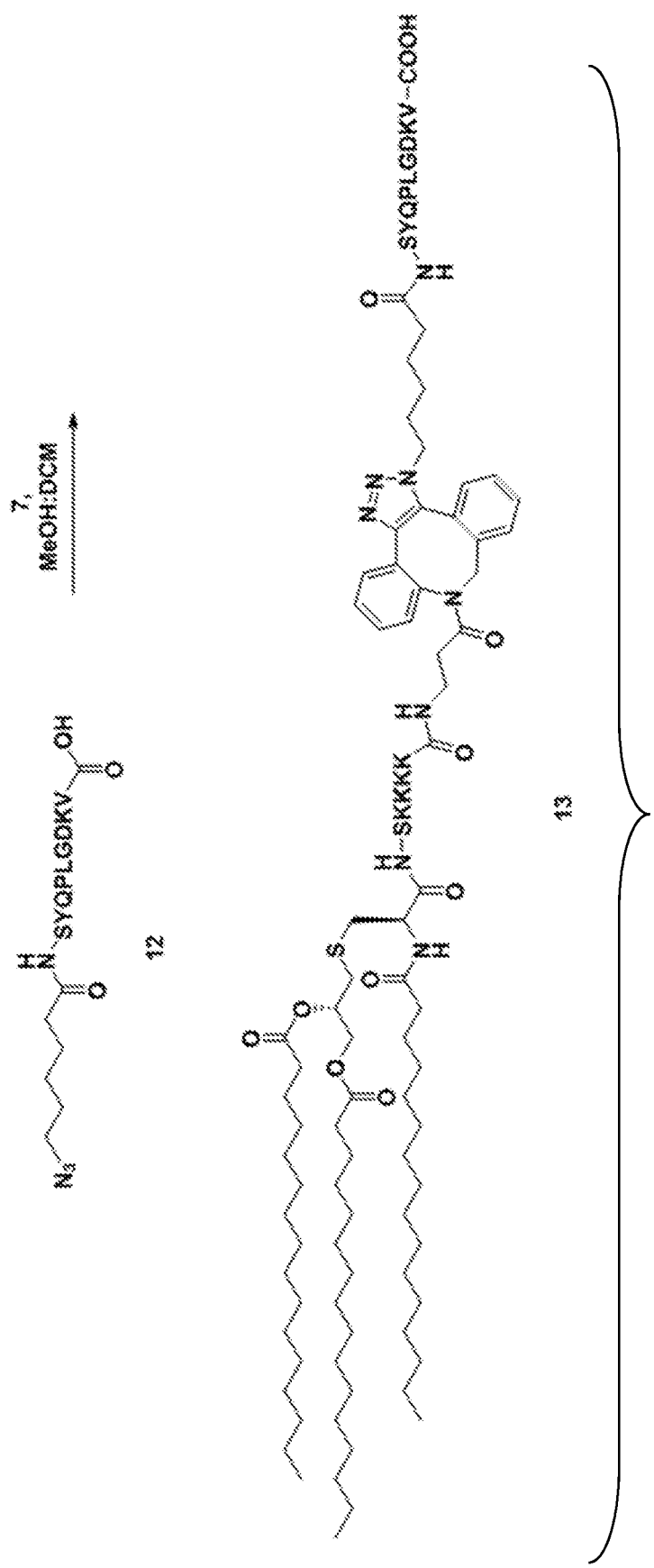
FIG. 9A – Scheme 5

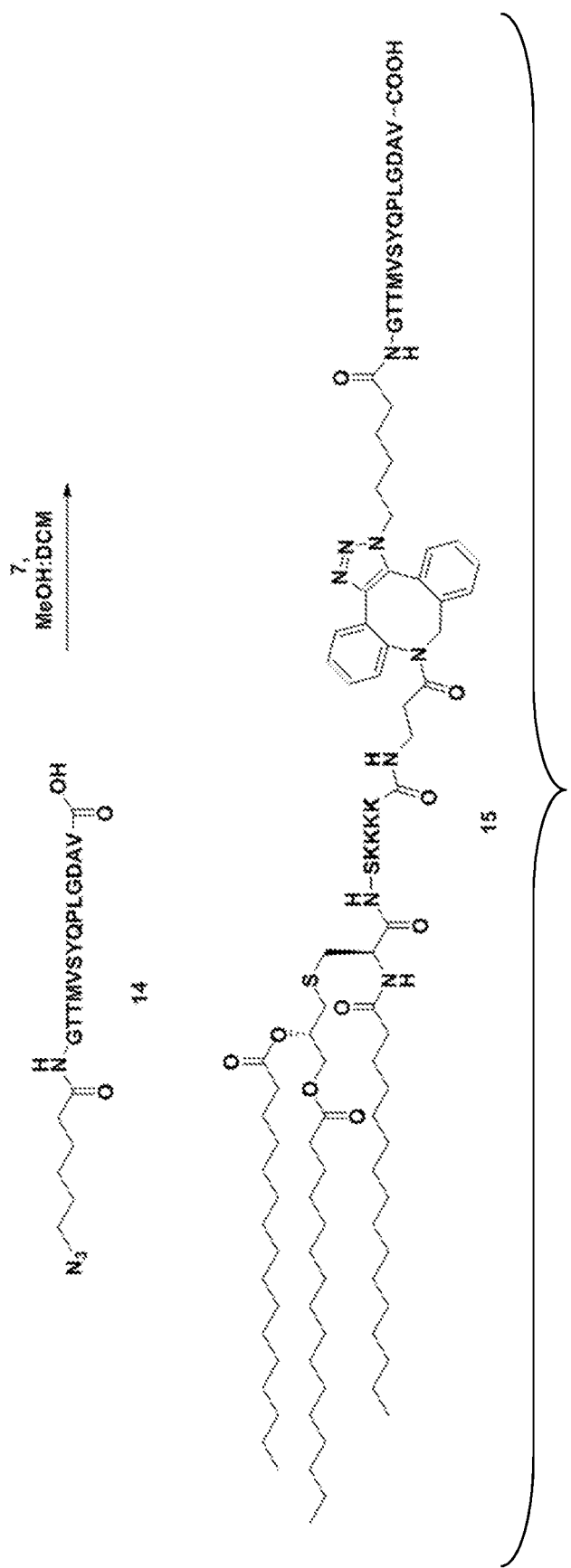
FIG. 9B – Scheme 6

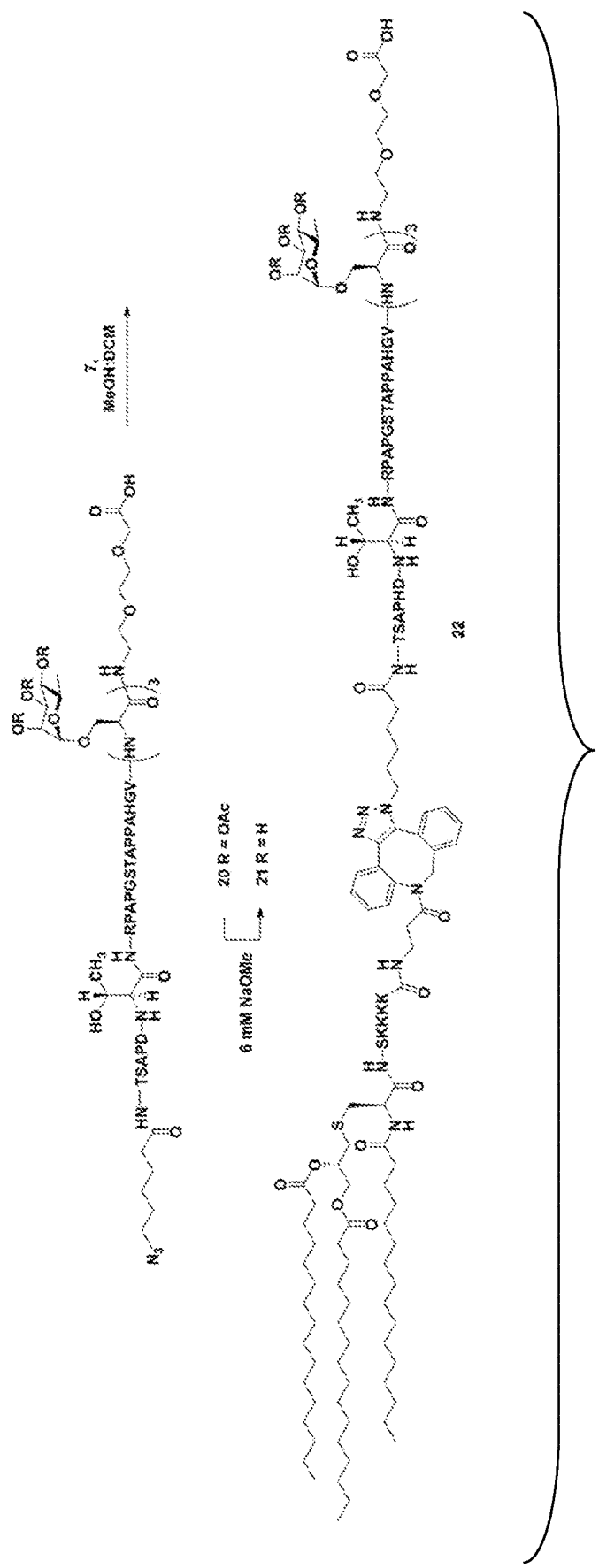
FIG. 9C – Scheme 7

SYNTHETIC LIPOPEPTIDE VACCINES AND IMMUNOTHERAPEUTICS

RELATED APPLICATIONS

This application claims priority to U.S. Provisional Application No. 62/399,762 filed under 35 U.S.C. § 111(b) on Sep. 26, 2016, the disclosure of which is incorporated herein by reference in its entirety for all purposes.

STATEMENT REGARDING FEDERALLY SPONSORED RESEARCH

This invention was made with government support under Grant Number 1R15GM094734-02 awarded by the National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on Sep. 21, 2017, is named 53-58515-D2017-06_SL.txt and is 5,734 bytes in size.

BACKGROUND OF THE INVENTION

The development of fully synthetic carbohydrate vaccines would be desirable. Protein conjugate vaccines have restrictions based on the innate immunogenicity of carrier proteins such as bovine serum albumin (BSA), and keyhole limpet hemocyanin (KLH), which can suppress the response against the associated carbohydrate antigen. A typical fully synthetic carbohydrate vaccine includes a carbohydrate antigen, T-helper cell epitope, and immunoadjuvant to boost the immune response. Modifications of this primary design have been investigated to achieve optimal immune response against the antigens.

The glycoconjugate patterns found on outer cell membrane of the normal epithelial cells and tumor epithelial cells are different. Thus, these aberrant carbohydrate components, also known as tumor associated carbohydrate antigens (TACAs), are promising as targets in cancer immunotherapy. TACAs, such as those depicted in FIGS. 1A-1B, can be used as carbohydrate epitopes in vaccine compositions. Different types of TACAs have been identified and classified according to their linkage to biomolecules. Lipid linked carbohydrates include GM2, GD2, GD3, Globo-H, and Lewis$^y$, while glycoprotein antigens include Tn-, Thomsen-Friedenreich (TF-), and sialylated Tn (STn).

As an example, TACAs found on mucin 1 (MUC-1) have been exploited. MUC-1 is a tramsmembrane protein found in almost all epithelial tissues with heavy glycosylation. But in the case of cancer cells, truncated glycosylation, as well as premature sialylation, makes MUC-1 an attractive target. The extracellular portion of the MUC-1 contains a variable number (between 20 to 120) of tandem repeats with potential O-glycosylation sites (i.e, serines and threonines). Because of the truncated glycosylation in cancer cells, peptide sequences from variable numbers of tandem repeats (VNTRs) get exposed to the immune system, which usually are completely covered in normal cells. TACAs with VNTR domain have shown promising results in breaking the immune system's self-tolerance against MUC-1. The PDTRP (SEQ ID NO: 15) peptide has been identified as an immunodominant domain among VNTRs.

Though TACAs are promising targets in cancer immunotherapy, carbohydrate antigens are weak immunogens and give a T-cell independent immune response when used alone. These antigens bind to B cell receptors (BCR) because of their polymeric nature activating B cells. Since T cells are not involved in the process, the priming of activated B cells for isotype switching via T helper cells never happens, which causes production of low affinity IgM antibodies. This and other challenges remain Thus, there is a need in the art for new vaccine compositions.

SUMMARY OF THE INVENTION

Provided is a composition comprising Formula I ("CysSK$_4$" disclosed as SEQ ID NO: 16):

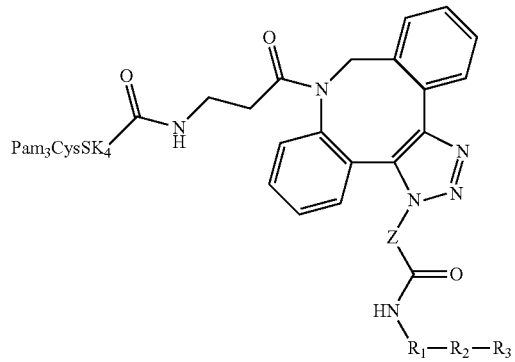

Formula I where the dashed line indicates that R$_3$ is optional; Z is a linker comprising a chain of C$_{1-n}$ alkyl or CH$_2$CH$_2$(OCH$_2$CH$_2$)$_n$—, where n is a positive integer; R$_1$ is a heterologous helper T-cell epitope consisting of a sequence of from 7 to 30 amino acids, or a bond when R$_2$ does not require an additional helper T-cell epitope; R$_2$ is either: (i) a B cell epitope in the form of a carbohydrate antigen derived from bacterial cells, viral envelopes, or other infected cell lines, or (ii) a B or T cell epitope consisting of from 7 to 30 amino acids, optionally including a TACA incorporated into the peptide sequence; R$_3$ is optional, but when present is either: (i) an O-linked xenoantigen attached to an amino acid via either an alpha or beta linkage, or (ii) a plurality of O-linked xenoantigens, where one of the plurality of O-linked xenoantigens is attached to an amino acid either via an alpha or beta linkage; provided, however, that R$_1$ and R$_2$ can together be a single epitope selected from (i) a B cell epitope in the form of a carbohydrate antigen derived from bacterial cells, viral envelopes, or other infected cell lines; and (ii) a B or T cell epitope consisting of from 7 to 30 amino acids, optionally including a TACA incorporated into the peptide sequence. Also provided are salts, stereoisomers, racemates, hydrates, solvates, and polymorphs of Formula I.

In certain embodiments, the composition is formulated in liposomes. In particular embodiments, the liposomes comprise 1,2-dipalmitoyl-sn-glycero-3-phosphocholine (DPPC), cholesterol, and 1,2-distearoyl-sn-glycero-3-phosphoethanolamine-N-[maleimide(polyethylene glycol)-2000] (DSPE-PEG-MAL). In particular embodiments, the liposomes comprise cholesterol-TEG-Rha, cholesterol, and 1,2-dipalmitoyl-sn-glycero-3-phosphocholine (DPPC). In particular embodiments, the liposomes are conjugated to an antibody. In particular embodiments, the antibody is anti-mouse F4/80.

In certain embodiments, Z is a $C_{1-5}$ alkyl chain.

In certain embodiments, the helper T-cell epitope of $R_1$ is selected from the group consisting of: QYIKANSKFIGITEL (SEQ ID NO: 1); KLFAVWKITYKDTG (SEQ ID NO: 2); YAFKYARHANVGRNAFELFL (SEQ ID NO: 3); ISQAVHAAHAEINEAGR (SEQ ID NO: 4); and A'KZVAAWTLKAA' (SEQ ID NO: 5), where A' is D-alanine, and Z is L-cyclohexylalanine.

In certain embodiments, $R_2$ comprises an antigen-amino acid construct selected from the group consisting of the following:

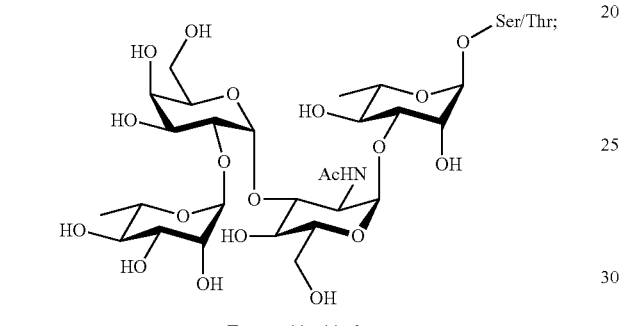

Tetrasachharide from *S. dysenteriae*

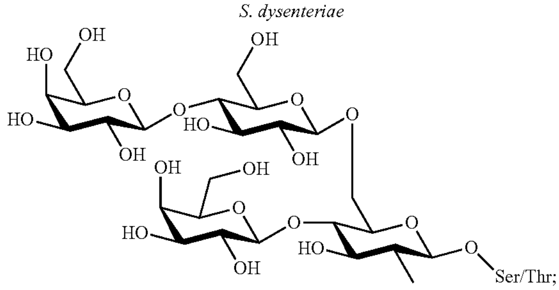

Tetrasachharide from *S. pneumonia* type 14

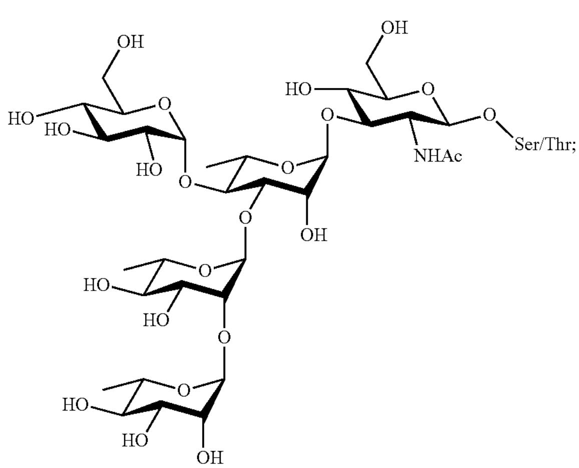

Polysachharide from *S. flexneri*

-continued 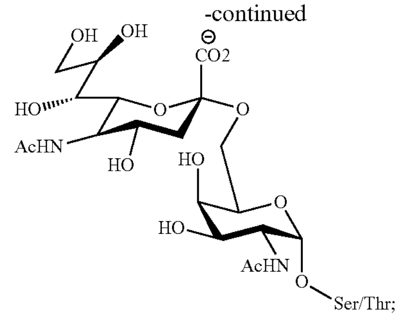 sTn

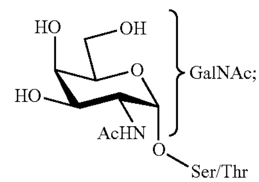

Tn

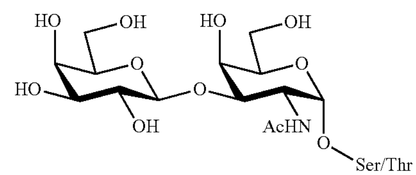

TF(T)

In certain embodiments, $R_2$ comprises a tumor glycopeptide sequence having an incorporated TACA, selected from the group consisting of the following (SEQ ID NOS 12 and 13 disclosed, respectively, in order of appearance):

(110)

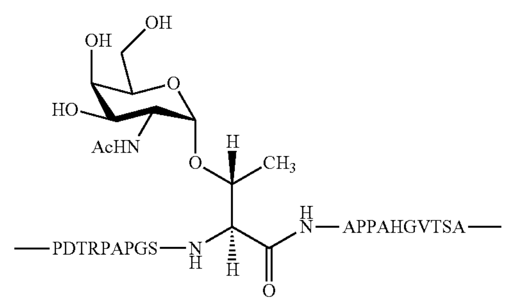

(120)

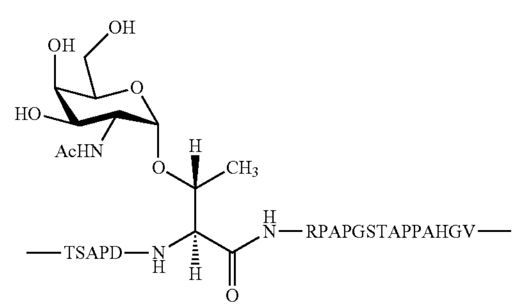

In certain embodiments, $R_2$ comprises a pathogenic or altered diabetic peptide sequence selected from the group consisting of: GTTMVSYQPLGDKV (SEQ ID NO: 6), SYQPLGDKV (SEQ ID NO: 7), SYQPLGDAV (SEQ ID NO: 8), GTTMVSYQPLGDAV (SEQ ID NO: 9), SYQPLGDKA (SEQ ID NO: 10), and GTTMVSYQPLGDKA (SEQ ID NO: 11).

In certain embodiments, R₃ comprises a xenoantigen attached to either serine (S) or threonine (T). In certain embodiments, R₃ comprises a xenoantigen-amino acid construct selected from the group consisting of:

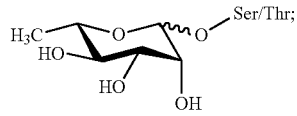

α or β L-Rhammnose eptiope

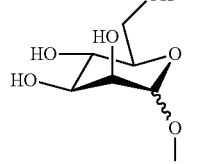

α or β L-Mannose eptiope

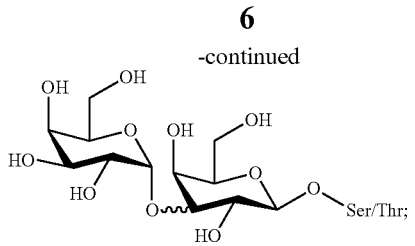

α-Gal disaccharide epitiope

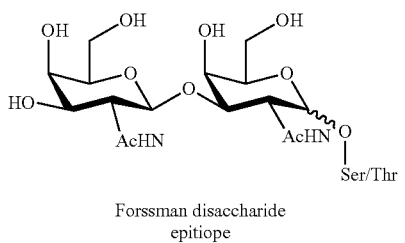

Forssman disaccharide epitiope

In certain embodiments, the composition comprises glycopeptide (11) (SEQ ID NOS 16 and 17 disclosed, respectively, in order of appearance):

(11)

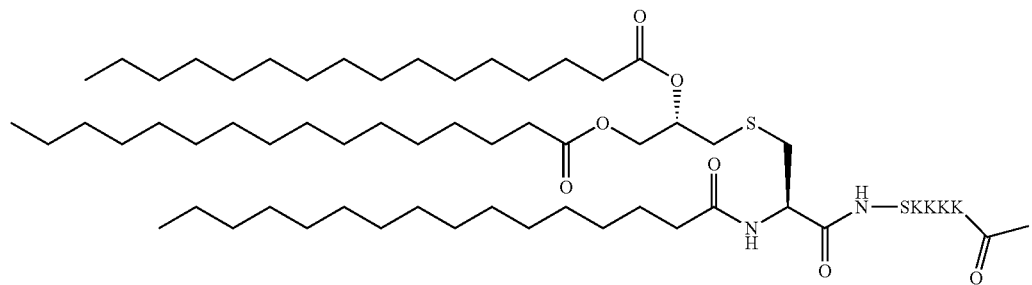

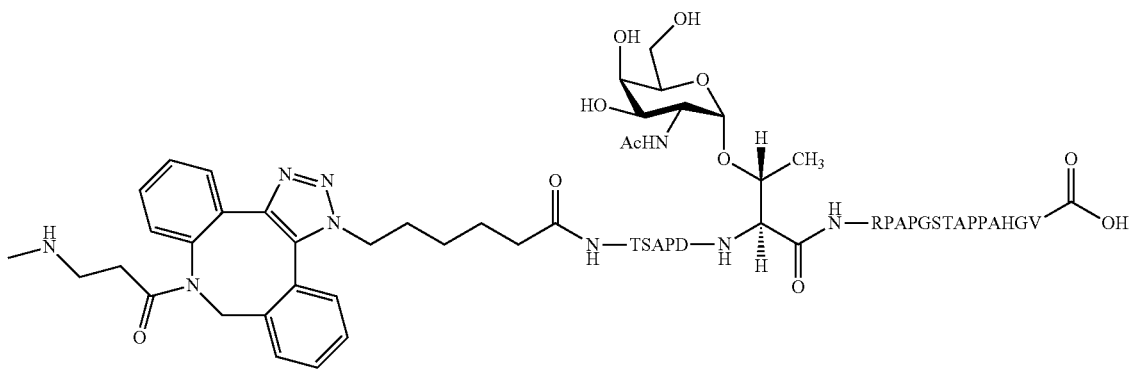

In certain embodiments, the composition comprises adjuvant pathogenic diabetic peptide conjugate (13) (SEQ ID NOS 16 and 18 disclosed, respectively, in order of appearance):

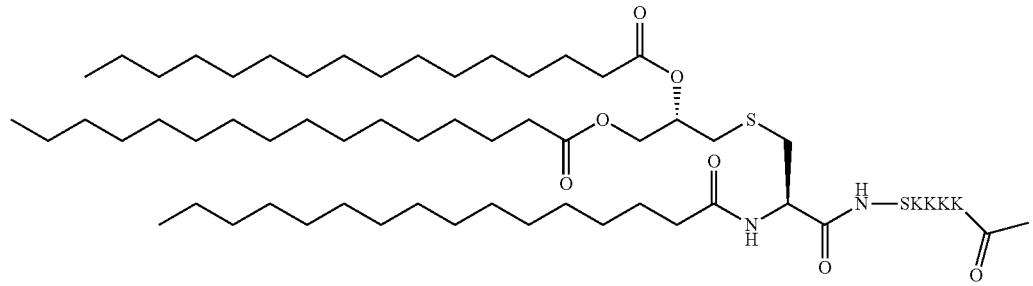

(13)

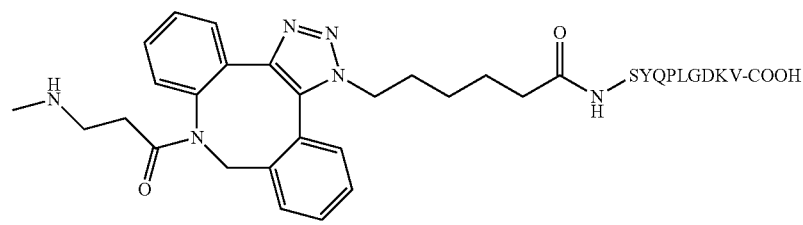

In certain embodiments, the composition comprises adjuvant altered diabetic peptide conjugate (15) (SEQ ID NOS 16 and 19 disclosed, respectively, in order of appearance):

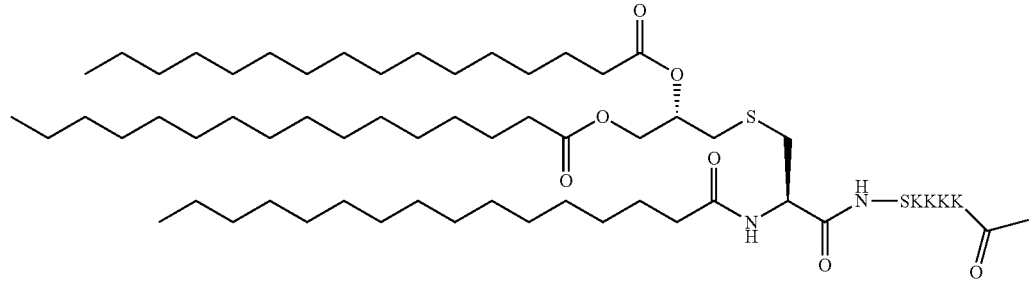

(15)

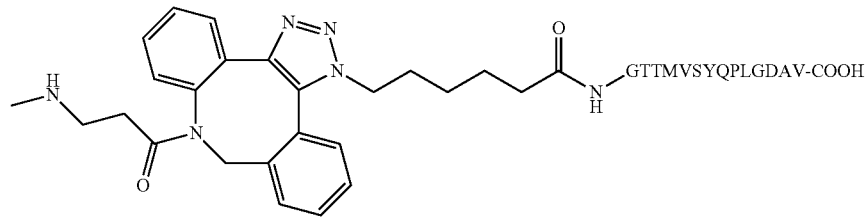

In certain embodiments, the composition comprises MUC1 lipoglycopeptide (22) (SEQ ID NOS 16 and 20 disclosed, respectively, in order of appearance):

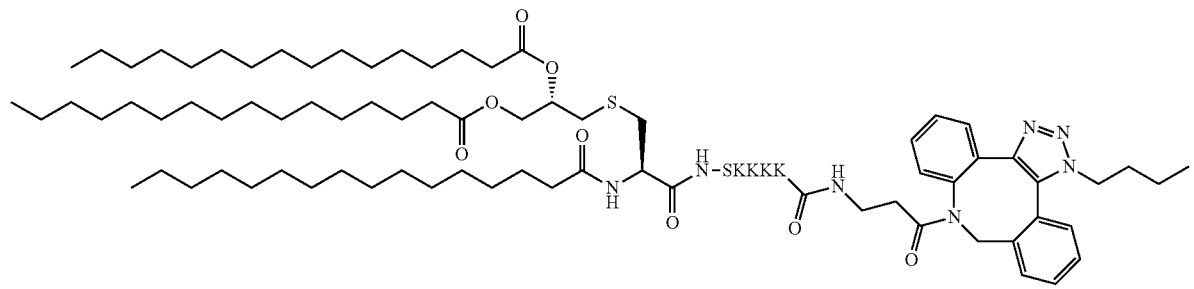
(22)
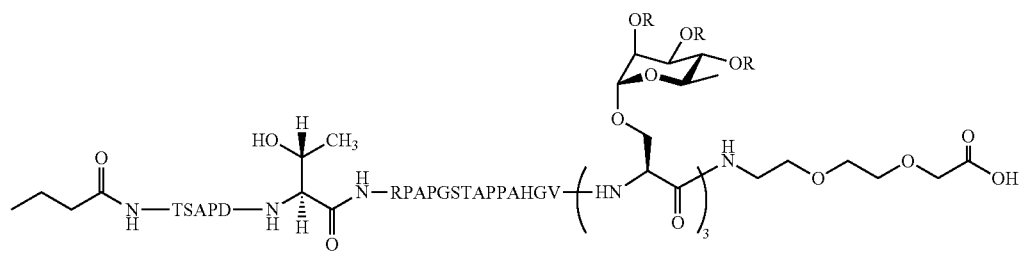
In certain embodiments, the composition comprises pathogenic peptide (30) (SEQ ID NOS 16 and 6, respectively, in order of appearance):
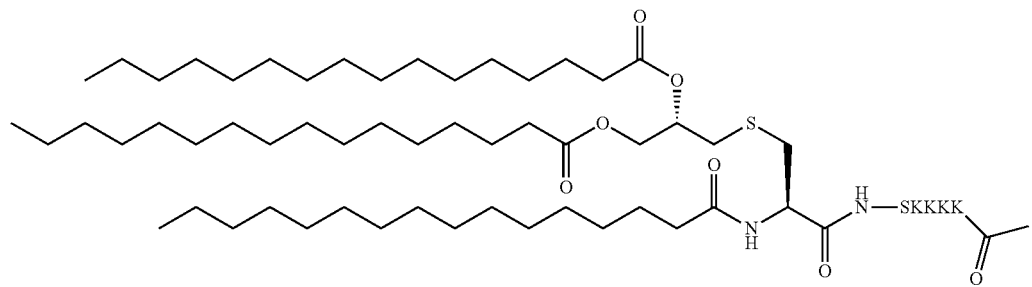
(30)
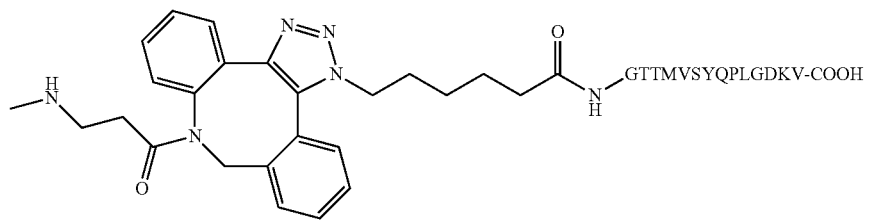
Further provided is a composition comprising Formula II ("CysSK$_4$" disclosed as SEQ ID NO: 16):

Formula II

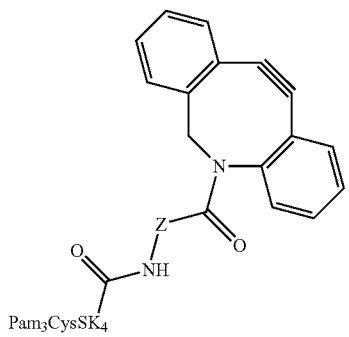

Pam₃CysSK₄ where Z is a linker comprising a chain of $C_{1-n}$ alkyl or $CH_2CH_2(OCH_2CH_2)_n$—, where n is a positive integer. Also provided are protected versions, salts, stereoisomers, racemates, hydrates, solvates, and polymorphs of Formula II.

In certain embodiments, the composition comprises Pam₃CysSK₄-DBCO conjugate (7) ("CysSK₄" disclosed as SEQ ID NO: 16)

(7)

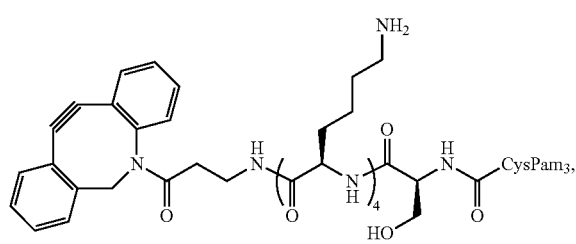

or a protected Pam₃CysSK₄-DBCO conjugate (7) ("CysSK₄" disclosed as SEQ ID NO: 16). In certain embodiments, the protected Pam₃CysSK₄-DBCO conjugate (7) ("CysSK₄" disclosed as SEQ ID NO: 16) comprises a t-butoxycarbonyl (Boc) protecting group.

Further provided is a composition comprising Formula III:

Formula III

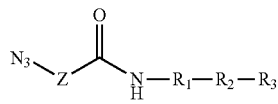

where the dashed line indicates $R_3$ is optional; Z is a linker comprising a chain of $C_{1-n}$ alkyl or $CH_2CH_2(OCH_2CH_2)_n$—, where n is a positive integer; $R_1$ is a heterologous helper T-cell epitope consisting of a sequence of from 7 to 30 amino acids; $R_2$ is either: (i) a B cell epitope in the form of a carbohydrate antigen derived from bacterial cells, viral envelopes, or other infected cell lines, or (ii) a B or T cell epitope consisting of from 7 to 30 amino acids, optionally including a TACA incorporated into the peptide sequence; and $R_3$ is optional, but when present is either: (i) an O-linked xenoantigen attached to an amino acid either via an alpha or beta linkage, or (ii) a plurality of O-linked xenoantigens, where one of the plurality of O-linked xenoantigens is attached to an amino acid either via an alpha or beta linkage; provided, however, that $R_1$ and $R_2$ can together be a single epitope selected from (i) a B cell epitope in the form of a carbohydrate antigen derived from bacterial cells, viral envelopes, or other infected cell lines; and (ii) a B or T cell epitope consisting of from 7 to 30 amino acids, optionally including a TACA incorporated into the peptide sequence. Also provided are salts, stereoisomers, racemates, hydrates, solvates, and polymorphs of Formula III.

In certain embodiments, the composition comprises azide terminated peptide (10) (SEQ ID NO: 17):

(10)

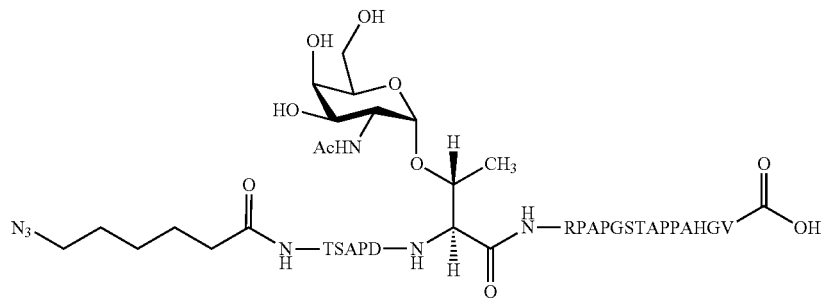

In certain embodiments, the composition comprises azide terminated peptide (12) (SEQ ID NO: 18):

(12)

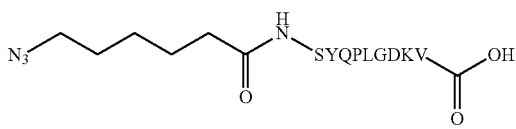

In certain embodiments, the composition comprises azide terminated peptide (14) (SEQ ID NO: 9):

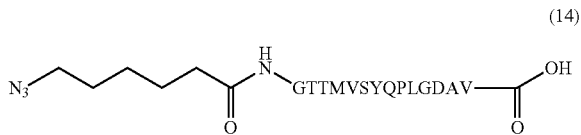

(14)

In certain embodiments, the composition comprises azide terminated peptide (20) or azide terminated peptide (21) (SEQ ID NO: 13):

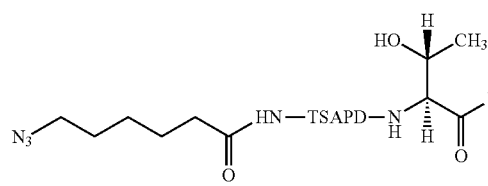

wherein R=OAc (20) or H (21).

Further provided is a vaccine composition comprising a therapeutically effective amount of a composition described herein, and a pharmaceutically acceptable carrier, excipient, or diluent.

Further provided is a method of treating, preventing, or ameliorating a cancer, the method comprising administering an effective amount of a composition described herein to a subject, and treating, preventing, or ameliorating a cancer in the subject.

Further provided is a method for making a vaccine composition, the method comprising reacting a strained alkyne of Formula II ("CysSK$_4$" disclosed as SEQ ID NO: 16):

Formula II

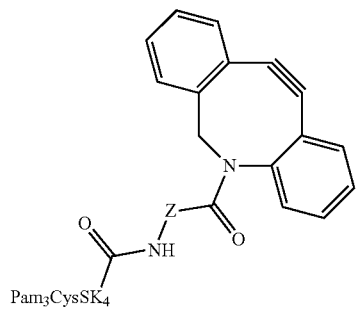

Pam$_3$CysSK$_4$ with an azide of Formula III:

Formula III

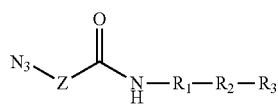

to produce a cycloaddition product, and formulating the cycloaddition product in a vaccine composition; where the dashed line indicates R$_3$ is optional; Z is a linker comprising a chain of $C_{1-n}$ alkyl or $CH_2CH_2(OCH_2CH_2)_n$—, where n is a positive integer; R$_1$ is a heterologous helper T-cell epitope consisting of a sequence of from 7 to 30 amino acids; R$_2$ is either: (i) a B cell epitope in the form of a carbohydrate antigen derived from bacterial cells, viral envelopes, or other infected cell lines, or (ii) a B or T cell epitope consisting of

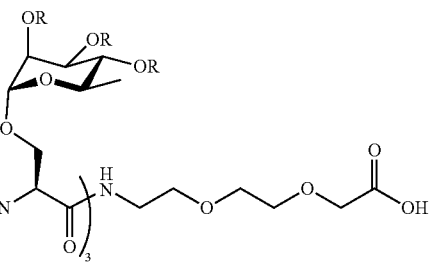

from 7 to 30 amino acids, optionally including a TACA incorporated into the peptide sequence; and R$_3$ is optional, but when present is either: (i) an O-linked xenoantigen attached to an amino acid either via an alpha or beta linkage, or (ii) a plurality of O-linked xenoantigens, where one of the plurality of O-linked xenoantigens is attached to an amino acid either via an alpha or beta linkage; provided, however, that R$_1$ and R$_2$ can together be a single epitope selected from (i) a B cell epitope in the form of a carbohydrate antigen derived from bacterial cells, viral envelopes, or other infected cell lines; and (ii) a B or T cell epitope consisting of from 7 to 30 amino acids, optionally including a TACA incorporated into the peptide sequence. In certain embodiments, the reaction is a Cu-free cycloaddition.

In certain embodiments, the reaction is between (7) as the alkyne component:

(7)

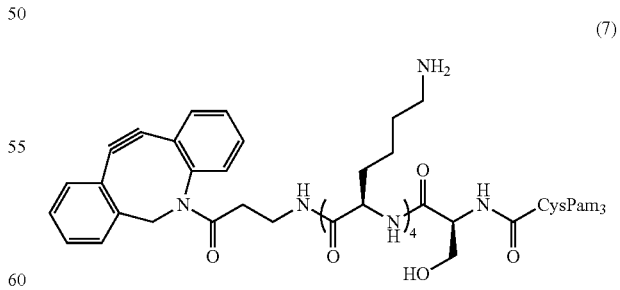

and one of (10), (12), (14), (20), or (21) (SEQ ID NOS 17, 18, 9, and 13 disclosed, respectively, in order of appearance) as the azide component:

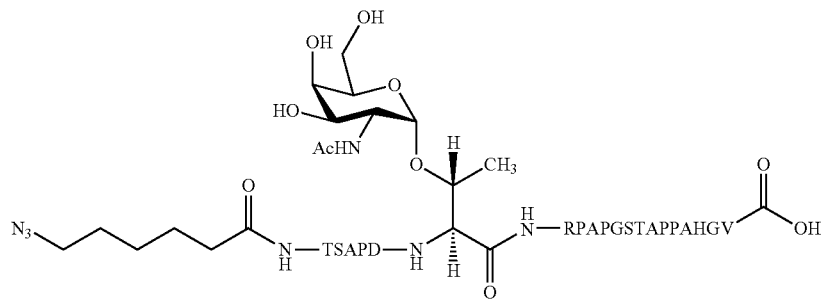

(10)

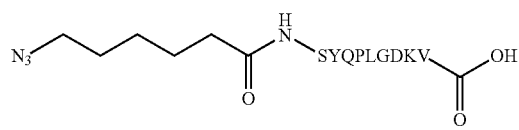

(12)

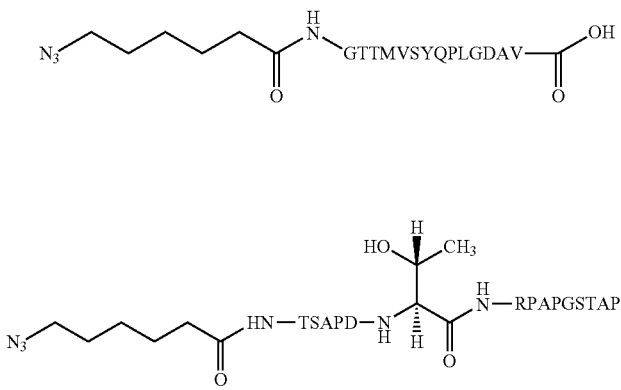

(14)

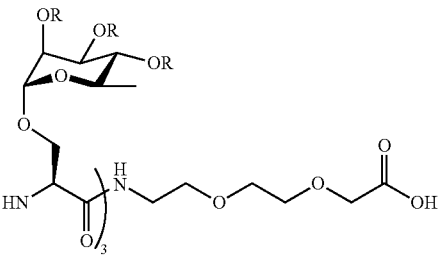

wherein R=OAc (20) or H (21) Further provided is a kit for preparing a vaccine composition, the kit comprising a first container housing a compound of Formula II ("CysSK₄" disclosed as SEQ ID NO: 16):

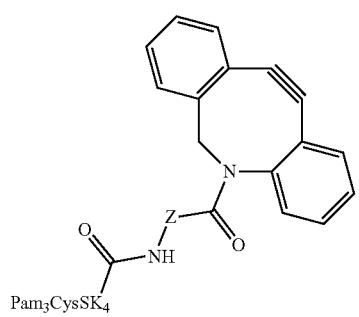

Formula II

Pam₃CysSK₄ and a second container housing a compound of Formula III:

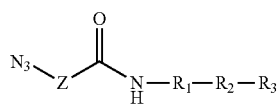

Formula III where the dashed line indicate $R_3$ is optional; Z is a linker comprising a chain of $C_{1-n}$ alkyl or $CH_2CH_2(OCH_2CH_2)_n$—, where n is a positive integer; $R_1$ is a heterologous helper T-cell epitope consisting of a sequence of from 7 to 30 amino acids; $R_2$ is either: (i) a B cell epitope in the form of a carbohydrate antigen derived from bacterial cells, viral envelopes, or other infected cell lines, or (ii) a B or T cell epitope consisting of from 7 to 30 amino acids, optionally including a TACA incorporated into the peptide sequence; $R_3$ is optional, but when present is either: (i) an O-linked xenoantigen attached to an amino acid either via an alpha or beta linkage, or (ii) a plurality of O-linked xenoantigens, where one of the plurality of O-linked xenoantigens is attached to an amino acid either via an alpha or beta linkage; provided, however, that $R_1$ and $R_2$ can together be a single epitope selected from (i) a B cell epitope in the form of a carbohydrate antigen derived from bacterial cells, viral envelopes, or other infected cell lines; and (ii) a B or T cell epitope consisting of from 7 to 30 amino acids, optionally including a TACA incorporated into the peptide sequence.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 4: Non-limiting example tumor glycopeptide sequences with TACAs incorporated (SEQ ID NOS 12 and 13, respectively, in order of appearance).

FIGS. 5A-5B: Non-limiting examples of xenoantigen-amino acid constructs (FIG. 5A), and Scheme 1, depicting the synthesis of an O-linked xenoantigen 19 (FIG. 5B). Reagents and conditions for Scheme 1: (a) p-thiocresol, BF$_3$.OEt$_2$, 0° C. -r.t., 15 h, 79%; (b) Fmoc-Ser-OBn, NIS, TMSOTf, 3 Å molecular sieves, room temperature, 2.5 h, 70%; (c) Hz, Pd/C, 20% Pd, room temperature, 2.5 h, 75%.

FIG. 6: Scheme 2, depicting the synthesis of Pam$_3$Cys-OH 3. Reagents and conditions: (a) (i) CH$_3$CN—CH$_2$Cl$_2$-Et$_2$NH (2:1:2), r.t., 2 h; (ii) PamOH, PyBOP, HOBt, DIPEA, CH$_2$Cl$_2$, r.t., 5 h, 71% (2 steps) [Pam=CH$_3$(CH$_2$)$_{14}$CO]. (b) TFA-DCM (1:1), r.t., 1 h, quantitative.

FIG. 7: Scheme 3, depicting the synthesis of Pam$_3$CysSK$_4$-DBCO conjugate 7 ("CysSK$_4$" disclosed as SEQ ID NO: 16). Reagents and conditions: (a) (i) 25% piperidine, DMF, r.t. 30 min; (ii) HOBt, DIC, N$_\alpha$-Fmoc-N$_\epsilon$-Boc-L-lysine, repeat steps with K, K, K, S, 3; (b) Acetic acid-DCM (1:2), r.t., 2 h; (c) DBCO-amine, T$_3$P, DIPEA, DCM, r.t, 5 h, 73%; (d) TFA-DCM (1:1), r.t., 1 h, quantitative.

FIG. 8: Scheme 4, depicting the synthesis of Pam$_3$CysSK4-DBCO-MUC-1 VNRT-TACA conjugate 11 ("CysSK$_4$" disclosed as SEQ ID NO: 16). Reagents and conditions: (a) (i) 25% piperidine, DMF, r.t. 30 min; (ii) HOBt, DIC, NMP, FmocNH-Gly-OH, repeat steps with H, A,P, P, A, T, S, G, P, A, P, R, T(Ac$_{3\alpha}$-GalNAc), D, P, A, S, T, 6-azido hexanoic acid; (b) 88% TFA, 3% thioanisole, 5% ethanedithiol, 2% water, and 2% phenol; (c) NaOMe, MeOH, r.t., 2 h, 100%; (d) 7, MeOH-DCM (1:1), r.t, 12 h, quantitative. FIG. 8 also discloses SEQ ID NOS 17, 17, 16, and 17, respectively in order of appearance.

FIG. 9A: Scheme 5, depicting the synthesis of Pam$_3$CysSK$_4$-DBCO-pathogenic diabetic peptide conjugate ("CysSK$_4$" disclosed as SEQ ID NO: 16) 13 (SEQ ID NOS 18, 16, and 18, respectively, in order of appearance) (FIG. 9A), Scheme 6, depicting the synthesis of altered diabetic peptide 15 (SEQ ID NOS 19, 16, and 9, respectively, in order of appearance) (FIG. 9B), and Scheme 7, depicting synthesis of MUC 1 lipoglycopeptide 22 (SEQ ID NOS 17, 16, and 20, respectively, in order of appearance) (FIG. 9C).

FIG. 18 discloses SEQ ID NO 17.

FIG. 19 also discloses SEQ ID NOS 16 and 17, respectively in order of appearance.

FIG. 20 also discloses SEQ ID NOS 16 and 18, respectively, in order of appearance.

FIG. 26A shows a graph of commercially pooled human serum with Rha-specific ELISA to determine the concentration of anti-rhamnose antibody in serum. FIG. 26B shows a graph of rhamnose specific ELISA with different fractions from the Rha-affinity column showing the presence of anti-rhamnose antibodies in each. The pass through contained no anti-rhamnose activity. FIG. 26C shows natural anti-Rha antibodies found in human serum are mostly IgM and IgG1 and 3. FIG. 26D shows purified and anti-Rha antibody also reflects this distribution.

FIG. 27A shows anti-MUC1-Tn antibody production after mice were injected with human anti-Rha or pass through (no anti-Rha) antibody and then one hour later MUC1-Tn antigen vaccine with or without Rhamnose. Shown are ELISA results on MUC1-Tn-coated plates. FIG. 27B shows concentration dependent and MUC1-Tn-specific CD4+ T cell proliferative response of the four different groups. FIG. 27C shows data from FIG. 27B plotted at 20 µg/ml. Control group and MUC1 non-specific proliferation were subtracted.

FIG. 28A shows concentration dependent in vitro CD8+ T cell proliferative response of group A with varying amounts of MUC1-Tn antigen. FIG. 28B shows MUC1-Tn-specific CD8+ T cell proliferative response of the four different groups (40 µg/ml MUC1-Tn). Control group and MUC1-non-specific proliferation were subtracted. FIG. 28C shows CD8+ T cell specific IFN-Y production in the four groups of mice at 40 µg/ml CD8 MUC1-Tn epitope peptide. FIG. 28D shows apoptosis of EL4 cells presenting the CD8 epitope peptide induced by CD8+ T cells of the different groups. The ratio of EL4 to CD8+ cells was 1:100.

DETAILED DESCRIPTION OF THE INVENTION

Figure 1A:
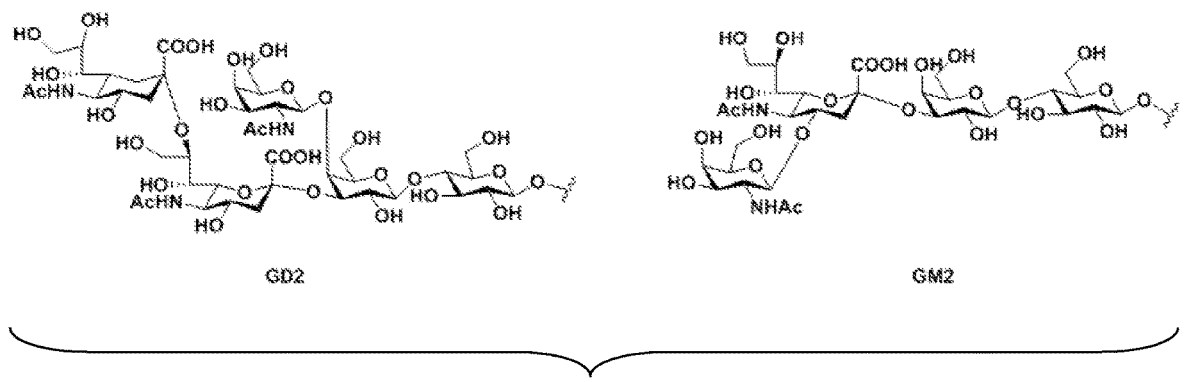
FIG. 1A: Non-limiting example TACAs linked to lipid.
Figure 1B:
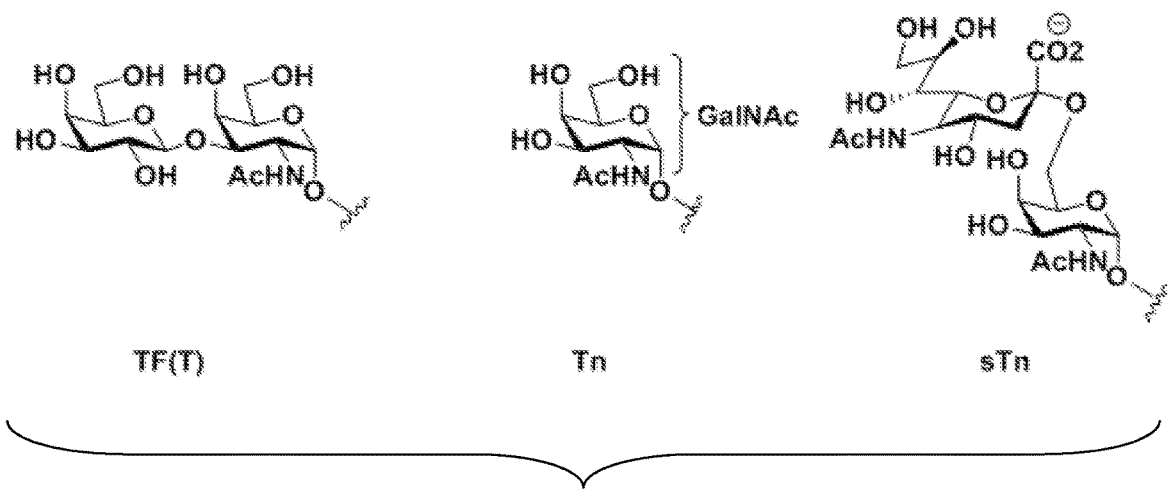
FIG. 1B: Non-limiting example TACAs found on MUC-1 protein.
Figure 2:
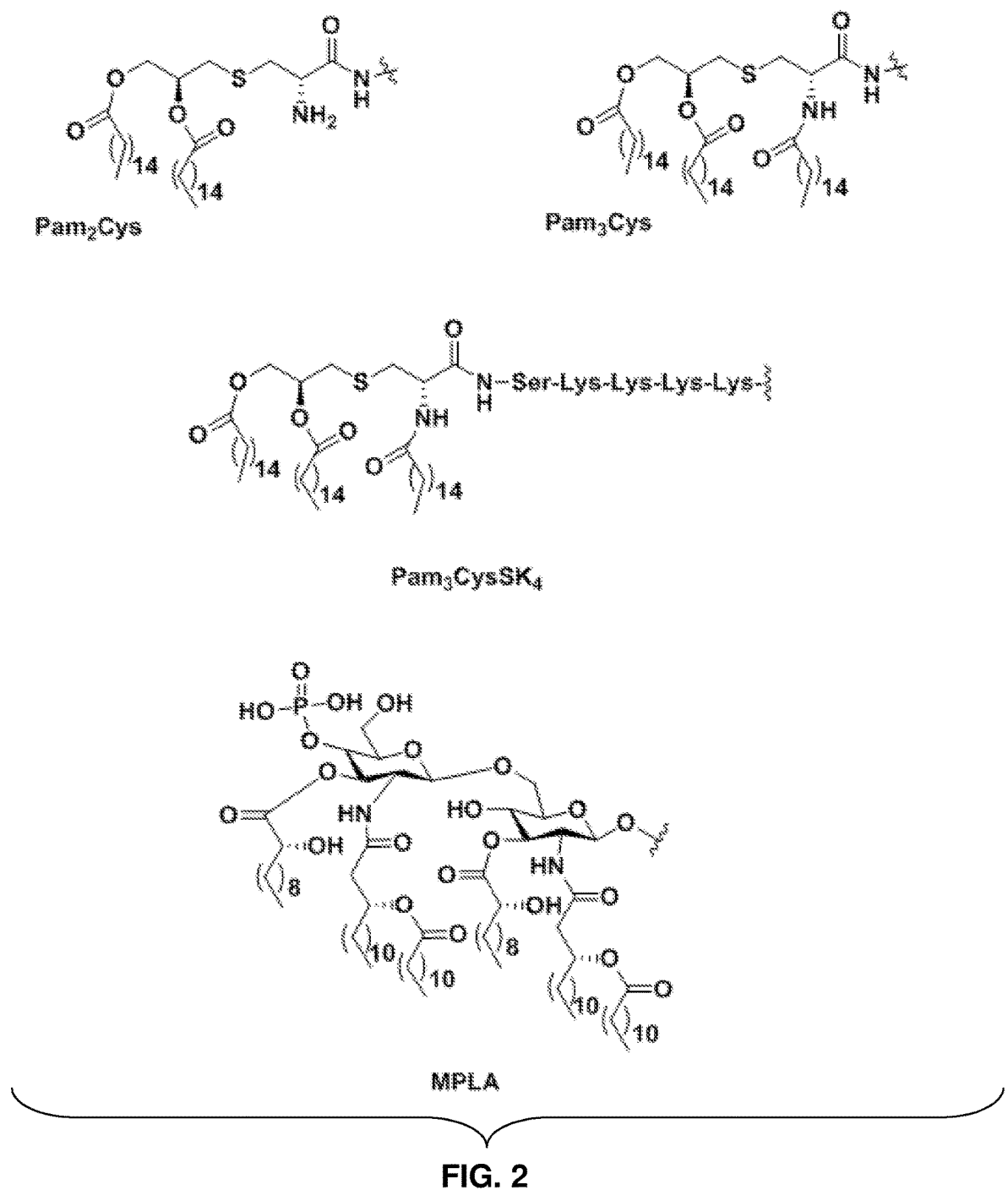
FIG. 2: Non-limiting examples of adjuvants or small molecule carriers ("CysSK$_4$" disclosed as SEQ ID NO: 16).

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Definitions

For convenience, certain terms are defined, and certain concepts are established, prior to further description of the present disclosure.

Unless stereochemistry is specifically indicated, all stereoisomers of the compounds herein are included, as pure compounds as well as mixtures thereof. It will be appreciated by one of ordinary skill in the art that asymmetric centers may exist in any of the compounds disclosed herein. Thus, the compounds and compositions thereof may be in the form of an individual enantiomer, diastereomer, or geometric isomer, or may be in the form of a mixture of stereoisomers. In certain embodiments, the compounds herein are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

The term "composition" as used herein is intended to encompass a product comprising the specified ingredients in the specified amounts, as well as any product that results, directly or indirectly, from combinations of the specified ingredients in the specified amounts.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine Solvates are sometimes termed "pseudopolymorphs."

The term "hydrate" refers to a solvate with water.

The term "racemate" refers to a mixture that contains an equal amount of enantiomers.

The term "polymorph" means a crystalline form of a substance that is distinct from another crystalline form of the substance but that shares the same chemical formula.

It will be appreciated that any of the compounds described herein may be substituted with any number of substituents or functional moieties. In general, the term "substituted," whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position. The term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents of organic compounds. Combinations of substituents and variables envisioned are preferably those that result in the formation of stable compounds useful in the treatment, for example, of cancers.

The term "pharmaceutically acceptable carrier" means a medium that is used to prepare a desired dosage form of the compound. A pharmaceutically acceptable carrier includes solvents, diluents, or other liquid vehicles; dispersion or suspension aids; surface active agents; isotonic agents; thickening or emulsifying agents; preservatives; solid binders; lubricants; and the like.

The term "protecting group" as used herein refers to a group which is introduced onto a functional group in a compound and which modifies that functional group's chemical reactivity. Typically, the protecting group modifies the functional group's chemical activity in such a way that it renders the functional group chemically inert to the reaction conditions used when a subsequent chemical transformation is effected on the compound. Non-limiting example protecting groups include t-butoxycarbonyl (Boc), formyl, acetyl, allyl, F-moc, benzoyl, pivaloyl, t-butylacetyl, phenylsulfonyl benzyl, benzyloxycarbonyl (Cbz), and the like.

The term "alkyl" refers to monovalent alkyl groups having from 1 to 50 carbon atoms, preferably having from 1 to 10 carbon atoms, and more preferably having from 1 to 6 carbon atoms. This term is exemplified by groups such as methyl, ethyl, n-propyl, iso-propyl, n-butyl, iso-butyl, n-hexyl, and the like. "Substituted alkyl" refers to an alkyl group, preferably of from 1 to 10 carbon atoms, having from 1 to 3 substituents selected from the group consisting of alkoxy, substituted alkoxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, aryl, heteroaryl, heterocyclic, aryloxy, thioaryloxy, heteroaryloxy, thioheteroaryloxy, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, and heterocyclic.

The term "$C_{1-n}$ alkyl" can be any linear or branched alkyl group containing 1 to n carbon atoms. For example, the term "$C_{1-6}$ alkyl" can comprise groups such as methyl, ethyl, propyl, isopropyl, butyl, isobutyl, sec-butyl, tert-butyl, pentyl, isopentyl (3-methylbutyl), neopentyl (2,2-dimethylpropyl), hexyl, isohexyl (4-methylpentyl), and the like.

The term "aryl" refers to an unsaturated aromatic carbocyclic group, preferably of from 6 to 14 carbon atoms, having a single ring (e.g., phenyl) or multiple condensed rings (e.g., naphthyl or anthryl), preferably having from 1 to 3 rings. Example aryls include phenyl, naphthyl, and the like. Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, heterocyclic, and the like. Example substituents include alkyl, alkoxy, halo, cyano, nitro, trihalomethyl, and thioalkoxy.

The term "xenoantigen" is to be understood to mean at least one foreign antigen capable of binding natural antibodies. Examples of xenoantigens include, but are not limited to, the α-gal epitope, L-Rha, and the Forssman disaccharide.

As used herein, the term "lipid" is defined to include any of a broad range of substances that is characteristically insoluble in water and extractable with an organic solvent. This broad class of compounds is known to those of skill in the art, and as the term "lipid" is used herein, it is not limited to any particular structure. Examples include compounds which contain long-chain aliphatic hydrocarbons and their derivatives. A lipid may be naturally occurring or synthetic. Biological lipids are well known in the art and include, for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods described herein.

General Description

Provided herein are vaccine compositions composed of a lipidated peptide or glycopeptide antigen that optionally incorporates a xenoantigen together in a single molecule. The compositions are more readily assembled than known vaccine compositions incorporating a xenoantigen as part of a second molecule or component. Further, covalent combination of a lipid antigen and a xenoantigen ensures colocalization of all components. The antigen and xenoantigen components can be assembled by automated solid phase peptide synthesis for straightforward manufacturing. Moreover, endogenous natural antibodies against xenoantigens can be used to improve uptake of antigens by antigen presenting cells. Thus, the vaccine compositions described herein provide for improved uptake of the antigens.

Provided are single molecule, multi-functional, fully synthetic carbohydrate vaccine compositions. The present disclosure provides facile conjugation chemistry to synthesize a cycloaddition product, involving the reaction between a strained alkyne-terminated component and an azide-terminated component. The vaccine composition has the general structure of Formula I ("CysSK$_4$" disclosed as SEQ ID NO: 16):

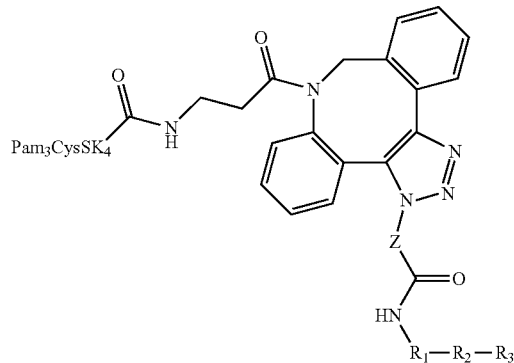

Formula I where the dashed line indicates $R_3$ is optional; Z is a linker consisting of a chain of $C_{1-n}$ alkyl or $CH_2CH_2(OCH_2CH_2)_n$—, where n is a positive integer; $R_1$ is a heterologous helper T-cell epitope consisting of a sequence of from 7 to 30 amino acids, or a bond when $R_2$ does not require an additional helper T-cell epitope; $R_2$ is either (i) a B cell epitope in the form of a carbohydrate antigen derived from bacterial cells, viral envelopes, or other infected cell lines, or (ii) a B or T cell epitope consisting of from 7 to 30 amino acids, optionally including a TACA incorporated into the peptide sequence; and $R_3$ is optional, but when present is either (i) an O-linked xenoantigen attached to an amino acid via either an alpha or beta linkage, or (ii) a plurality of O-linked xenoantigens, where one of the plurality of O-linked xenoantigens is attached to an amino acid via either an alphra or beta linkage; provided, however, that $R_1$ and $R_2$ can together be a single epitope selected from (i) a B cell epitope in the form of a carbohydrate antigen derived from bacterial cells, viral envelopes, or other infected cell lines; and (ii) a B or T cell epitope consisting of from 7 to 30 amino acids, optionally including a TACA incorporated into the peptide sequence. It is understood that in various embodiments of Formula I when $R_3$ is not present, a COOH group, which represents the carboxy terminus of the last amino acid in the $R_1$ or $R_2$ epitope, may be depicted in its place.

Conjugating carbohydrate antigens with a protein carrier has shown ability to augment the immunogenicity by engaging helper T cells. An alternative is to use pattern recognition receptor (PRR) ligands to activate antigen presenting cells (APCs). PRRs, such as Toll-like receptors (TLRs), C-type lectin receptors (CLRs), and the like, bind to lipopolysaccharide, lipopeptide, and other pathogen-associated molecules, and facilitate APC maturation. Mannose receptors (MRs), a kind of CLRs, have been used for antigen uptake. MRs bind to polysaccharides terminated in mannose and fucose found in some glycoproteins and microbes. Higher INF-γ levels have been observed with a mannose functionalized carrier along with a cancer antigen and TLR ligand.

Pam$_3$Cys, a synthetic lipopeptide, is an adjuvant that is a TLR-2 agonist. Stronger versions of the same ligand, Pam$_3$CysSKKKK— ("CysSKKKK" disclosed as SEQ ID NO: 16), Pam$_2$Cys, and Pam$_2$CysSKKKK ("CysSKKKK" disclosed as SEQ ID NO: 16), evoke antibody response with single and clusters of TACAs. TACA-specific IgG response has been observed with the help of Monophosphoryl lipid A (MPLA), a TLR-4 lipopolysaccharide Immunologically, it is preferable to incorporate the adjuvant and antigen into a single molecule over the use of two different components as a mixture. The single constituent aspect of the vaccine composition described herein ensures the exposure of antigen to APCs activated by adjuvants. Uptake of antigen by APCs is important for strong antibody response, since APCs are the mediators that call for help from the adaptive immune response when an infection outruns innate immunity. Targeting theses cells, such as dentritic cells (DCs), macrophages, and the like, helps the presentation of antigens to T-cells via major histocompatibility complex (MHC)-class I and II molecules.

Both T-helper cells and cytotoxic T-cells are important for vaccine immunogenicity and efficacy. Inclusion of T-cell epitopes into a vaccine construct has shown potent antigen specific T-cell response. Higher cytokine release has also been observed. Suitable T-cell epitopes include, but are not limited to: QYIKANSKFIGITEL (SEQ ID NO: 1) (tetanus toxoid epitope), KLFAVWKITYKDTG (SEQ ID NO: 2) (epitope derived from *N. meningitis*), YAFKYAR-HANVGRNAFELFL (SEQ ID NO: 3) (epitope derived from *N. meningitis*), ISQAVHAAHAEINEAGR (SEQ ID NO: 4) (epitope derived from ovalbumin), and A'KZVAAW-TLKAA' (SEQ ID NO: 5) (Pan DR epitope; where A' is D-alanine, and Z is L-cyclohexylalanine).

Figure 3:
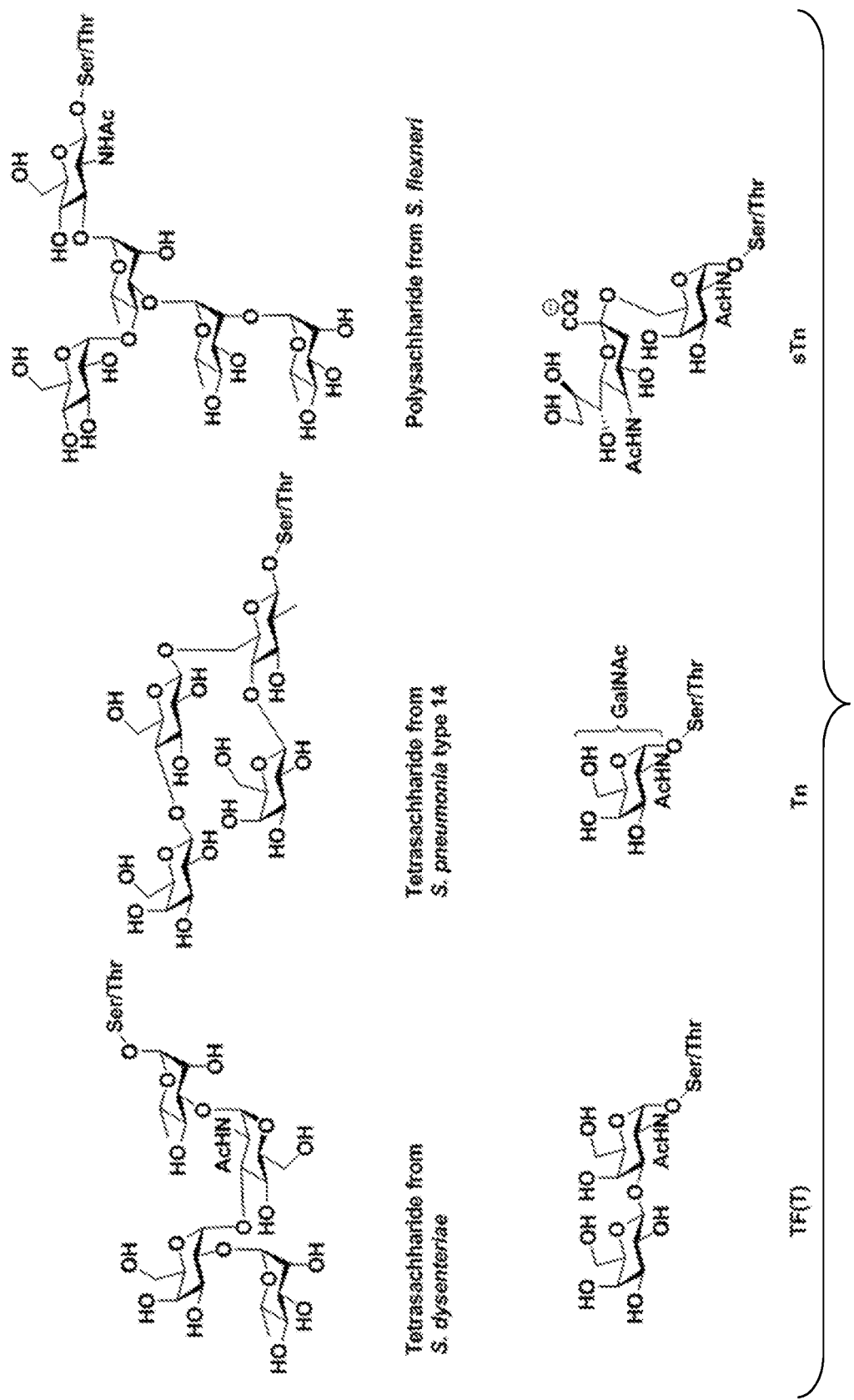
FIG. 3: Non-limiting examples of carbohydrate antigens linked to amino acid residues.

With respect to $R_2$, the characteristic polysaccharides on bacterial cells, viral envelopes, and other infected cell lines have highly conserved structures that may be remarkable antigens. In some embodiments, the carbohydrate antigen is covalently linked to an amino acid residue. In one non-limiting example, the amino acid residue is serine (S) or threonine (T). Suitable $R_2$ moieties include, but are not limited to, the carbohydrate antigen-amino acid constructs depicted in FIG. 3, the tumor glycopeptide sequences having incorporated TACAs shown in FIG. 4, and the following pathogenic or altered diabetic peptide sequences: GTTMVSYQPLGDKV (SEQ ID NO: 6), SYQPLGDKV (SEQ ID NO: 7), SYQPLGDAV (SEQ ID NO: 8), GTTMVSYQPLGDAV (SEQ ID NO: 9), SYQPLGDKA (SEQ ID NO: 10), and GTTMVSYQPLGDKA (SEQ ID NO: 11). GTTMVSYQPLGDKV (SEQ ID NO: 6) and SYQPLGDKV (SEQ ID NO: 7) are pathogenic diabetic peptide sequences, and GTTMVSYQPLGDAV (SEQ ID NO: 9) and SYQPLGDAV (SEQ ID NO: 8) are altered anti-diabetic (i.e., protective) peptide sequences. SYQPLGDKV (SEQ ID NO: 7) may also be referred to herein as GAD 546-554, and GTTMVSYQPLGDKV (SEQ ID NO: 6) may also be referred to herein as GAD 541-554.

$R_3$ may be one or more O-linked xenoantigens. In some embodiments of Formula I when $R_3$ is present, the amino acid in $R_3$ is serine (S) or threonine (T). Non-limiting examples of suitable $R_3$ moieties include, but are not limited to, the xenoantigen-amino acid constructs shown in FIG. 5. $R_3$ may also include a plurality of any of the xenoantigens depicted in FIG. 5, with one of the plurality attached to an amino acid such as serine (S) or threonine (T). For example, $R_3$ may be composed of two or more α-Gal disaccharide epitopes linked together, with one of the α-Gal disaccharide epitopes attached to an amino acid such as serine (S) or threonine (T). Scheme 1 (FIG. 5B) depicts the synthesis of an O-linked xenoantigen 19 for inclusion in peptide synthesis.

In some embodiments, Z is a $C_{1-5}$ alkyl chain. However, it is understood that many other linkers are possible and entirely encompassed within the present disclosure.

Antibody-mediated targeting of APCs has been explored. Anti Galα1-3Galβ1 (αGal) antibodies naturally present in humans binds to the αGal epitope incorporated into some embodiments of the vaccine composition described herein. Interaction between the Fc portion of the antibodies and Fcγ receptors present on APCs leads to higher uptake and presentation of antigen. A human serum profiling has catalogued anti-carbohydrate antigens in serum, anti L-rhamnose (L-Rha) (β-linked) being most abundant. Incorporating L-Rha epitope generally results in a higher antibody titer response against a cancer antigen. Antibodies against α-linked L-Rha, α-Gal, and the Forssman disaccharide are also predominant. Thus, $R_3$ in Formula I, when present, can include a xenoantigen such as L-Rha, α-Gal, and the Forssman disaccharide.

A non-limiting example of a compound of Formula I is glycopeptide (11) (SEQ ID NOS 16 and 17, respectively, in order of appearance):

(11)

A non-limiting example synthetic route for the production of glycopeptide (11) is illustrated in Scheme 4 (FIG. 8).

Another non-limiting example of a compound of Formula I is adjuvant pathogenic diabetic peptide conjugate (13) (SEQ ID NOS 16 and 18, respectively, in order of appearance):

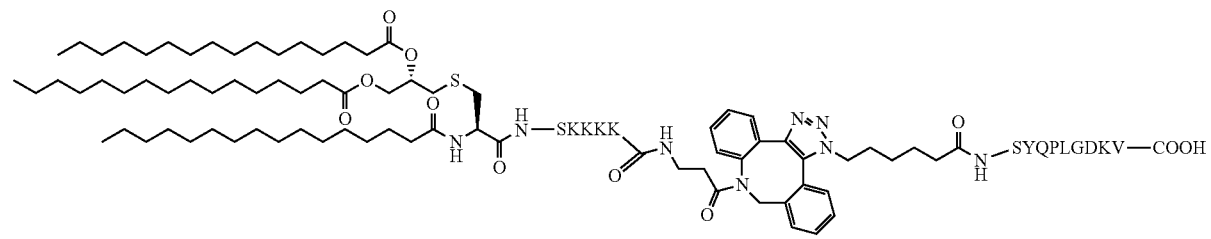

(13)

A non-limiting example synthetic route for the production of adjuvant pathogenic diabetic peptide conjugate (13) is illustrated in Scheme 5 (FIG. 9A).

Another non-limiting example of a compound of Formula I is adjuvant altered diabetic peptide conjugate (15) (SEQ ID NOS 16 and 19, respectively, in order of appearance):

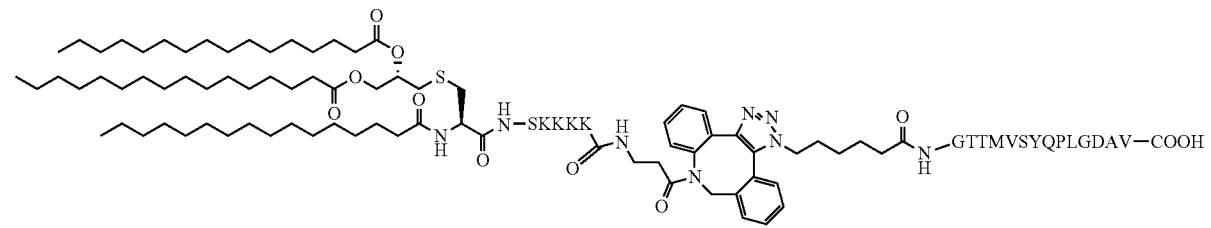

(15)

A non-limiting example synthetic route for the production of adjuvant altered diabetic peptide conjugate (15) is illustrated in Scheme 6 (FIG. 9B).

Another non-limiting example of a compound of Formula I is MUC1 lipoglycopeptide (22) (SEQ ID NOS 16 and 20, respectively, in order of appearance):

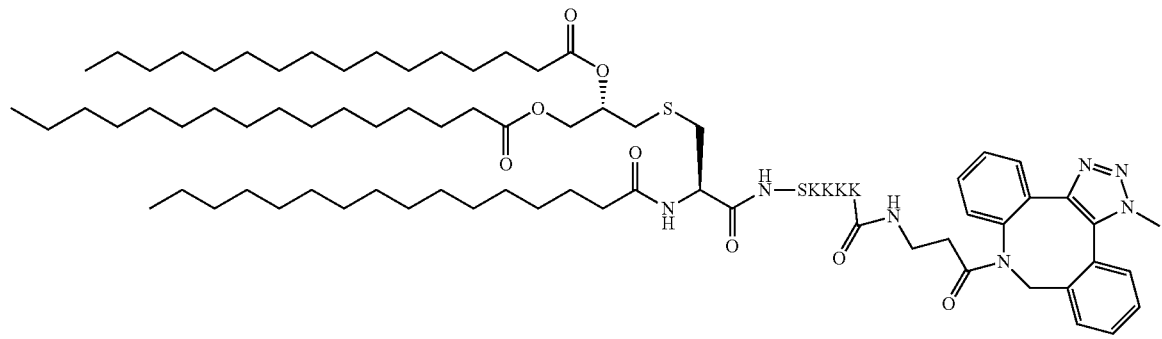

(22)

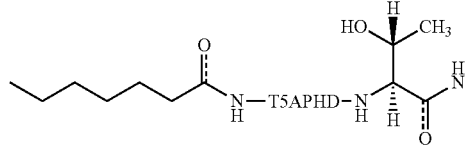
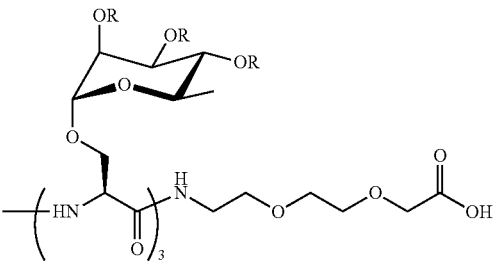

A non-limiting example synthetic route for the production of MUC1 lipoglycopeptide (22) is illustrated in Scheme 7 (FIG. 9C).

Another non-limiting example of a compound of Formula I is the pathogenic peptide (30) (SEQ ID NOS 16 and 6, respectively, in order of appearance):

(30)

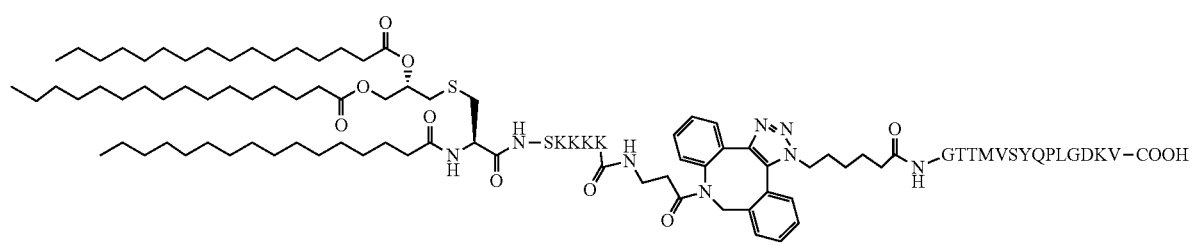

Figure 32:
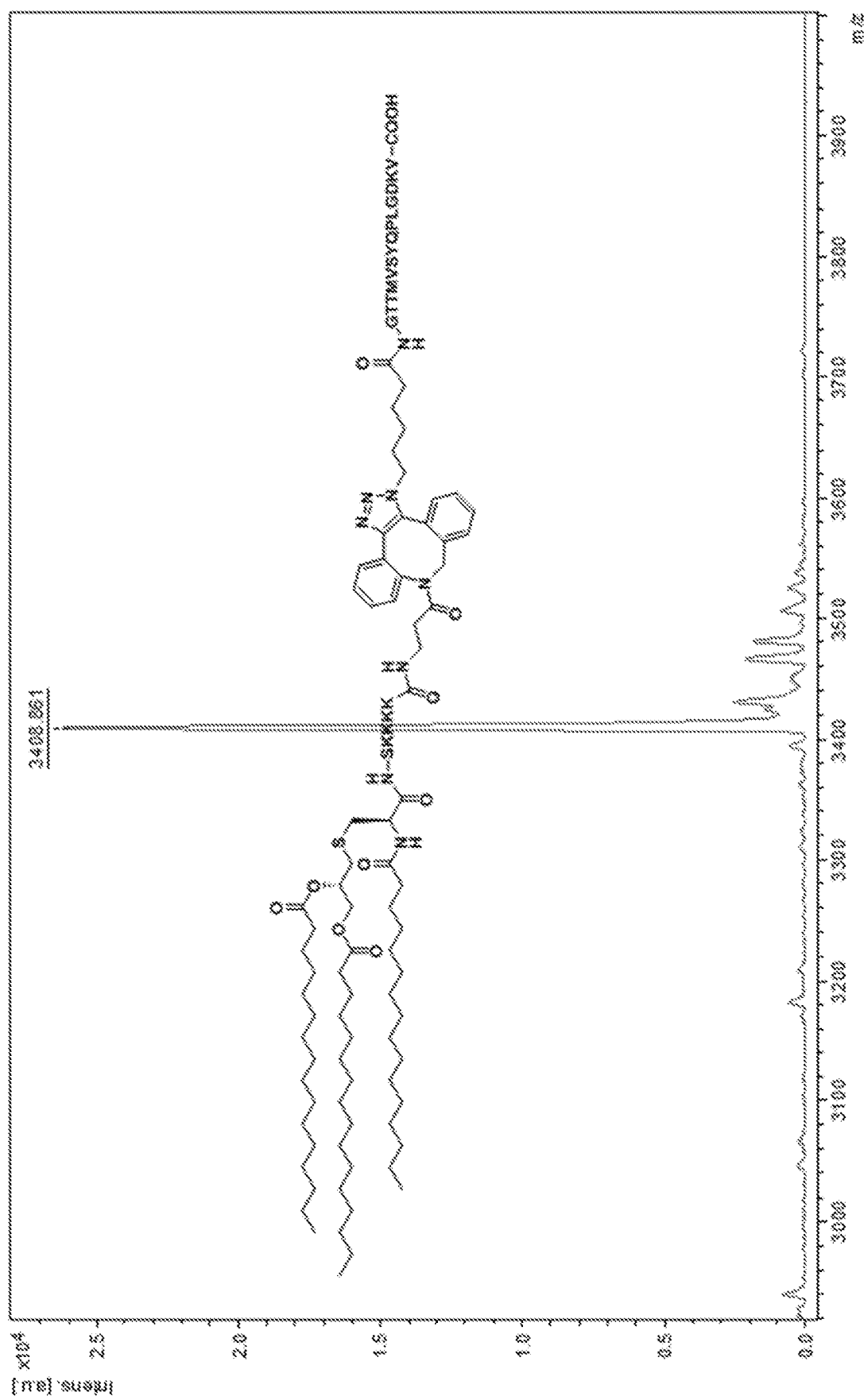
FIG. 32: HRMS spectrum of peptide conjugate (30).

The pathogenic peptide (30) was prepared through the same synthetic approach as the above examples. The HRMS spectrum of (30) is shown in FIG. 32.

The present disclosure provides a self-adjuvanting and self-targeting antigenic vaccine composition. The covalent attachment of adjuvant and xenoantigen to the antigen, as a single component, increases the probability of activation of APCs and uptake of antigen by the same cells. The compositions of Formula I, including conjugates or liposomal formulations thereof, can be used in vaccines for the treatment, prevention, or amelioration of various diseases, such as certain cancers or infections, or diabetes. Furthermore the compositions of Formula I can be formulated in liposomal compositions. In some embodiments, a composition of Formula I is formulated in a liposome, and the liposome is conjugated to an antibody. The antibody on the liposome makes it easier for the whole conjugate to be picked up and presented by APCs, and therefore enhances the activity. In one non-limiting example, the antibody is anti-mouse F4/80, however other antibodies are possible and entirely encompassed within the scope of the present disclosure.

Additionally, the compositions of Formula I can be utilized for screening purposes. For example, the compositions can be used to screen human blood cells for the human response to the peptides included in the composition. This is useful for personalized medicine.

The weak immunogenicity of carbohydrate antigens is addressed by conjugating TACAs with immunoadjuvants. Different conjugation systems such as amide coupling, thiol-maleimide reactions, and a disulfide linkage are possible. Among these, Cu-catalyzed azide-alkyne cycloaddition, also called "click chemistry", can be used. High yields and good chemoselectivity make click chemistry the best fit for the conjugation. Various reaction conditions with different Cu sources, for example $CuSO_4$, CuI, and Cu acetate, along with mild reducing agents, such as sodium ascorbate, are generally used. Click chemistry involves considerable optimization in individual systems, affecting total reaction time, optimum temperature, and reagents.

The modification of traditional click chemistry with a strained alkyne leads to a Cu free azide-alkyne cycloaddition. The sp hybridized carbons in cyclooctyne have a bond angle of 160°, which accelerates the rate of reaction. A further increase in reactivity is possible with the incorporation of biphenyl or difluro groups. The absence of Cu from the system reduces the toxicity profile of the reaction. As a result, Cu-free cycloaddition has been reported in cells and living organisms. Different derivatives of strained alkyne, for example, biarylazacyclooctynone (BARAC), difluorinated cyclooctynes (DIFO), dibenzocyclooctynes (DIBO), and the like, are synthesized and used as molecular probes for labeling cells, and glycoconjugates in living systems.

As noted, Formula I can be prepared by reacting a strained alkyne component with an azide component, such as depicted in Schemes 4-6 (FIGS. 8-9). In some embodiments, the strained alkyne component is a strained alkyne $Pam_3CysSK_4$ ("CysSK$_4$" disclosed as SEQ ID NO: 16) composition having Formula II ("CysSK$_4$" disclosed as SEQ ID NO: 16):

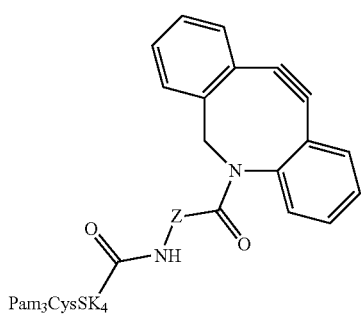

Formula II

Pam₃CysSK₄ where Z represents a linker consisting of a chain of $C_{1-n}$ alkyl or $CH_2CH_2(OCH_2CH_2)_n$—, where n is a positive integer. In one non-limiting example of Formula II, Z is a $C_{1-4}$ alkyl chain. Though Formula II is described for exemplary purposes, other strained alkyne components are possible and are entirely within the scope of the present disclosure. Compounds of Formula II can be prepared according to Scheme 2, shown in FIG. 7. It is understood that protected versions of Formula II are included within the present disclosure. One non-limiting example of a suitable protecting group for preparing a compound of Formula II is t-butoxycarbonyl (Boc). Compounds of Formula II are useful for preparing vaccines because they can be reacted with azide components containing one or more antigens as described herein, and thereby allow for the adjuvant and antigen to be in a single molecule, ensuring the exposure of antigen to APCs activated by the adjuvant.

One non-limiting example of a compound of Formula II is the Pam₃CysSK₄-DBCO conjugate (7) ("CysSK₄" disclosed as SEQ ID NO: 16):

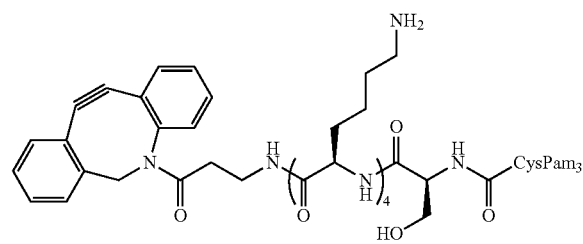

(7)

It is understood that protected versions of conjugate (7) are included within the present disclosure. One non-limiting example of a suitable protecting group for preparing a protected conjugate (7) is t-butoxycarbonyl (Boc).

In some embodiments, the azide component has the structure of Formula III:

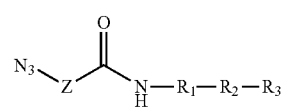

Formula III where the dashed line indicates $R_3$ is optional; Z represents a linker consisting of a chain of $C_{1-n}$ alkyl or $CH_2CH_2(OCH_2CH_2)_n$—, where n is a positive integer; $R_1$ is a heterologous helper T-cell epitope consisting of a sequence of from 7 to 30 amino acids; $R_2$ is either (i) a B cell epitope in the form of a carbohydrate antigen derived from bacterial cells, viral envelopes, or other infected cell lines, or (ii) a B or T cell epitope consisting of from 7 to 30 amino acids, optionally including a TACA incorporated into the peptide sequence; and $R_3$ is optional, but when present is either (i) an O-linked xenoantigen attached to an amino acid either vai alpha or beta linkage, or (ii) a plurality of O-linked xenoantigens, where one of the plurality of O-linked xenoantigens is attached to an amino acid via either an alpha or beta linkage; provided, however, that $R_1$ and $R_2$ can also together be a single epitope, such as a B or T cell epitope consisting of from 7 to 30 amino acids. In one non-limiting example of Formula III, Z is a $C_5$ alkyl chain. Though Formula III is described for exemplary purposes, other azide components are possible and are entirely within the scope of the present disclosure.

One non-limiting example of a compound of Formula III is the azide terminated peptide (10) (SEQ ID NO: 17):

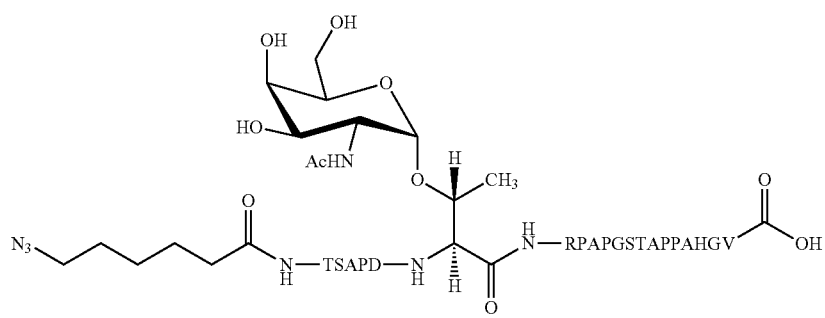

(10)

Another non-limiting example of a compound of Formula III, where R₂ and R₃ are together a single epitope, is the azide terminated peptide (12) (SEQ ID NO: 18):

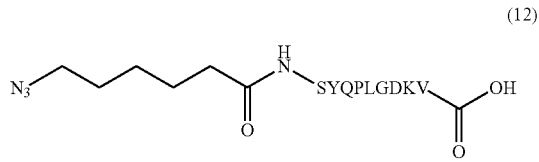

(12)

Another non-limiting example of a compound of Formula III is the azide terminated peptide (14) (SEQ ID NO: 9):

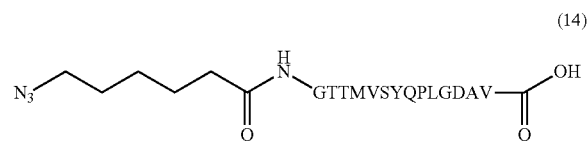

(14)

Additional non-limiting examples of compound of Formula III are the azide terminated peptides (20) and (21) (SEQ ID NO: 13):

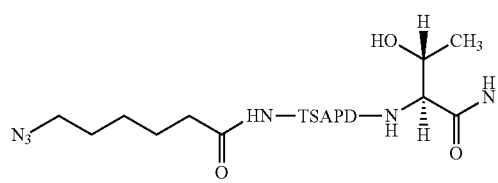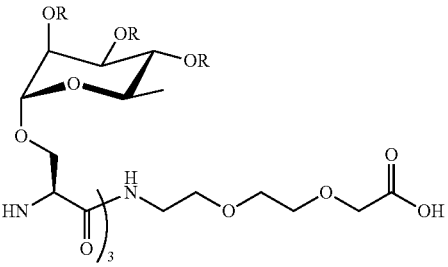

where R=OAc (20) or H (21).

The reaction between the strained alkyne component and the azide component is a cycloaddition, may be a Cu-free cycloaddition.

Though cancer is described for illustrative purposes, the vaccine compositions described herein can be adapted for use as antitumor, antiviral, or antibacterial vaccines, based on the particular antigen(s) included in the compositions. The vaccine compositions can be used to treat, prevent, or ameliorate a wide variety of diseases, determined by the particular antigens present in the composition.

A vaccine composition disclosed herein may comprise different types of carriers depending on whether it is to be administered in solid, liquid, or aerosol form, and whether it needs to be sterile for such routes of administration as injection. Vaccine compositions disclosed herein can be administered intravenously, intradermally, transdermally, intrathecally, intraarterially, intraperitoneally, intranasally, intravaginally, intrarectally, topically, intramuscularly, subcutaneously, mucosally, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, vaccine compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a vaccine composition herein and/or additional agents is formulated to be administered via an alimentary route Alimentary routes include all possible routes of administration in which the composition is in direct contact with the alimentary tract. Specifically, the vaccine compositions disclosed herein may be administered orally, buccally, rectally, or sublingually. As such, these compositions may be formulated with an inert diluent or with an assimilable edible carrier, or they may be enclosed in hard- or soft-shell gelatin capsules, or they may be compressed into tablets, or they may be incorporated directly with the food of the diet.

In further embodiments, a vaccine composition described herein may be administered via a parenteral route. As used herein, the term "parenteral" includes routes that bypass the alimentary tract. Specifically, the vaccine compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the vaccine compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In most cases the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. Sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

Sterile injectable solutions are prepared by incorporating the vaccine compositions in the required amount in the appropriate solvent with various of the other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the vaccine compositions may be formulated for administration via various miscellaneous routes, for example, topical (i.e., transdermal) administration, mucosal administration (intranasal, vaginal, etc.) and/or via inhalation.

Compositions for topical administration may include the vaccine compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the vaccine composition and provide for a homogenous mixture. Transdermal administration of the vaccine compositions may also comprise the use of a "patch." For example, the patch may supply one or more vaccine compositions at a predetermined rate and in a continuous manner over a fixed period of time.

In certain embodiments, the vaccine compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the vaccine compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the vaccine compositions described herein.

The vaccine compositions disclosed herein may also be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age and weight, and the severity and response of the symptoms.

It is further envisioned that the compositions and methods described herein can be embodied in the form of a kit or kits. A non-limiting example of such a kit is a kit for preparing a vaccine composition, the kit comprising Formula II and Formula III in separate containers, where the containers may or may not be present in a combined configuration. Many other kits are possible, such as kits that further include a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive or CD-ROM. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

General Methods 2-chlorotrityl chloride resin was obtained from Chempep Amino acids and HOBt were purchased from Chem-Impex International. All other fine chemicals were from one of the suppliers: Acros Organics, Alfa Aesar, Fisher Scientific, and Sigma-Aldrich. Flash column chromatography was done on silica gel (230-400 mesh) obtained from Sorbent Technologies using solvents as received. $^1$H NMR and $^{13}$C NMR were recorded on a AVANCE 600 MHz spectrometer in CDCl$_{13}$ using residual CHCl$_3$ as an internal reference.

Synthesis of Pam$_3$Cys Tertiary Butyl Ester (2)

Figure 10:
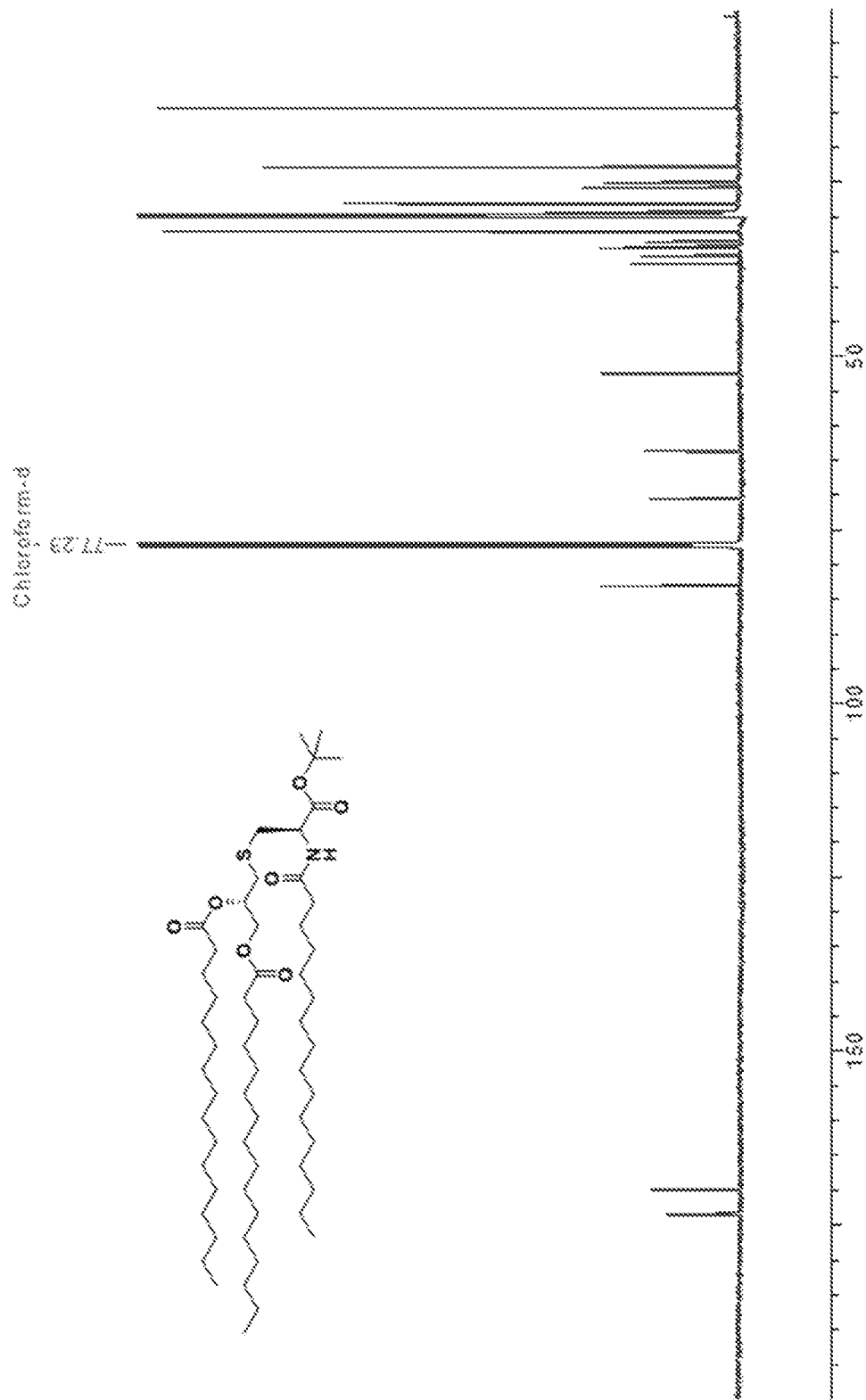
FIG. 10: $^1$H NMR spectrum of Pam$_3$Cys tertiary butyl ester 2.
Figure 11:
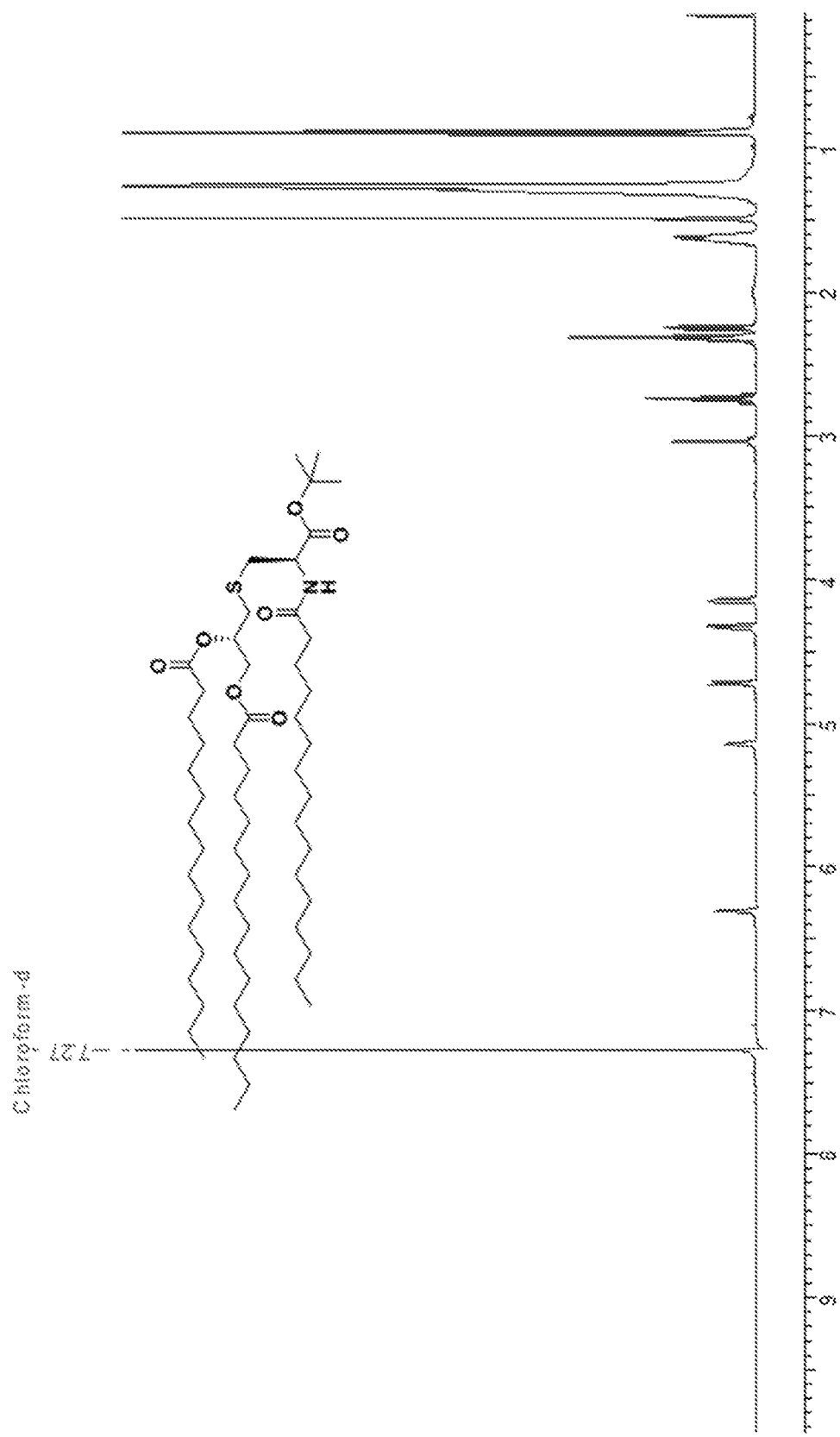
FIG. 11: $^{13}$C NMR spectrum of Pam$_3$Cys tertiary butyl ester 2.

O-palmitoylated Fmoc L-cystine tert-butyl ester (1.55 gm, 1.63 mmol) was dissolved in a mixture of Acetonitrile:DCM:Diethylamine (2:1:2, 10 ml) and stirred under N$_2$ atmosphere at room temperature. Complete Fmoc deprotection was observed on TLC (Hexane: EtOAc, 4:1) after 2 h. The reaction mixture was evaporated to dryness. Palmitic acid (0.5 gm, 1.95 mmol), PyBOP (1.02 gm, 1.95 mmol), and HOBt (264 mg, 1.95 mmol) were dissolved in DCM (20 ml) followed by addition of DIPEA. The reaction mixture was stirred for 10 mins and added to the deprotected compound. The mixture was stirred under N$_2$ atmosphere at RT and observed to be complete after 5 h on TLC (Hexane: EtOAc, 4:1). The crude residue obtained after evaporation of the reaction mixture was purified using silica gel column chromatography using Hexane:EtOAc as a solvent system to obtain 2 as a white solid (1.02 mg, 71.33%). $^1$H NMR (600 MHz, CDCl$_3$): δ0.89 (t, 9H, J=12 Hz Pam-CH$_3$), 1.26-1.65 (m, 78H, Pam-CH$_2$), 1.51 (s, 9H, OtBu-CH$_3$), 2.24-2.34 (m, 6H, J=6 Hz, COCH$_2$), 2.74 (m, 2H, J=6 Hz, S—CH$_2$), 3.03 (dd, 2H, J=6 Hz, S—CH$_2$), 4.12 and 4.32 (dd, 2H, J=12 Hz, CH$_2$—OPam), 4.71 (m, 1H, J=12 Hz, CH—NH), 5.15 (m, 1H, CH—OPam), 6.30 (d, 1H, J=8.4 Hz, Pam-NH). $^{13}$C NMR (600 MHz, CDCl$_3$): δ14-37 (50 C), 52.35, 63.48, 70.30, 82.87, 169.66, 172.92, 173.06, 173.32. ESI-MS [M+Na] m/z: calcd for C$_{58}$H$_{111}$NNaO$_7$S, 988.8; found, 988.6. FIG. 10 shows the $^1$H NMR spectrum of tertiary butyl ester 2, and FIG. 11 shows the $^{13}$C NMR spectrum of tertiary butyl ester 2.

Synthesis of Pam$_3$Cys Carboxylic Acid (3)

Pam$_3$Cys carboxylic acid (3) was synthesized according to Scheme 1 (FIG. 6).

Figure 12:
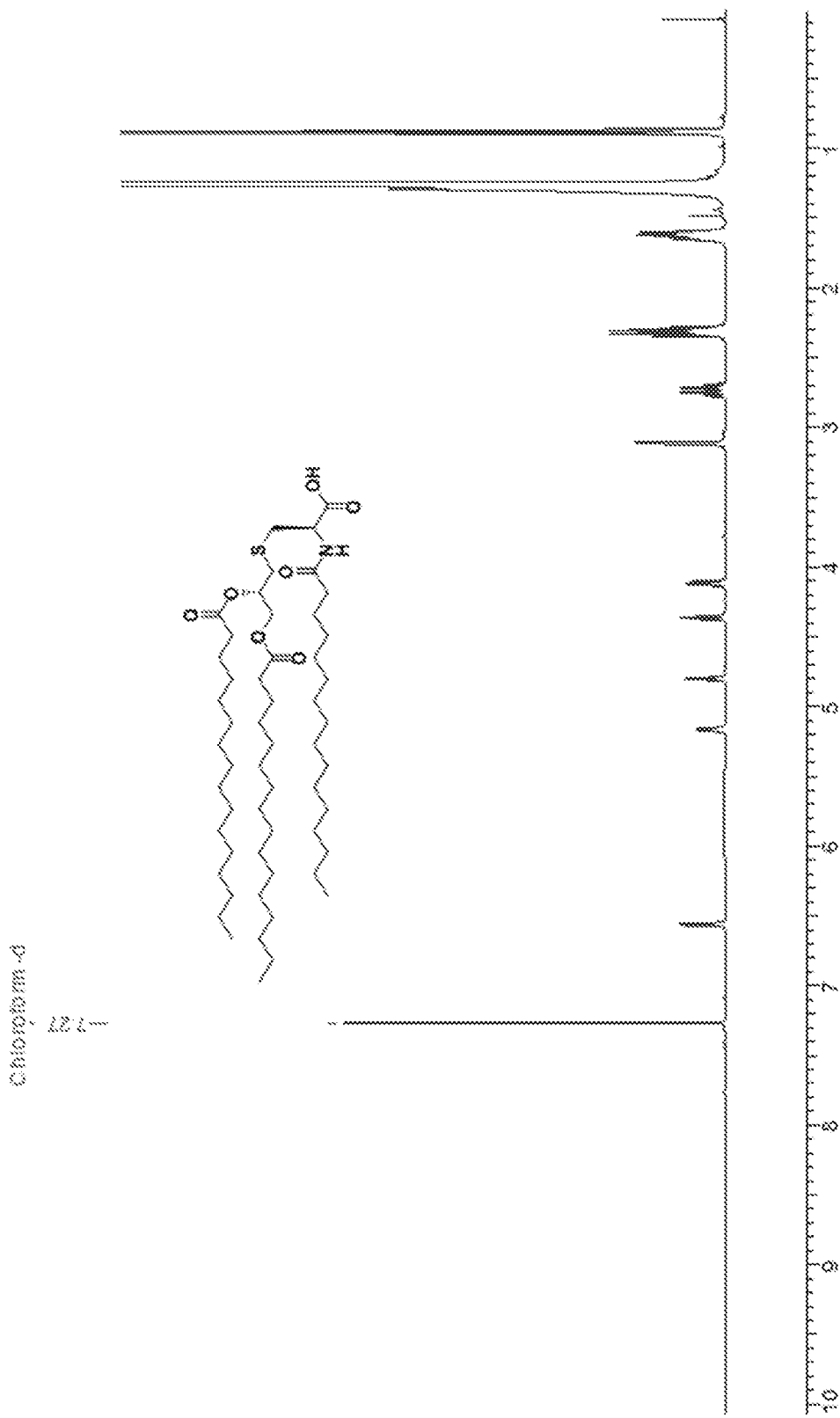
FIG. 12: $^1$H NMR spectrum of Pam$_3$Cys-OH 3.
Figure 13:
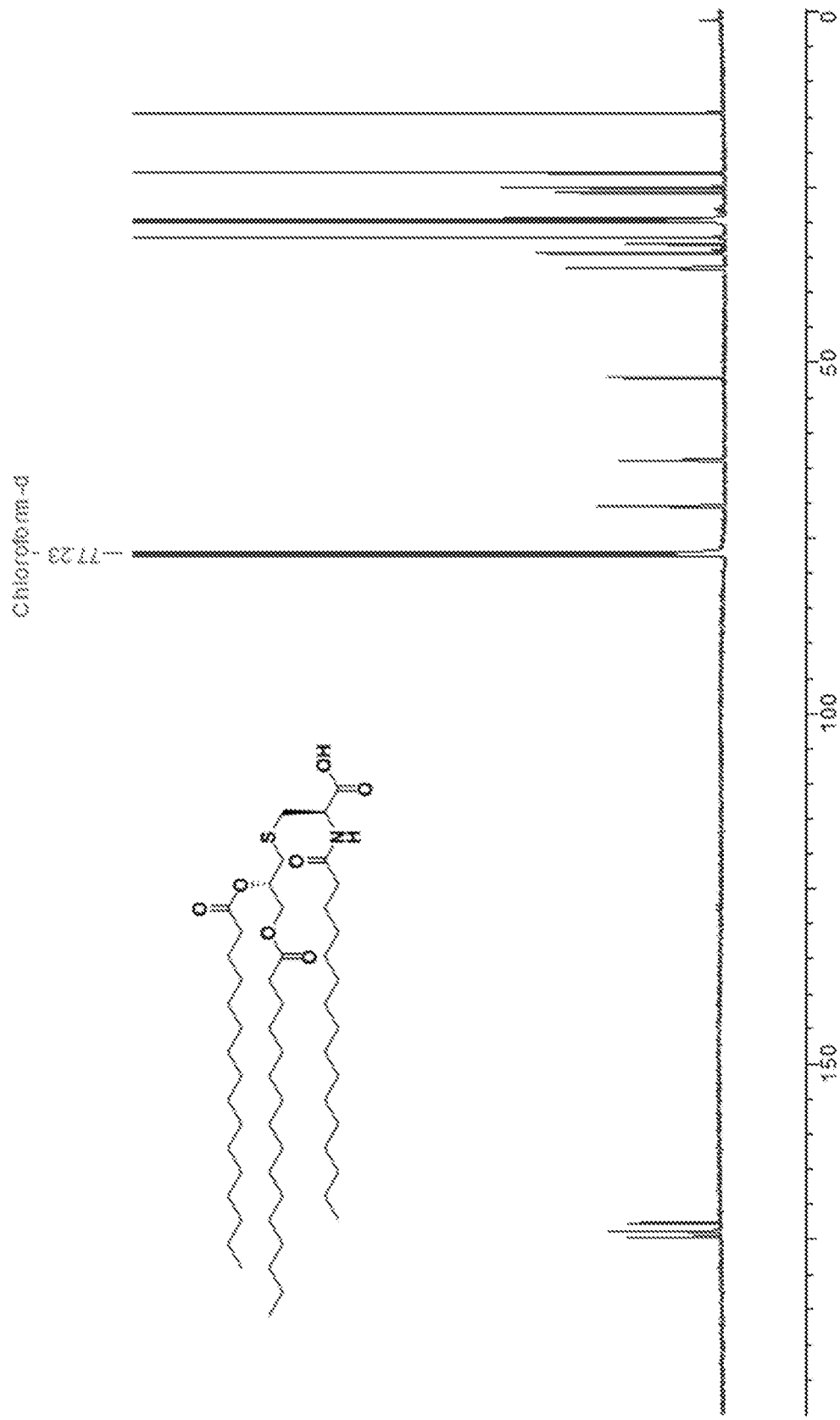
FIG. 13: $^{13}$C NMR spectrum of Pam$_3$Cys-OH 3.
Figure 14:
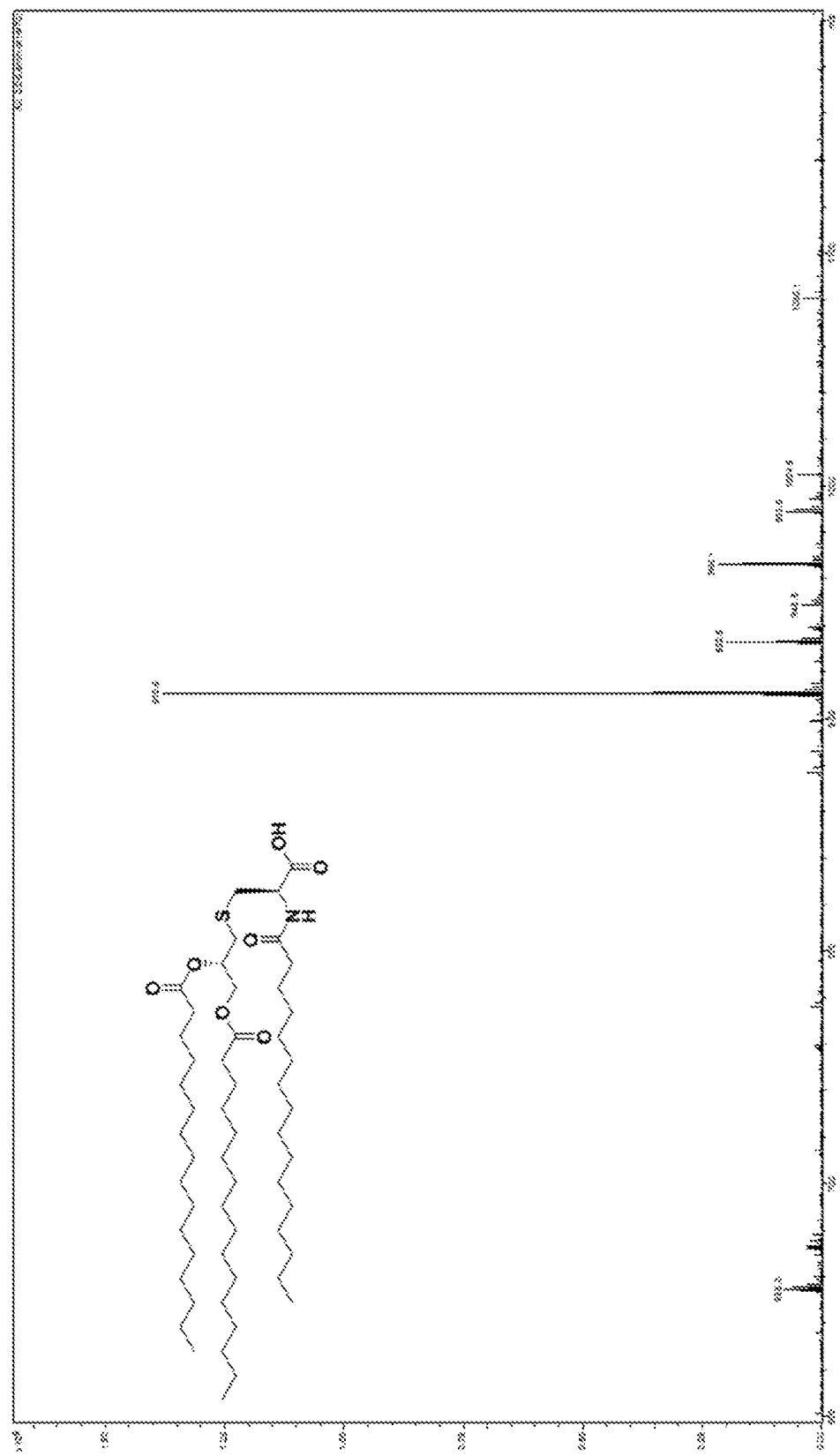
FIG. 14: ESI-MS spectrum of Pam$_3$Cys-OH 3.

Pam$_3$Cys tertiary butyl ester 2 (1.02 gm) was dissolved in a mixture of DCM: TFA (1:1, 4 ml) and stirred under N$_2$ at RT. Complete deprotection was observed on TLC (Hexane:EtOAc, 4:1) after 1 h. The solvent was evaporated on rotary evaporator. DCM:toulene (1:1, 4 ml) mixture was added to the residue multiple times and evaporated to ensure complete removal of TFA and afford compound 3 as a pale white solid (927 mg, quantitative). $^1$H NMR (600 MHz, CDCl$_3$): δ0.89 (t, 9H, J=12 Hz Pam-CH$_3$), 1.26-1.65 (m, 78H, Pam-CH$_2$), 2.24-2.34 (m, 6H, J=6 Hz, COCH$_2$), 2.74 (m, 2H, J=6 Hz, S—CH$_2$), 3.03 (dd, 2H, J=6 Hz, S—CH$_2$), 4.12 and 4.32 (dd, 2H, J=12 Hz, CH$_2$—OPam), 4.71 (m, 1H, J=12 Hz, CH—NH), 5.15 (m, 1H, CH—OPam), 6.30 (d, 1H, J=8.4 Hz, Pam-NH). $^{13}$C NMR (600 MHz, CDCl$_3$): δ14-37 (47 C), 51.9, 63.7, 70.20, 172.46, 173.56, 173.64, 174.43. ESI-MS [M+H] m/z: calcd for C$_{54}$H$_{103}$NO$_7$S, 910.7; found, 910.6. FIG. 12 shows the $^1$H NMR spectrum of Pam3Cys-OH 3, FIG. 13 shows the $^{13}$C NMR spectrum of Pam3Cys-OH 3, and FIG. 14 shows the ESI-MS of Pam$_3$Cys-OH 3.

Synthesis of Pam$_3$CysSK$_4$ (5) ("CysSK$_4$" Disclosed as SEQ ID NO: 16) by Solid Phase Peptide Synthesis (SPPS)

Pam$_3$CysSK$_4$ ("CysSK$_4$" disclosed as SEQ ID NO: 16) was synthesized by Fmoc strategy using solid phase chemistry. 2-chlorotrityl chloride resin was used for SPPS as it is more acid labile and peptide cleavage can be achieved with help of acetic acid:DCM mixture.

The resin beads (0.5 gm) were soaked in DCM (10 ml) overnight. A syringe was used for SPPS, the bottom of which was closed with a filter. A continuous stream of N2 was bubbled from the bottom to agitate the mixture of swollen beads, coupling reagents DIC, HOBt, and Fmoc amino acid residue. According to SPPS protocol, N$_\alpha$-Fmoc-N$_\epsilon$-Boc-L-lysine, Fmoc-O-tert-butyl-L-serine amino acid residue were used to obtain SK$_4$ (SEQ ID NO: 14) peptide bound to resin.

The final coupling was done using Pam$_3$Cys carboxylic acid. Compound 3 (750 mg, 0.825 mmol) was dissolved in a mixture of DCM:DMF (1:1, 4 ml) followed by HOBt (172 mg, 0.825 mmol) and DIC (180 μl, 0.825 mmol). The reaction mixture was added to the SK$_4$ (SEQ ID NO: 14) bound resin suspended in 2 ml of DCM. The resin was agitated for 5 h and appeared complete, which was monitored by Ninhydrin test on resin beads. The beads were washed thoroughly with DMF and DCM to ensure complete removal of un-reacted reagent as well as coupling byproduct.

Figure 15:
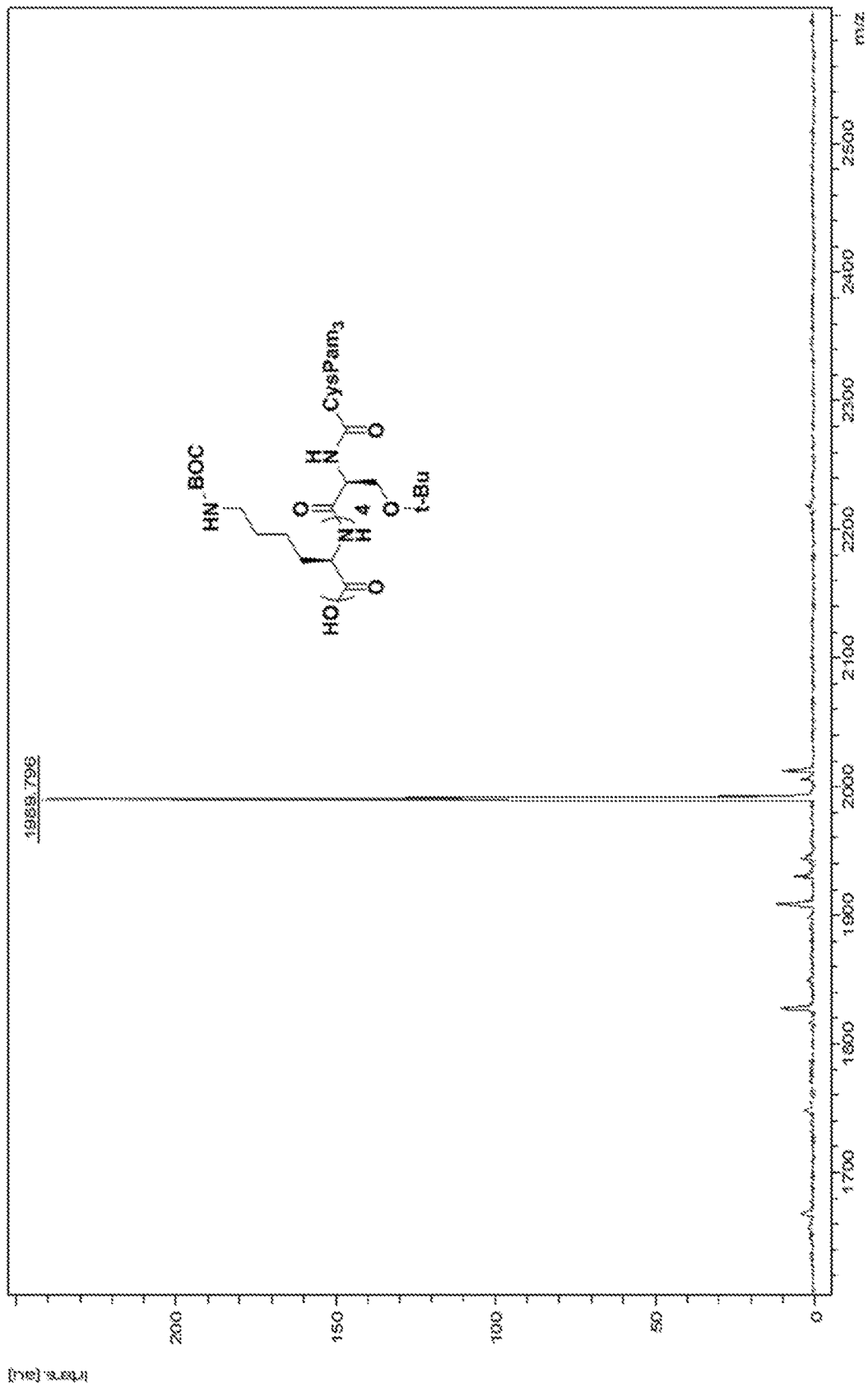
FIG. 15: HRMS spectrum of side-chain protected Pam$_3$CysSK$_4$5 ("CysSK$_4$" disclosed as SEQ ID NO: 16).

The resin beads were suspended in a acetic acid:DCM mixture (1:2, 6 ml) for 2 h and filtered. The mixture was evaporated on a rotary evaporator. DCM:Hexane (1:1, 4 ml) mixture was added to the residue multiple times and evaporated to ensure complete removal of acetic acid and afford compound 5 as a white solid. FIG. 15 shows a HRMS spectrum of side-chain protected Pam$_3$CySSK$_4$5 ("CysSK$_4$" disclosed as SEQ ID NO: 16).

Synthesis of Side-Chain Protected Pam$_3$CysSK$_4$-DBCO Conjugate (6) ("CysSK$_4$" Disclosed as SEQ ID NO: 16)

Figure 16:
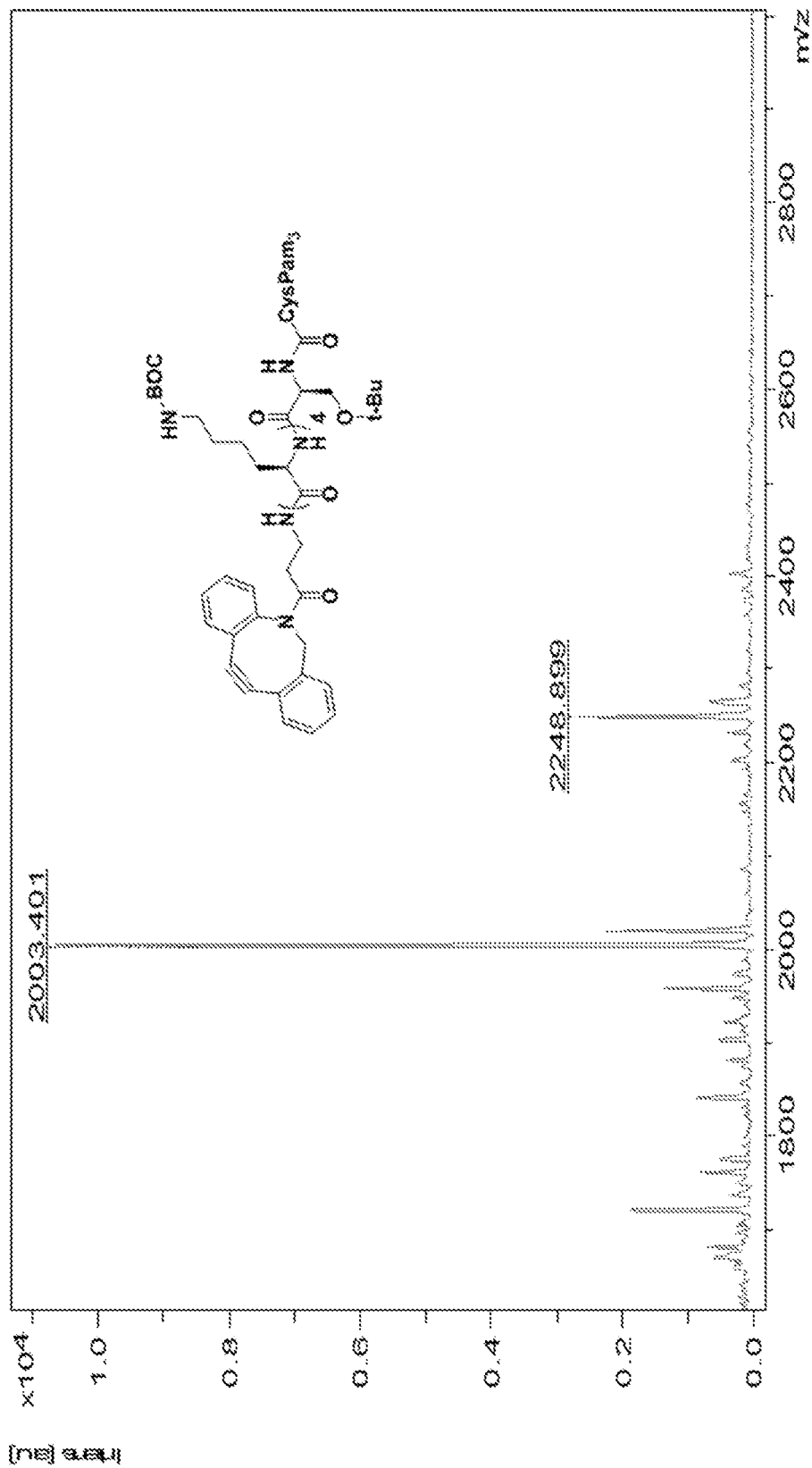
FIG. 16: HRMS spectrum of side-chain protected Pam$_3$CysSK$_4$-DBCO conjugate 6 ("CysSK$_4$" disclosed as SEQ ID NO: 16).

Compound 5 (60 mg, 30 µmol) and DBCO-amine (10 mg, 33 µmol) were dissolved in DCM (4 ml) followed by addition of propylphosphonic anhydride (T$_3$P) (27 µl, 45 µmol) and DIPEA (9 µl, 45 µmol). The reaction mixture was stirred under N$_2$ atmosphere at RT. The reaction was monitored by TLC (CHCl$_3$:EtOH) and appeared complete after 6.5 h. The reaction mixture was diluted with DCM (5 ml) and washed with saturated NaHCO$_3$ (5 ml) and water (5 ml). The organic layer was separated, dried over Na$_2$SO$_4$, and evaporated under reduced pressure. The residue was subjected to silica gel column chromatography (CHCl$_3$:EtOH) to obtain compound 6 as a white powder (33 mg, 50.16%). HR-MALDI-MS: [M+Na] m/z calcd for C$_{123}$H$_{210}$N$_{12}$NaO$_{21}$S, 2248.16; found, 2248.899. FIG. 16 shows the HRMS spectrum of side-chain protected Pam$_3$CysSK$_4$-DBCO conjugate 6 ("CysSK$_4$" disclosed as SEQ ID NO: 16).

Synthesis of Deprotected Pam$_3$CysSK$_4$-DBCO conjugate (7) ("CysSK$_4$" Disclosed as SEQ ID NO: 16)

Figure 17:
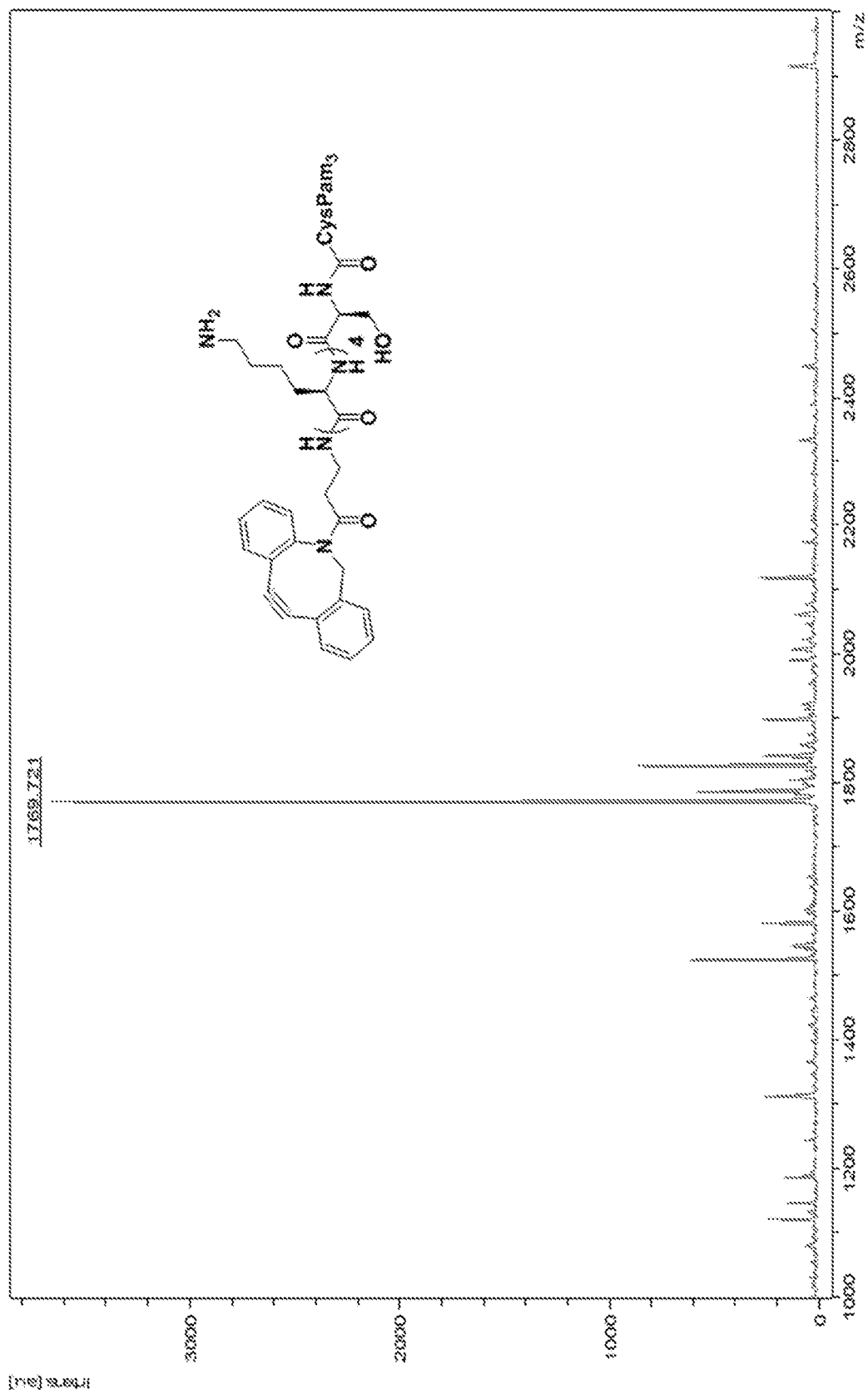
FIG. 17: HRMS spectrum of Pam$_3$CysSK$_4$-DBCO conjugate 7 ("CysSK$_4$" disclosed as SEQ ID NO: 16).

Compound 6 (15 mg, 6.7 µmol) was dissolved in a mixture of DCM:TFA (1:1, 1 ml) and stirred at RT. Complete deprotection was observed after 1 h on TLC (CHCl$_{13}$:EtOH). The TFA was completely evaporated using DCM:Toluene mixture repetitively to afford compound 7 as a pale yellow solid (12 mg, quantitative). HR-MALDI-MS: [M+H] m/z calcd for C$_{99}$H$_{170}$N$_{12}$O$_{13}$S, 1768.27; found, 1768.721. FIG. 17 shows the HRMS spectrum of Pam$_3$CysSK$_4$-DBCO conjugate 7 ("CysSK$_4$" disclosed as SEQ ID NO: 16).

Synthesis of Azide Terminated Peptide (9)

The 20 amino acid-long glycopeptide was synthesized using Fmoc-strategy on wang resin. A similar protocol was followed as described above. HR-MALDI-MS: [M+H] m/z calcd for C$_{100}$H$_{155}$N$_{29}$O$_{37}$, 2355.1172; found, 2355.1753.

Synthesis of Azide Terminated Peptide (10)

Figure 18:
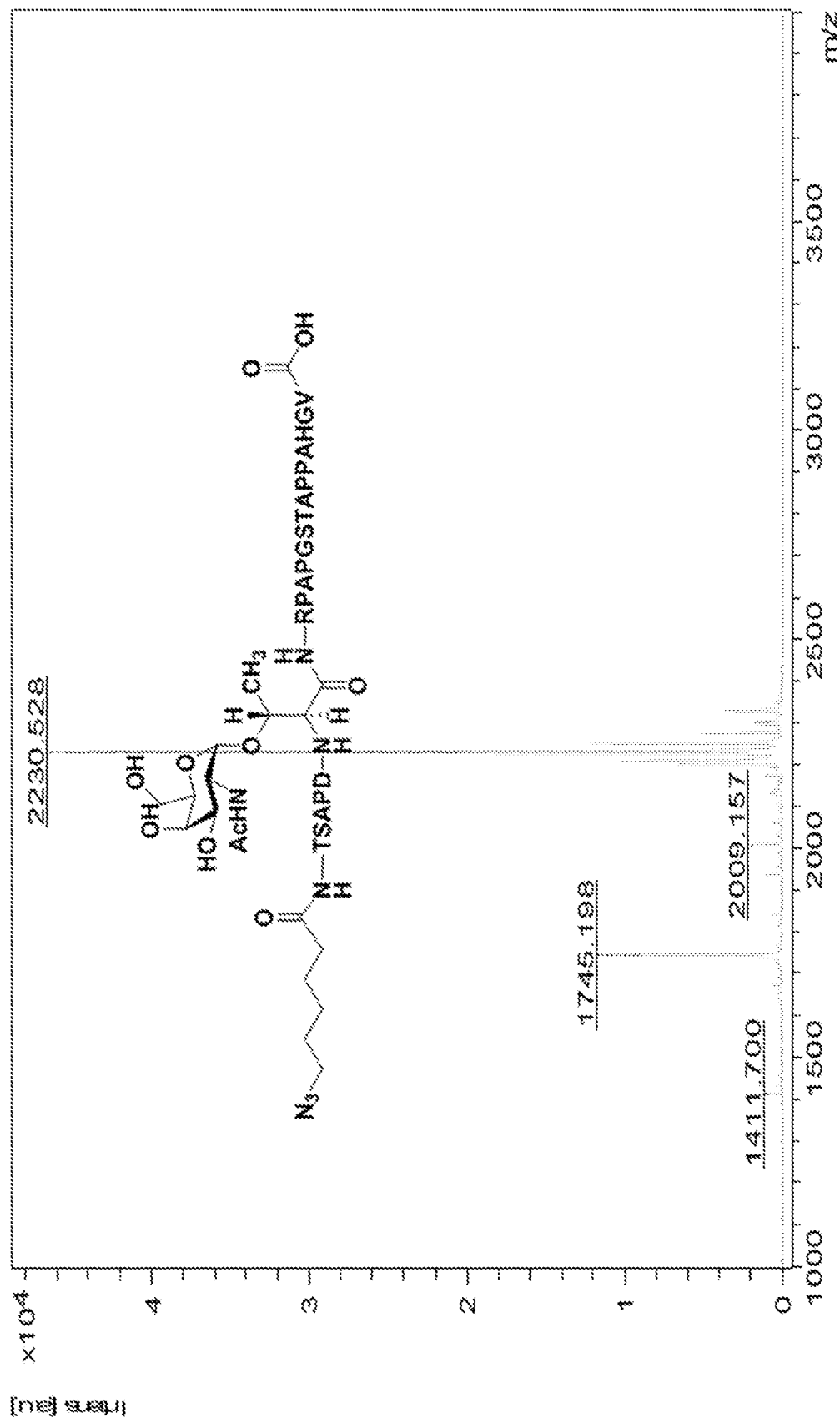
FIG. 18: HRMS spectrum of glycopeptide azide 10.

Compound 9 (4 mg, 1.69 µmol) was dissolved in dry methanol (2 ml) followed by addition of freshly prepared 1 M sodium methoxide (12 µl). The reaction mixture was stirred at r.t. under N$_2$ atmosphere for 3 h. The reaction was neutralized with the help of solid carbon dioxide and concentrated to obtain crude product. The compound was subjected to bio-gel (P-2, 45-90 µm) size exclusion chromatography with deionized water as the solvent. Lyophilisation of eluents afforded compound 10 (3.7 mg, quantitative). HR-MALDI-MS: [M+H] m/z calcd for C$_9$H$_{149}$N$_{29}$O$_{34}$, 2229.0895; found 2230.0959. FIG. 18 shows the HRMS spectrum of glycopeptide azide 10.

Synthesis of Glycopeptide (11)

Figure 19:
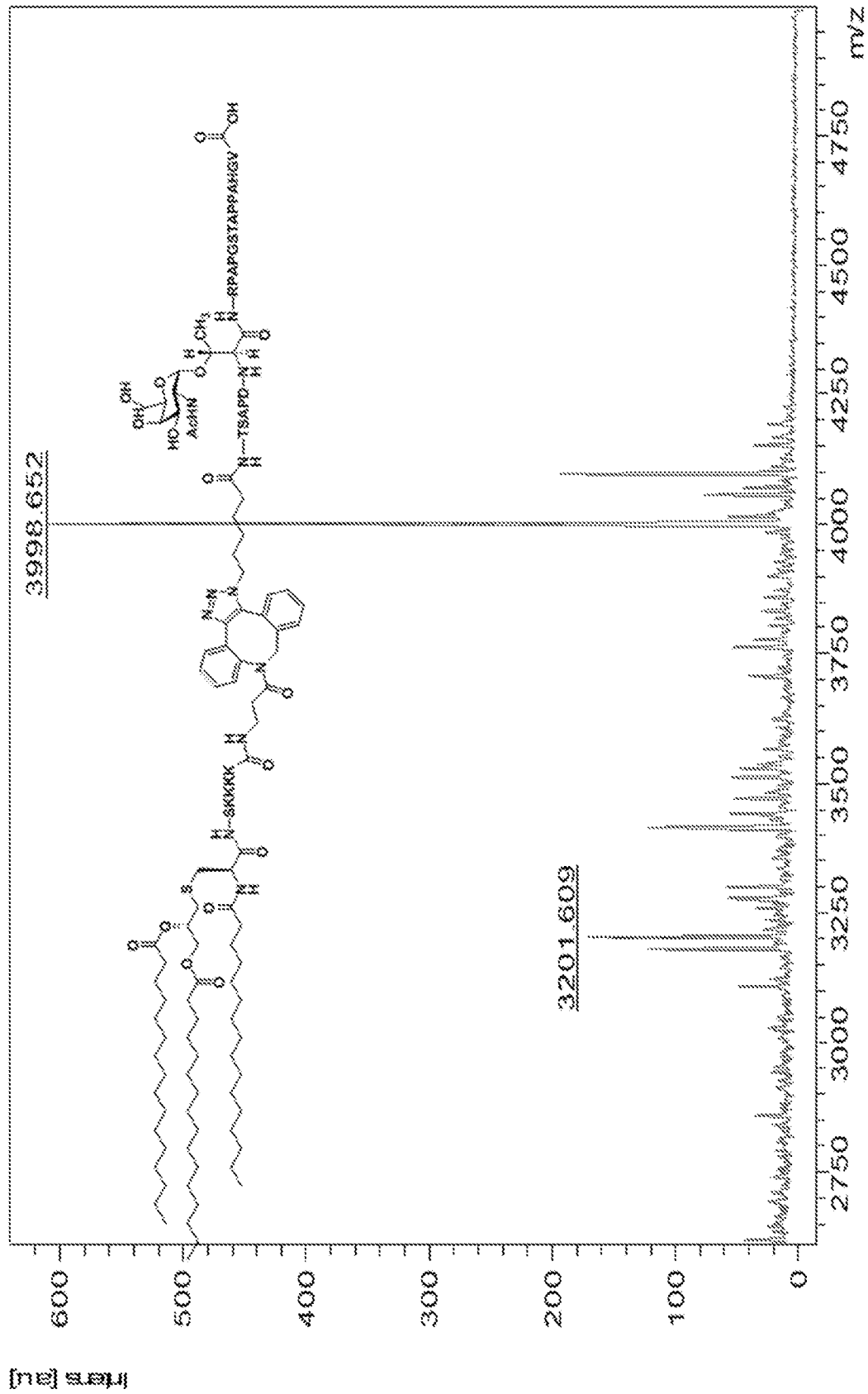
FIG. 19: HRMS spectrum of Pam$_3$CysSK$_4$-DBCO-MUC-1 VNTR-TACA conjugate 11 ("CysSK$_4$" disclosed as SEQ ID NO: 16).

Compound 7 (1 mg, 0.56 µmol) and azide terminated peptide 10 (1.4 mg, 0.62 µmol) were dissolved in a mixture of DCM:anhydrous MeOH (1:1, 1 ml). The reaction mixture was stirred under N$_2$ atmosphere at RT. Complete consumption of starting material was observed on MALDI along with the m/z peak of cyclo-addition product after 12 h. The reaction mixture was concentrated. The residue was dissolved in CHCl$_3$ (3 ml) and washed with water (2 ml). The organic layer was dried over Na$_2$SO$_4$ and evaporated under reduced pressure to obtain cyclo-addition product 11 as pale yellow solid (2.1 mg, quantitative). FIG. 19 shows the HRMS spectrum of Pam$_3$CysSK$_4$-DBCO-MUC-1 VNTR-TACA conjugate 11 ("CysSK$_4$" disclosed as SEQ ID NO: 16).

Synthesis of Adjuvant Pathogenic Diabetic Peptide Conjugate (13)

Figure 20:
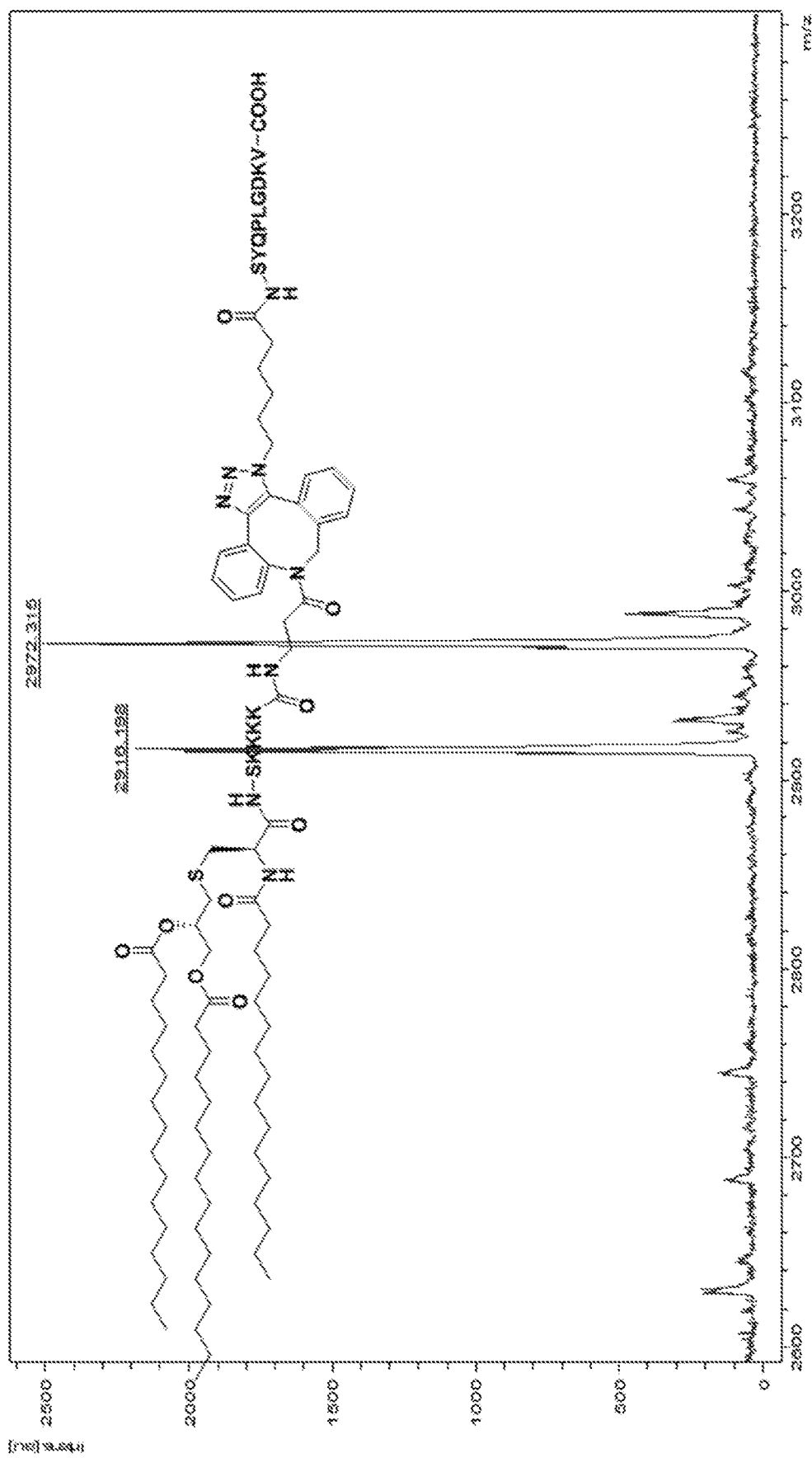
FIG. 20: HRMS spectrum of Pam$_3$CysSK$_4$-DBCO-pathogenic diabetic peptide 13 ("CysSK$_4$" disclosed as SEQ ID NO: 16).

The same synthetic procedure was followed as that for 11. Compound 7 (3 mg, 1.6 µmol) and 12 (2 mg, 1.74 µmol) were conjugated to afford compound 13 as a pale white solid (4.8 mg, quantitative). FIG. 20 shows the HRMS spectrum of Pam$_3$CysSK$_4$-DBCO-pathogenic diabetic peptide 13 ("CysSK4" disclosed as SEQ ID NO: 16).

Synthesis of (17)

To a solution of 16 (1.2 g, 3.6 mmol) in anhydrous DCM (20 mL), BF$_3$.OEt$_2$ (0.54 mL, 4.3 mmol) and p-thiocresol (0.67 g, 5.4 mmol) were added at 0° C. The reaction was stirred under N$_2$ atmosphere at room temperature for 15 h. The reaction was monitored by TLC and a new spot was observed. The mixture was diluted with DCM (20 mL) and washed with aq. NaHCO$_3$ (10 mL), brine solution (10 mL), and water (10 mL). The organic layer was collected and dried over anhydrous sodium sulfate. The solvent was evaporated and the crude product was subjected to silica gel flash column chromatography (Hex:EtOAc, 8:2) to afford desired product as colorless oil 17 (1.133 g, 79.15%). NMR (600 MHz, CDCl$_3$): δ1.24 (d, J=6.24 Hz, 3H), 2-2.14 (s, 9H), 2.33 (s, 3H), 4.37 (m, 1H), 5.14 (t, J=9.9 Hz, 1H), 5.28-5.48 (m, 2H), 5.49 (d, J=1.5 Hz, 1H), 7.12 (d, J=7.92 Hz, 2H), 7.36 (d, J=8.1 Hz, 2H); $^{13}$C NMR (600 MHz, CDCl$_3$): δ17.53, 20.91, 21.14, 21.35, 67.88, 69.57, 71.38, 71.48, 86.23, 129.57, 130.17, 132.66, 138.43, 170.15, 170.25.

Synthesis of Rhamnose-Serine (18)

Figure 21:
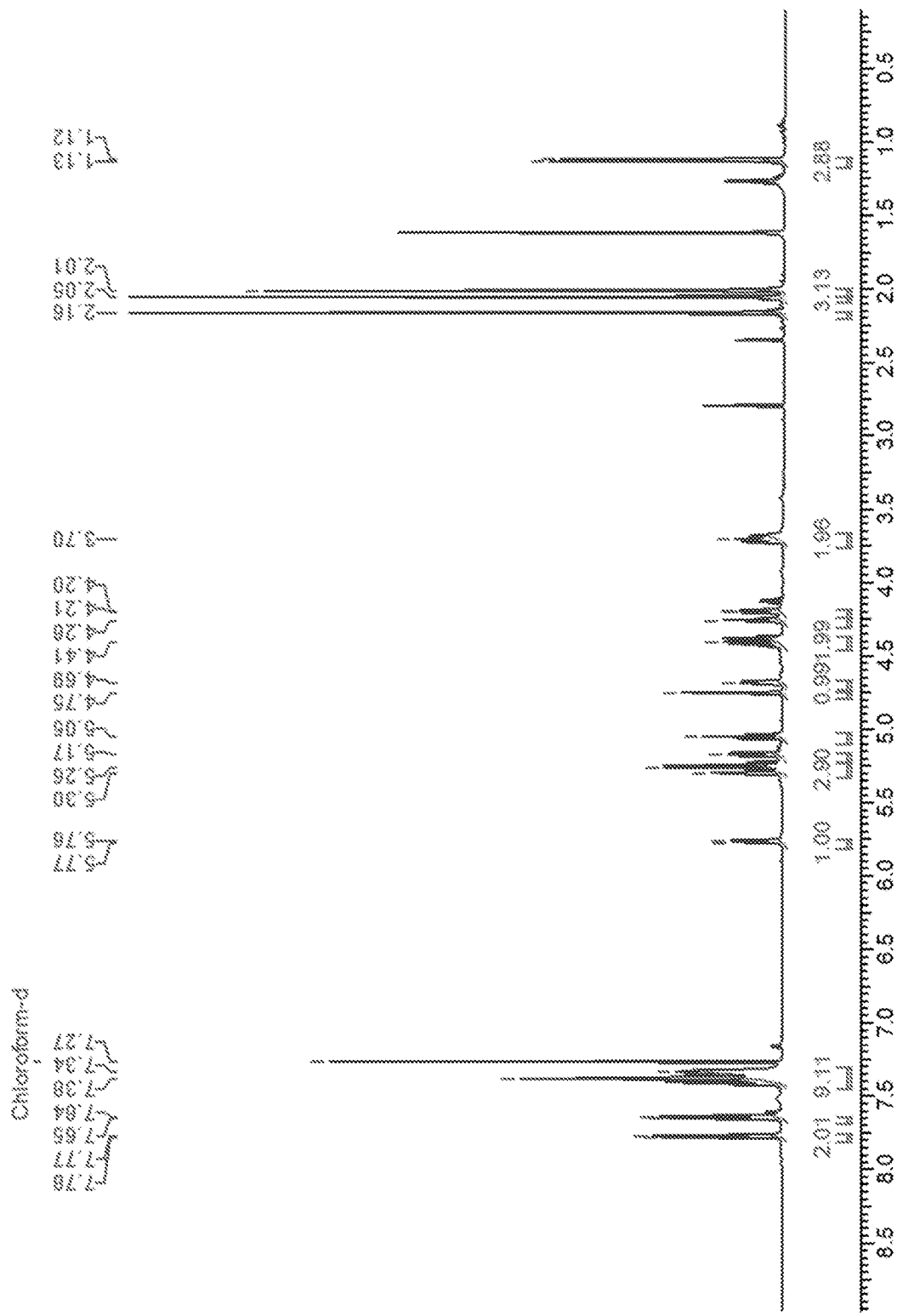
FIG. 21: $^1$H NMR spectrum of protected Rhamnose-Serine (protected) (18).
Figure 22:
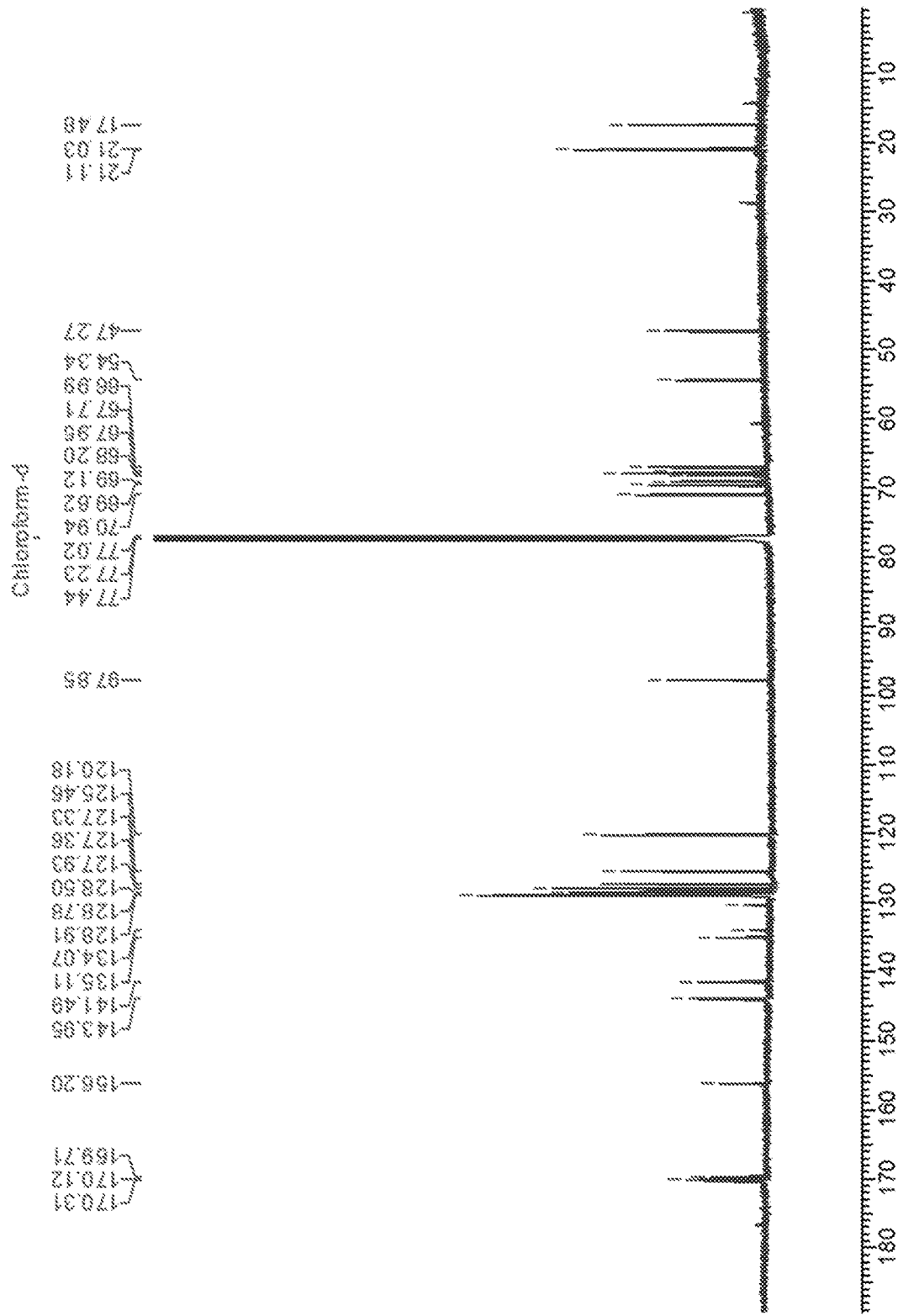
FIG. 22: $^{13}$C NMR spectrum of protected Rhamnose-Serine (protected) (18).

Compound 17 (1.5 g, 3.78 mmol) and Fmoc-Ser-OBn (1.44 g, 3.44 mmol) were dissolved in anhydrous DCM (22 mL) and stirred for 30 mins with 3 Å molecular sieves (150 mg) under N2 atmosphere at room temperature. NIS (1.16 g, 5.1 mmol) and TMSOTf (210 µl, catalytic) were added and the reaction monitored by TLC. After 2.5 h, the reaction appeared complete. The reaction was diluted with DCM (25 mL) and filtered through Celite. The filtrate was washed with aq. NaHCO$_3$ (20 mL), brine solution (10 mL), and water (10 mL). The organic layer was separated, dried over anhydrous sodium sulfate, and subjected to silica gel flash column chromatography (Hex:EtOAc, 8:2) to afford product 18 as white solid 16 (1.8 g, 70%). $^1$H NMR (600 MHz, CDCl$_3$): δ1.12 (d, J=6.18 Hz, 3H), 2-2.17 (s, 9H), 3.71 (m, 2H), 4.20 (dd, J=9.9, 2.94 Hz, 1H), 4.26 (t, J=7.26 Hz, 1H), 4.40 (m, 2H), 4.67 (d, J=8.64 Hz, 1H), 4.75 (s, 1H), 5.05 (t, J=9.9 Hz, 1H), 5.17 (dd, J=10.08, 3.42 Hz, 1H), 5.28 (m, 2H), 5.77 (d, J=8.64, 1H), 7.3-7.8 (m, 13H); $^{13}$C NMR (600 MHz, CDCl$_3$): δ17.48, 21.03, 21.11, 47.27, 54.34, 66.99, 67.71, 67.95, 98.2, 69.12, 69.62, 70.94, 97.85, 120.18, 125.46, 127.33, 127.393, 128.5, 128.78, 128.91, 134.07, 135.11, 141.49, 143.95, 156.20, 169.71, 170.12, 170.31. ESI-MS [M+Na] m/z: calcd for C$_{37}$H$_{39}$NNaO$_{12}$, 712.70; found, 712.50. The $^1$H NMR spectrum of Rhamnose-Serine (protected) (18) is shown in FIG. 21, and the $^{13}$C NMR spectrum of protected Rhamnose-Serine (protected) (18) is shown in FIG. 22.

Synthesis of Rhamnosyl-Serine (19)

Figure 23:
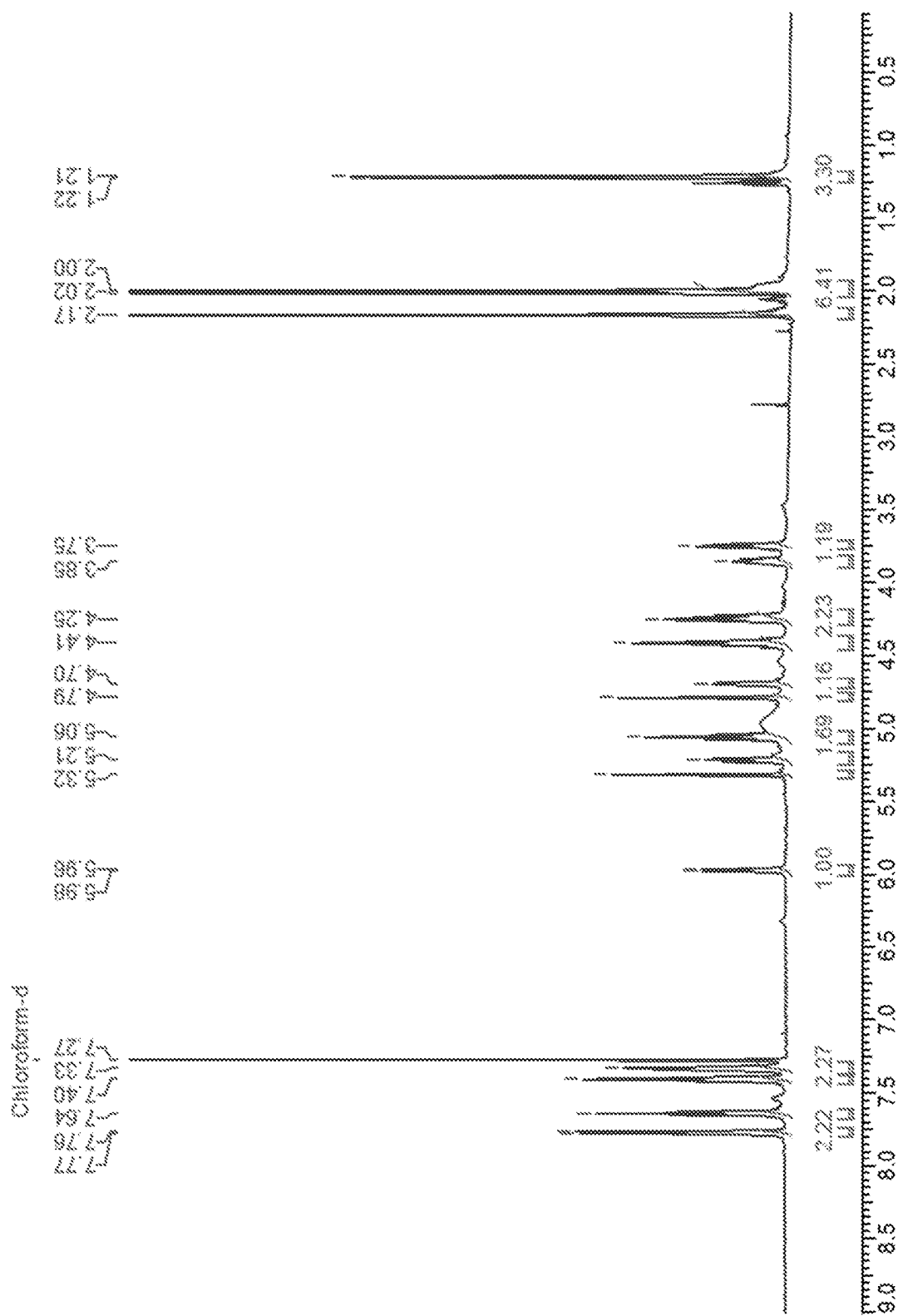
FIG. 23: $^1$H NMR spectrum of Rhamnose-Serine (deprotected) (19).
Figure 24:
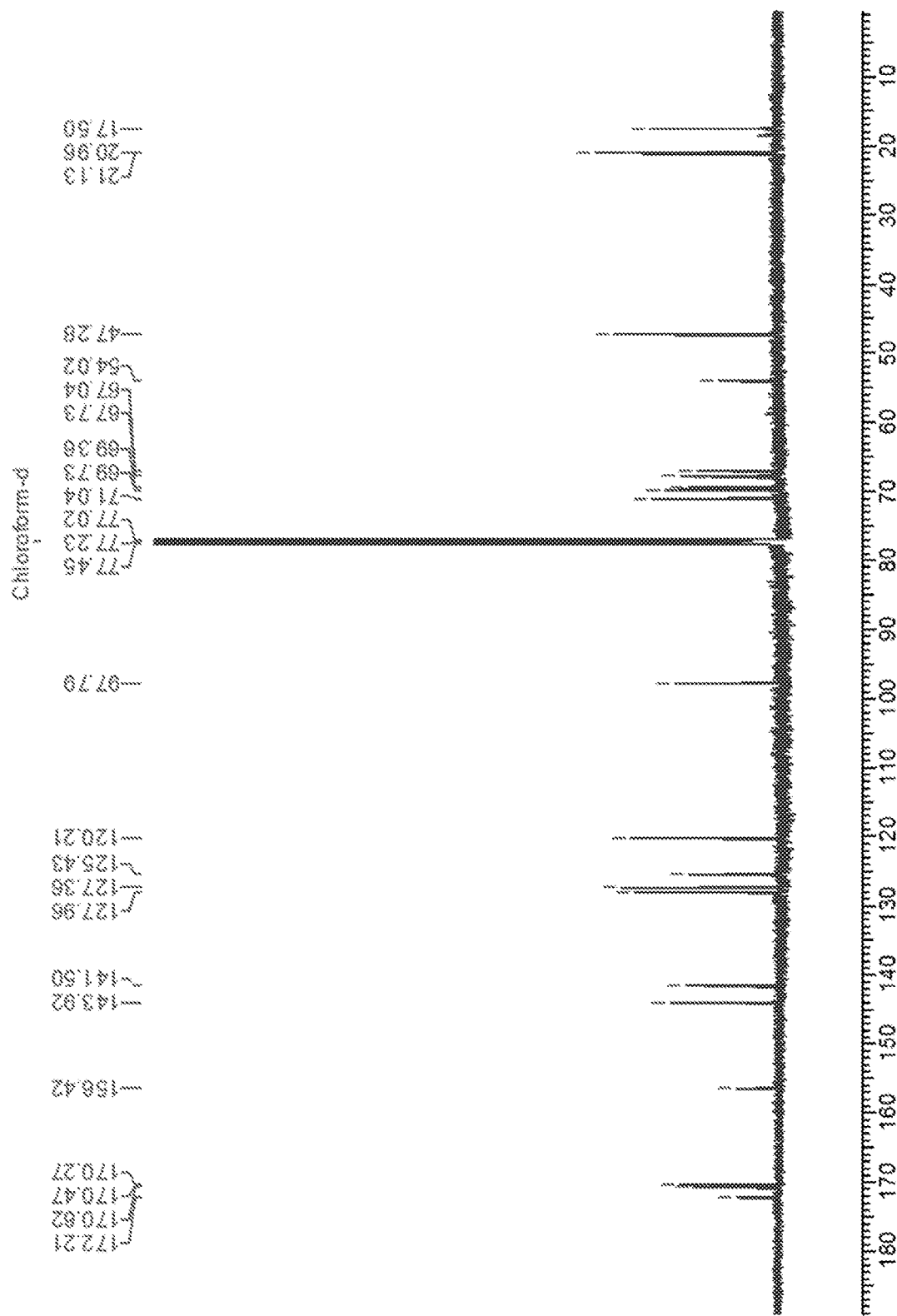
FIG. 24: $^{13}$C NMR spectrum of protected Rhamnose-Serine (deprotected) (19).

Pd/C, 20% Pd (500 mg) was added to a solution of 18 (1.6 g, 2.3 mmol) in anhydrous MeOH (20 mL). The reaction was stirred under 1 atm H2 at room temperature for 2.5 h. The solution was filtered through Celite and the filtrate was evaporated to obtain a crude product. The product was subjected to silica gel flash column chromatography (CHCl$_3$:EtOH) to obtain product 19 as white foamy solid (0.778 mg, 74.8%). 400 mg of starting material 18 was also recovered. $^1$H NMR (600 MHz, CDCl$_3$): δ1.22 (d, J=6.18 Hz, 3H), 1.98-2.16 (s, 9H), 3.74 (m, 1H), 3.85 (m, 1H), 4.25 (m, 2H), 4.41 (t, J=6.24 Hz, 1H), 4.68 (d, J=8.34 Hz, 1H), 4.78 (s, 1H), 5.05 (t, J=9.96 Hz, 1H), 5.22 (dd, J=10.08, 3.18 Hz, 1H), 5.31 (m, 1H), 5.96 (d, J=8.4 Hz, 1H), 7.26-7.78 (aromatic 8H); $^{13}$C NMR (600 MHz, CDCl$_3$): δ17.5, 20.96, 21.13, 47.28, 54.02, 67.04, 67.73, 69.36, 69.73, 71.04, 97.79, 120.21, 125.43, 127.36, 127.96, 141.5, 143.92, 156.42, 170.27, 170.47, 170.62, 172.21. HRMS [M+Na] m/z: calcd for C$_{30}$H$_{33}$NNaO$_{12}$, 622.19; found, 622.1903. The $^1$H NMR spectrum of Rhamnose-Serine (deprotected) (19) is shown in FIG. 23, and the $^{13}$C NMR spectrum of protected Rhamnose-Serine (deprotected) (19) is shown in FIG. 24.

Synthesis of Azido-Functionalized Xenoantigen-Containing Peptide (20)

An azido functionality was appended to the N-terminus of the peptide as a chemical handle for copper-free azide-alkyne conjugation with 7. The 20 amino acid sequence, N$_3$-linker-TSAPDTRPAPGSTAPPAHGV(Ac$_3$αRhaSer)$_3$NH(CH$_2$CH$_2$O)$_4$CH$_2$CH$_2$COOH (20) (SEQ ID NO: 13), was synthesized according to Scheme 7 (FIG. 9C). The protected azide-containing peptide was prepared by the Fmoc-strategy on an automated peptide synthesizer using solid phase chemistry. The coupling of the amino acids, the acetyl protected FmocNH-Ac$_3$αRhaSer-OH 19, and the azide functionality was achieved by HOBt and DIC in the presence of NMP starting with a preloaded H-mini-PEG-2-ClTrt-Resin. Fmoc deprotections were accomplished by treatment with 25% piperidine in dimethylformamide A modified Reagent K cocktail consisting of 88% TFA, 3% thioanisole, 5% ethanedithiol, 2% water, and 2% phenol was used for simultaneous resin cleavage and deprotection of the glycopeptide. The acetyl protections on the N-acetyl galactal survived the cleavage conditions. At the end of cleavage, the cocktail mixture was filtered through a Quick-Snap and collected in 20 mL ice-cold butane ether. The peptide was allowed to precipitate for an hour at −20° C., centrifuged, and washed twice with ice-cold methyl-t-butyl ether. The precipitate was dissolved in 25% acetonitrile and lyophilized to complete dry powder affording peptide 20. The quality of the peptides was analyzed by analytical reverse phase HPLC and TOF-MS-ES. The acetyl deprotection was achieved by treating the azidopeptide 20 with 6 mM sodium methoxide in methanol. The deprotected peptide 21 was purified by size exclusion chromatography using Bio-Gel (P-2, 45-90 μm) and water as solvent followed by lyophilization.

Figure 25:
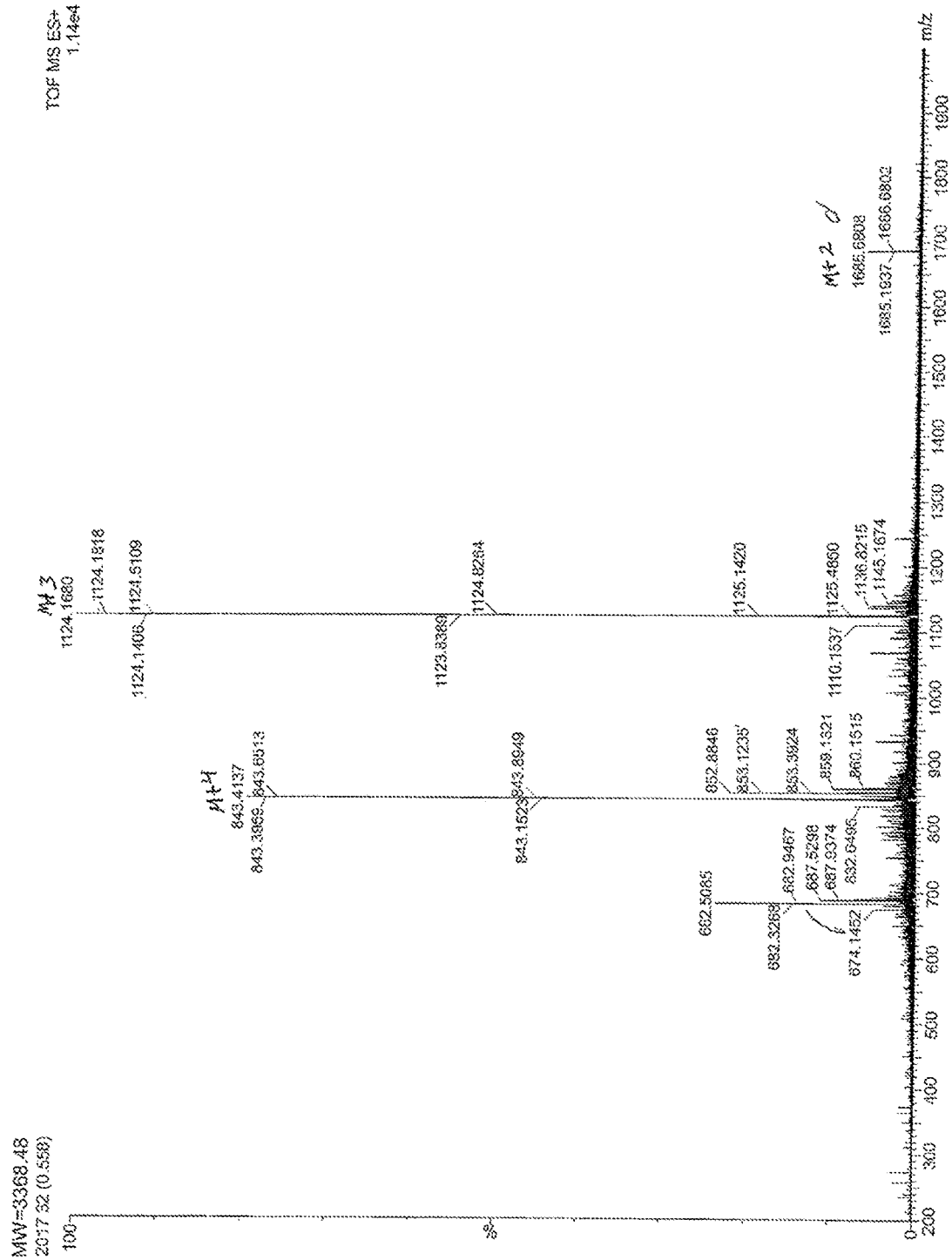
FIG. 25: Mass spectrum of lipoglycopeptide (22).

FIG. 25 shows the mass spectrum of lipoglycopeptide 22.

Vaccine Formulations

Stock solutions were prepared of 1,2-dipalmitoyl-sn-glycero-3-phosphocholine (DPPC), cholesterol, 1,2-distearoyl-sn-glycero-3-phosphoethanolamine-N-[maleimide(polyethylene glycol)-2000] (ammonium salt) (DSPE-PEG-MAL), and Rha-TEG-cholesterol. Aliquots from the stock solution were mixed to obtain a lipid solution of 30 mM in a total volume of 1 mL.

Formulation I: Lipopeptide conjugate (0.2 μmoles), DPPC (80%), cholesterol (20%), and DSPE-PEG-MAL (1% by wt.) were formulated in to liposomes by the extrusion method with 100 nm polycarbonate membrane. To a solution of 50 ug anti-F4/80 antibody in phosphate buffer, (succinimidyl 3-(2-pyridyldithio)propionate) (SPDP) was added (20 mM in ethanol, SPDP: antibody 20:1 molar ratio) and left for about half an hour at RT. Excess of SPDP was removed by using Sephadex G50 spin columns. To the filtrate, dithiothreitol (DTT) was added to make 15 mM final solution. The mixture was left at room temperature for 0.5 h to obtain thiolated antibody. The antibody was again subjected to gel filtration on a G50 column to remove excess DTT. The freshly reduced and thiolated antibody solution was added to the liposomes containing DSPE-PEG-MAL (1% by wt.). The mixture was stirred overnight at RT. Liposomal pellet was centrifuged down, washed twice with PBS buffer, and resuspended in the desired volume of PBS buffer for injections.

Formulation II: Lipopeptide conjugate (0.2 μmoles), cholesterol-TEG-Rha (10%), cholesterol (10%), and DPPC (80%) were formulated into liposomes by the extrusion method with 100 nm polycarbonate membrane.

Use of Antibodies to Enhance Vaccine Immunogenicity

Utilizing natural antibodies to augment vaccine immunogenicity is an effective approach for cancer immunotherapy. Anti rhamnose antibody is among the most common natural anti-carbohydrate antibodies present in human serum. Therefore, rhamnose can be utilized as a targeting moiety for a rhamnose containing vaccine to prepare an effective vaccine formulation. Binding rhamnose of a rhamnose-containing vaccine with anti-rhamnose antibody has been proven effective for capturing and processing of antigen by antigen presenting cells (APC) via stimulatory Fc receptors. This was shown using anti-rhamnose antibodies generated in mice. Human anti-rhamnose antibodies isolated from human serum work in a similar manner.

To isolate anti-rhamnose antibodies, a rhamnose affinity column with a rhamonse-2 amino ethyl linker conjugate coupled to CNBr-activated Sepharose was prepared. In-vivo, injection of human anti-rhamnose antibodies into mice improved the priming of helper T cells to a rhamnose-modified MUC1-Tn-liposomal anti-cancer vaccine and increased anti-MUC1-Tn antibody production. Both CD4+ and CD8+ T cells demonstrated increased responses toward the MUC1-Tn cancer antigen when mice were given human anti-rhamnose antibodies prior to vaccination. Other human immunoglobulins did not enhance priming Therefore, human anti-rhamnose antibodies can enhance immune responses to rhamnose-containing vaccines through increased antigen uptake and presentation.

Figure 26A:
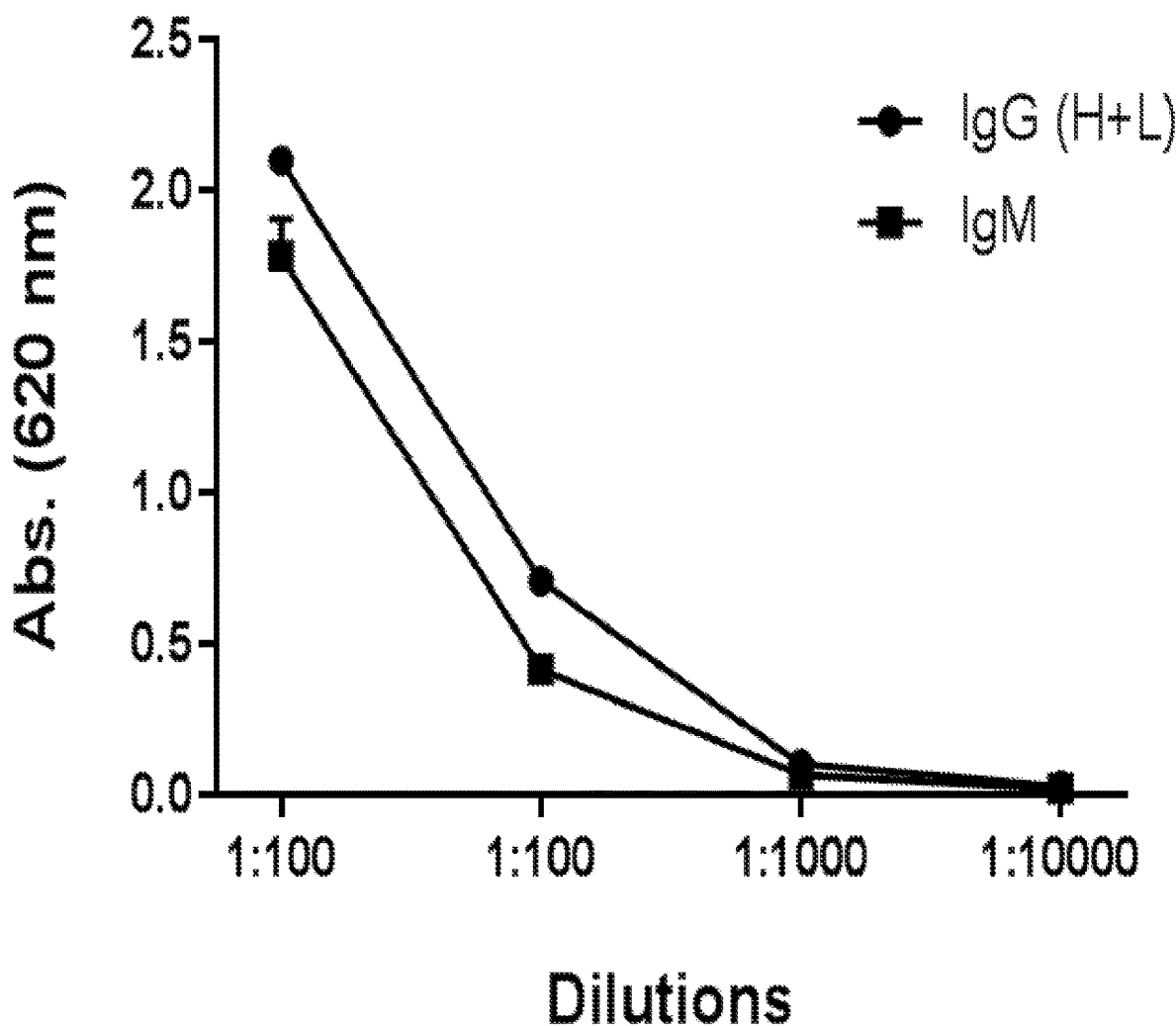
FIGS. 26A-26D: Purification and characterization of human anti-rhamnose antibodies.
Figure 26B:
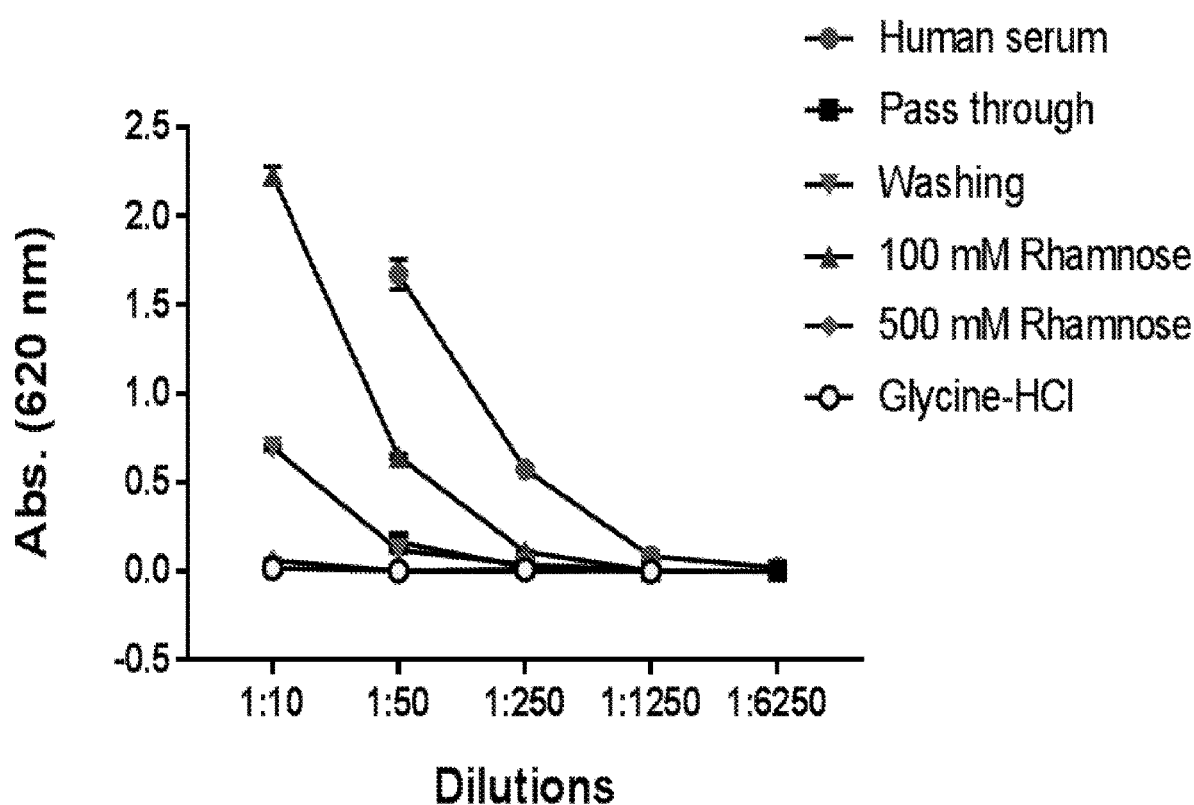
Figure 26C:
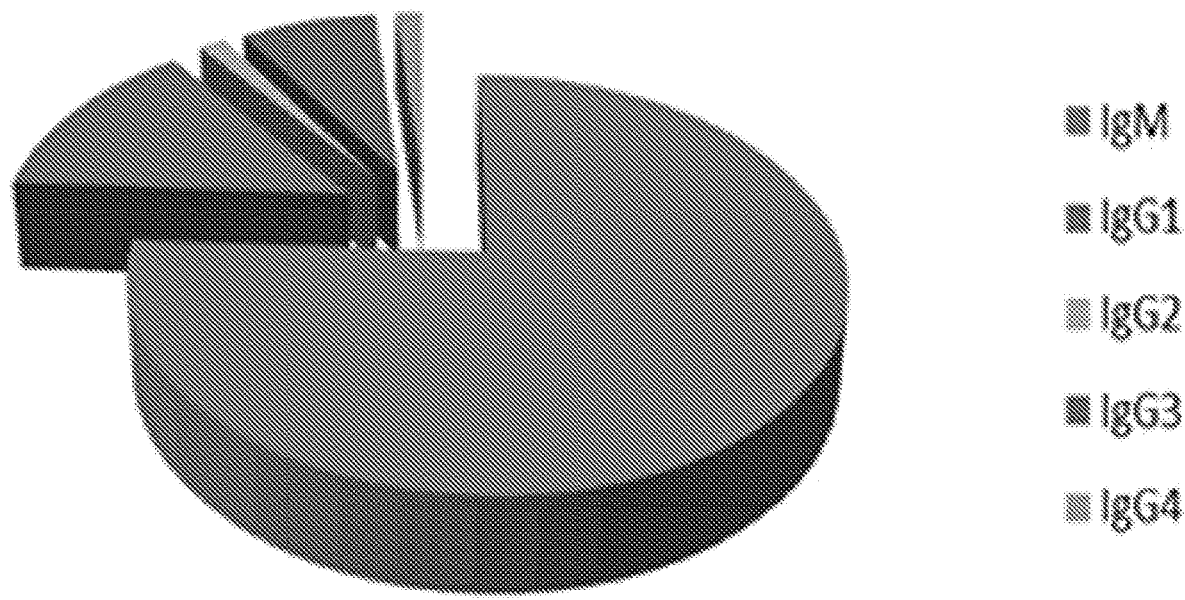
Figure 26D:
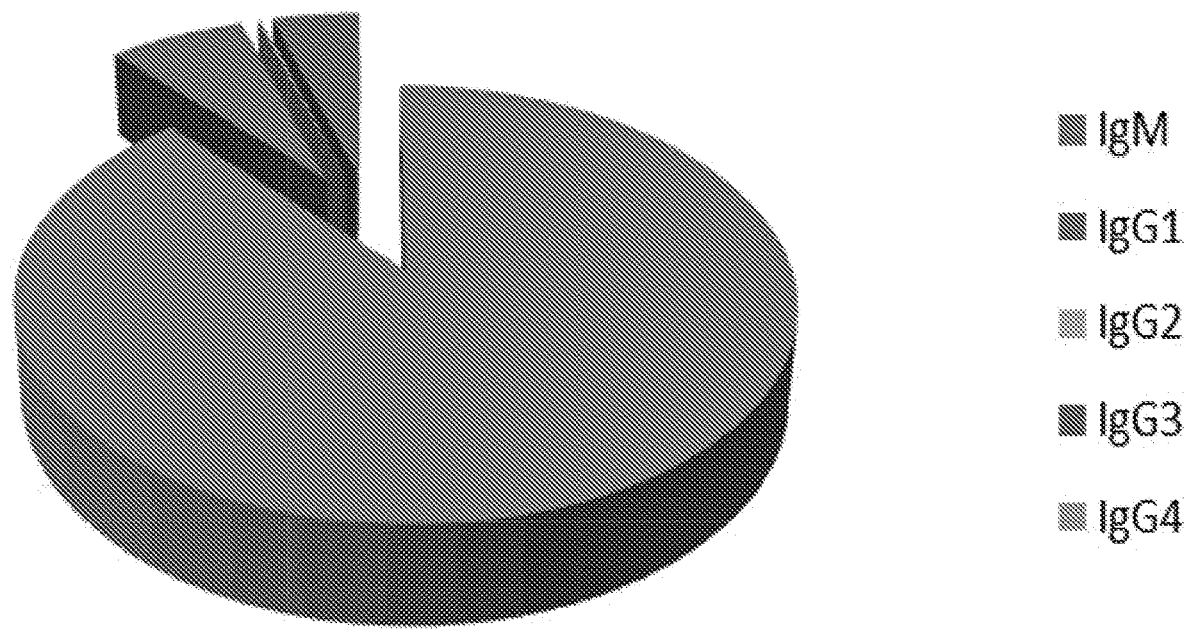

FIGS. 26A-26D show purification and characterization of human anti-rhamnose antibodies. FIG. 26A shows a graph of commercially pooled human serum with Rha-specific ELISA to determine the concentration of anti-rhamnose antibody in serum. FIG. 26B shows a graph of rhamnose specific ELISA with different fractions from the Rha-affinity column showing the presence of anti-rhamnose antibodies in each. Most of the purified anti-rhamnose antibodies were eluted with 100 mM rhamnose solution. The pass through contained no anti-rhamnose activity. FIG. 26C shows natural anti-Rha antibodies found in human serum are mostly IgM and IgG1 and 3. FIG. 26D shows purified anti-Rha antibody also reflects this distribution.

Figure 27A:
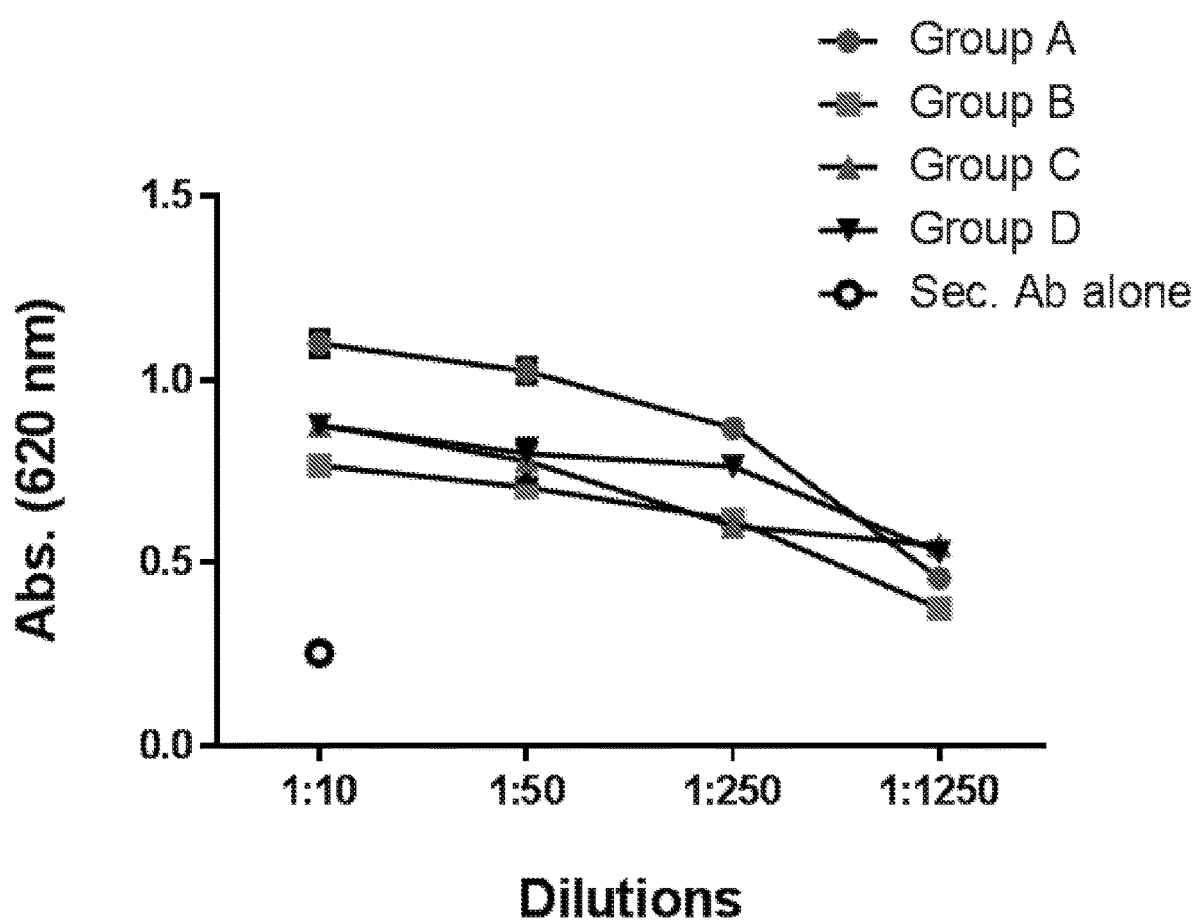
FIGS. 27A-27C: In-vivo enhancement of anti-MUC1-Tn response by human anti-rhamnose antibodies. Group A is Anti-Rha+Rha-Pam$_3$CysSK$_4$-MUC1-Tn ("CysSK$_4$" disclosed as SEQ ID NO: 16). Group B is Anti-Rha+Pam$_3$CysSK$_4$-MUC1-Tn ("CysSK4" disclosed as SEQ ID NO: 16). Group C is pass through+Rha-Pam$_3$CysSK$_4$-MUC1-Tn ("CysSK$_4$" disclosed as SEQ ID NO: 16). Group D is pass through+Pam$_3$CysSK$_4$-MUC1-Tn ("CysSK$_4$" disclosed as SEQ ID NO: 16).
Figure 27B:
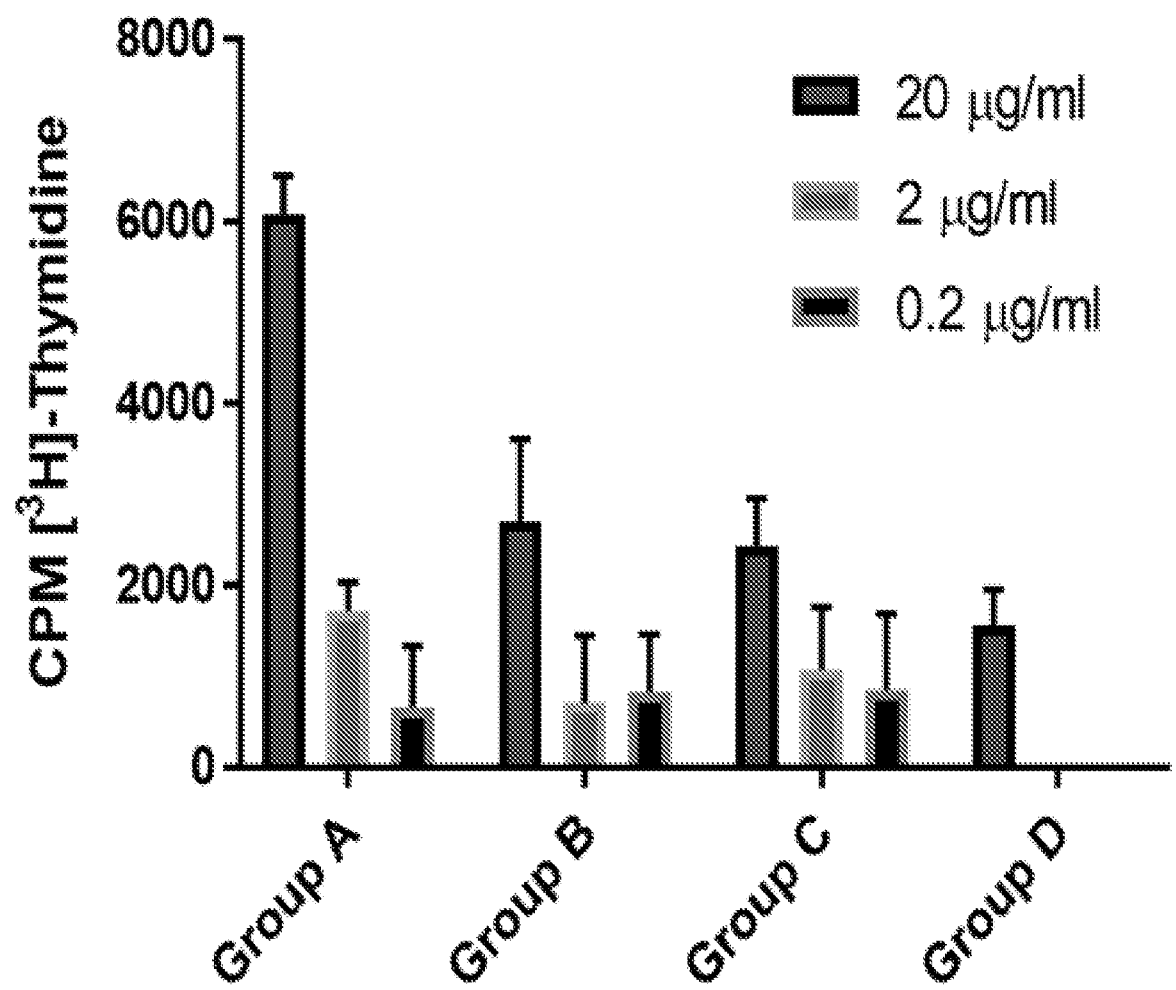
Figure 27C:
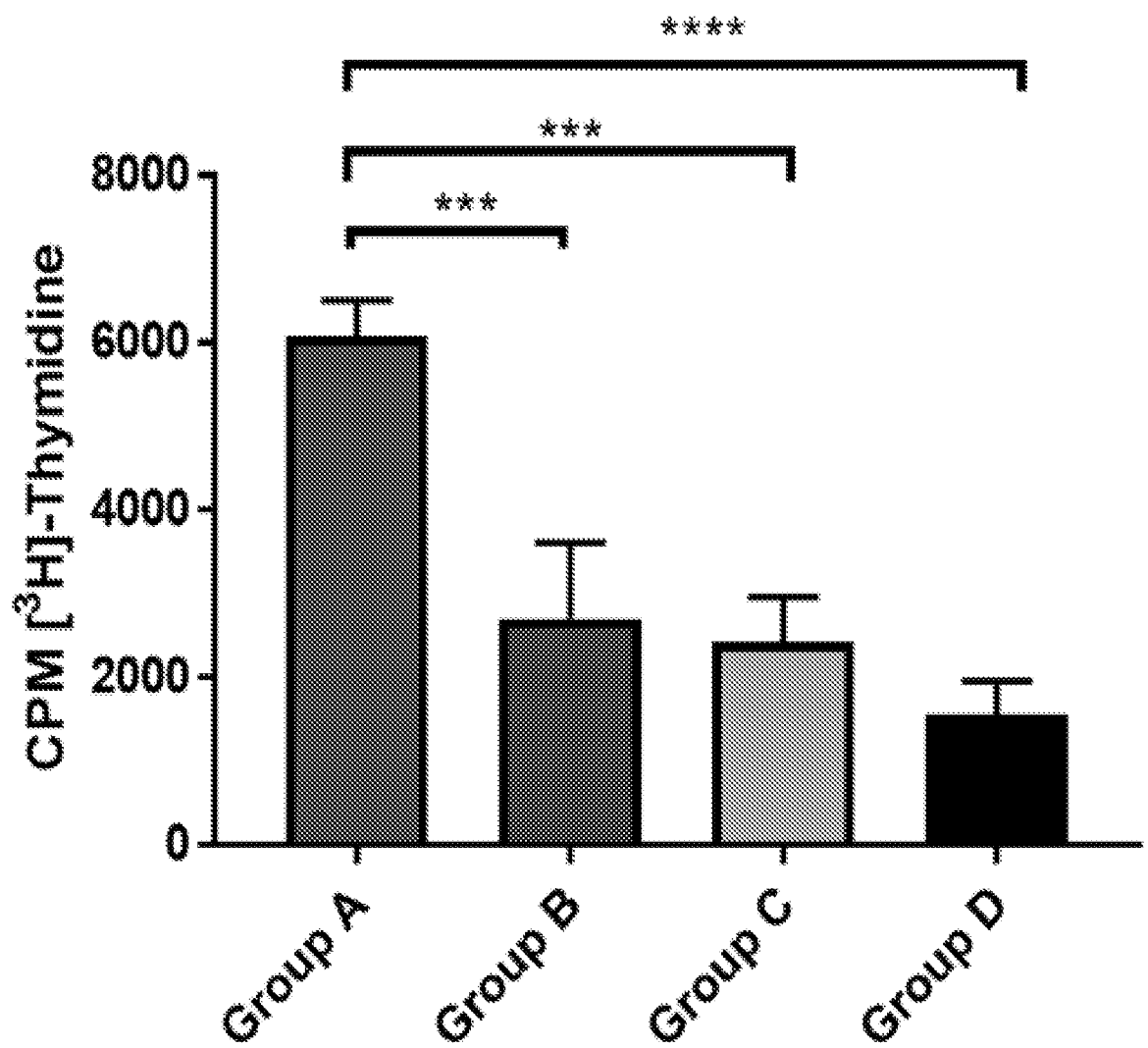

FIGS. 27A-27C show in-vivo enhancement of anti-MUC1-Tn response by human anti-rhamnose antibodies. Mice were injected with anti-Rha or pass through (no anti-Rha) antibody and one hour later received MUC1-Tn antigen vaccine with or without Rhamnose. Group A is Anti-Rha+Rha-Pam$_3$CysSK4-MUC1-Tn ("CysSK$_4$" disclosed as SEQ ID NO: 16). Group B is Anti-Rha+ Pam$_3$CysSk4-MUC1-Tn ("CysSK$_4$" disclosed as SEQ ID NO: 16). Group C is pass through+Rha=Pam$_3$CysSK4-MUC1-Tn ("CysSK$_4$" disclosed as SEQ ID NO: 16). Group D is pass through+Pam$_3$CysSK4-MUC1-Tn ("CysSK$_4$" disclosed as SEQ ID NO: 16). (FIG. 27A.) Sera were collected seven days after the second boost and MUC1-Tn antibody production was measured by ELISA on MUC1-Tn coated plates. FIG. 27B shows concentration dependent and MUC1-Tn-specific CD4+ T cell proliferative response of the four different groups. (FIG. 27C.) Data from FIG. 27B is plotted at 20 μg/ml MUC1-Tn. Control group and MUC1 non-specific proliferation were subtracted.

Figure 28A:
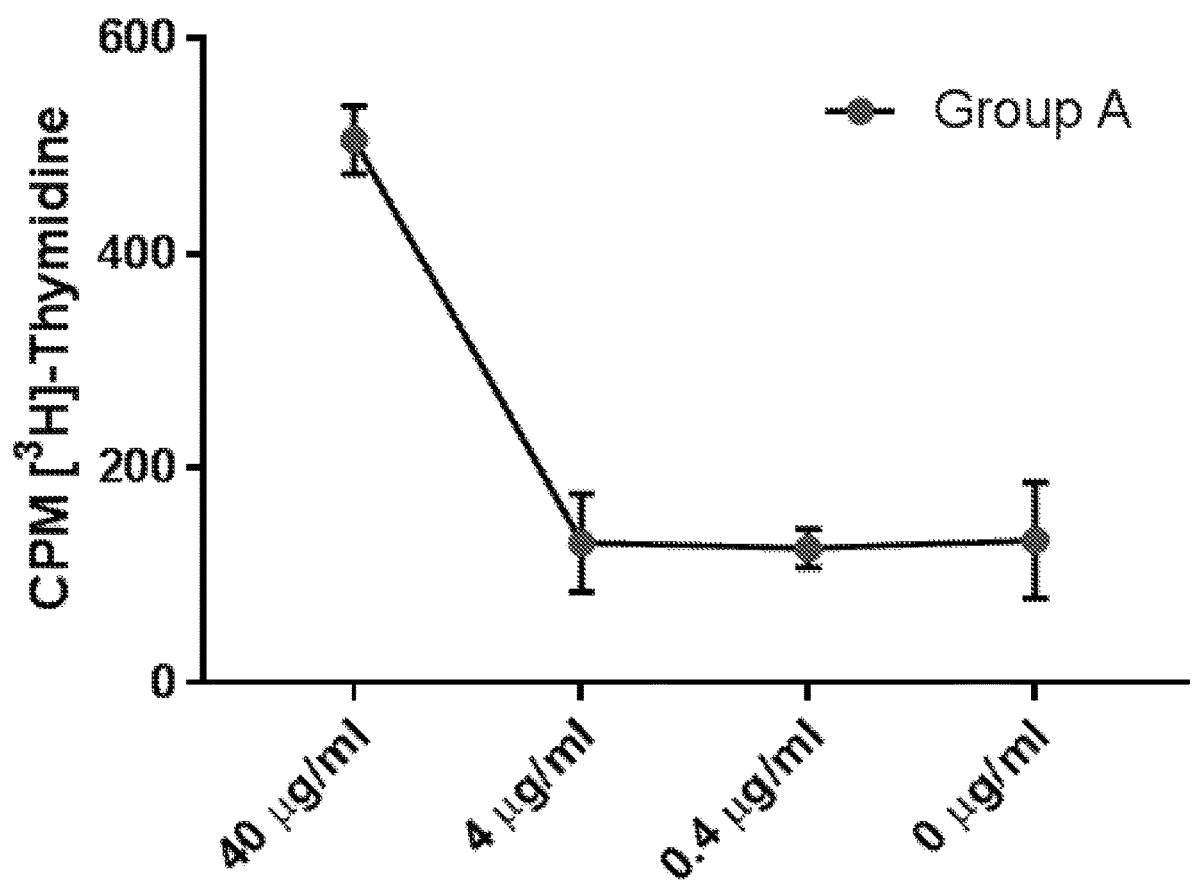
FIGS. 28A-28D show the effect of human anti-rhamnose antibodies on CD8+ T cell responses to MUC1-Tn vaccine. Group A is Anti-Rha+Rha-Pam$_3$CysSK$_4$-MUC1-Tn ("CysSK$_4$" disclosed as SEQ ID NO: 16). Group B is Anti-Rha+Pam$_3$CysSK$_4$-MUC1-Tn ("CysSK$_4$" disclosed as SEQ ID NO: 16). Group C is pass through+Rha=Pam$_3$CysSK$_4$-MUC1-Tn ("CysSK$_4$" disclosed as SEQ ID NO: 16). Group D is pass through+Pam$_3$CysSK$_4$-MUC1-Tn ("CysSK$_4$" disclosed as SEQ ID NO: 16).
Figure 28B:
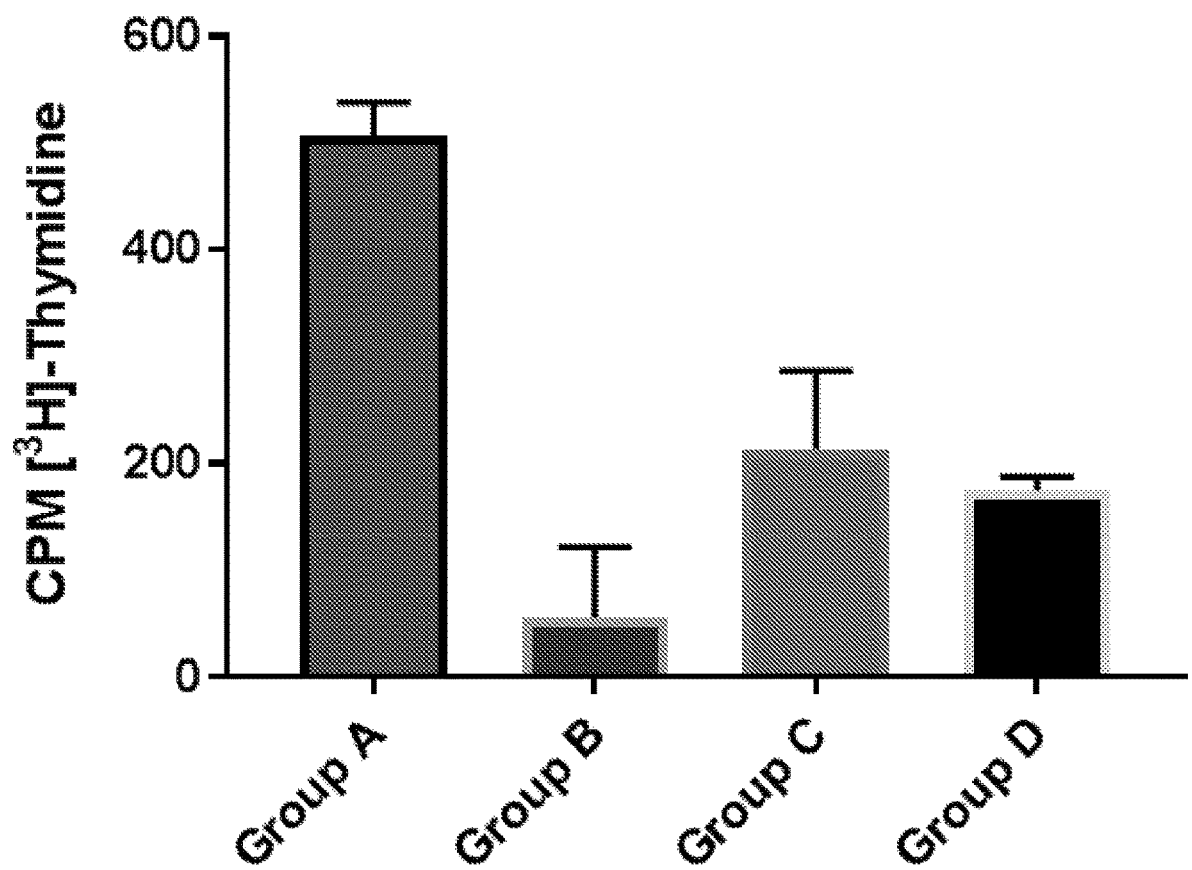
Figure 28C:
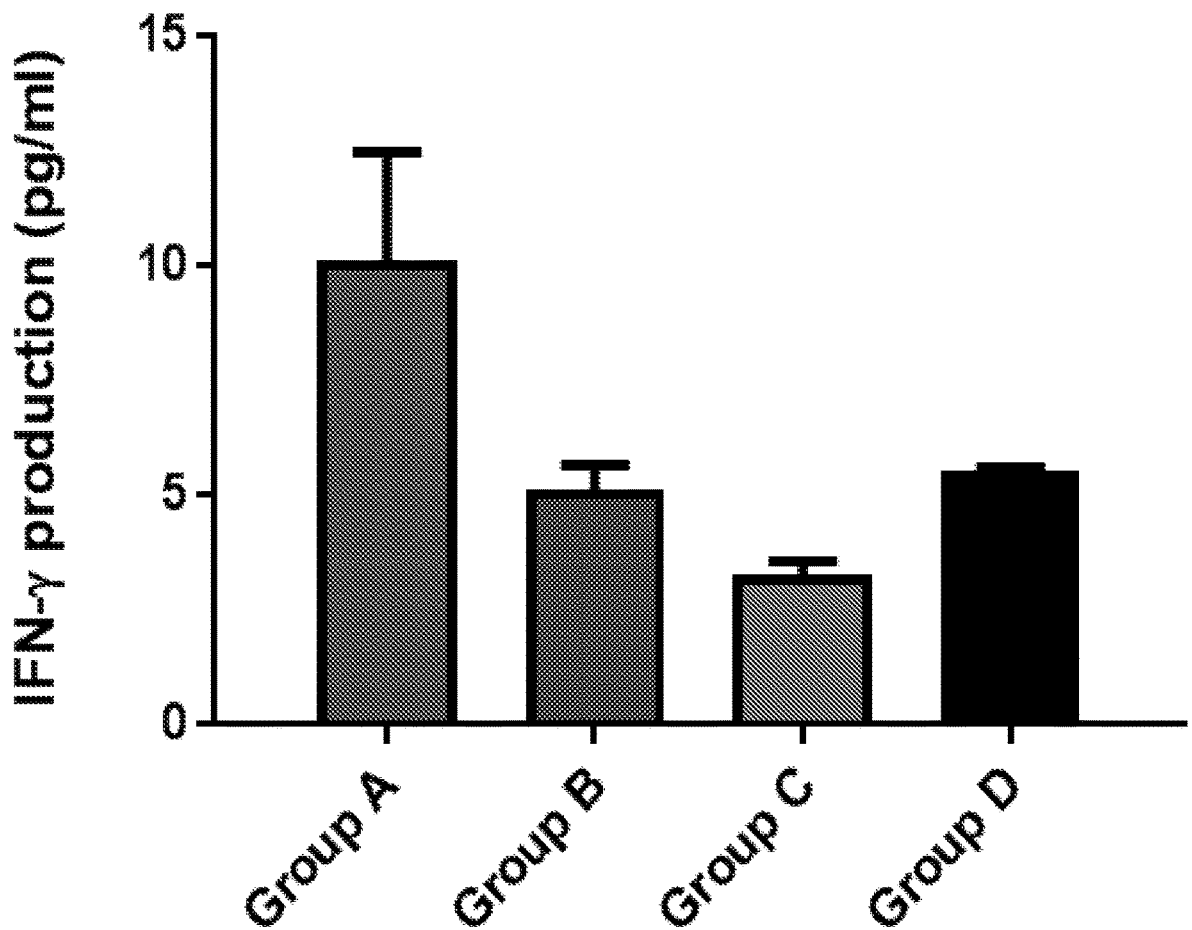
Figure 28D:
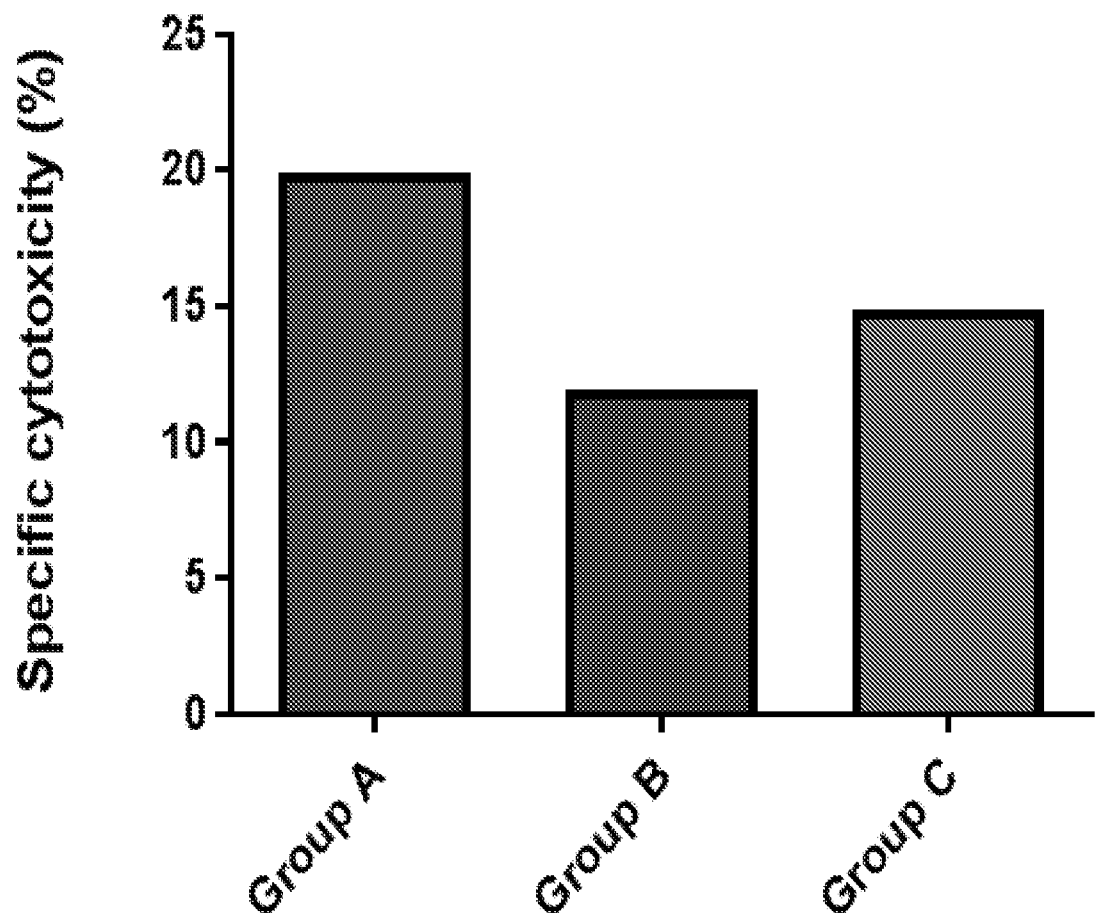

FIGS. 28A-28D show the effect of human anti-rhamnose antibodies on CD8+ T cell responses to MUC1-Tn vaccine. FIG. 28A shows concentration dependent in vitro CD8+ T cell proliferative response of group A with varying amounts of MUC1-Tn antigen. FIG. 28B shows MUC1-Tn-specific CD8+ T cell proliferative response of the four different groups (40 μg/ml MUC1-Tn). Control group and MUC1-non-specific proliferation were subtracted. FIG. 28C shows CD8+ T cell specific IFN-Y production in four groups of mice at 40 μg/ml CD8 MUC1-Tn epitope peptide. FIG. 28D shows apoptosis of EL4 cells presenting the CD8 epitope peptide induced by CD8+ T cells of the different groups. The ratio of EL4 to CD8+ cells was 1:100.

Anti-Diabetic Effect When R$_2$ is a Pathogenic or Altered Diabetic Peptide Sequence Immune cells protect the human body from foreign antigens. However, in autoimmune diseases like type 1 diabetes (T1D), autoreactive T cells recognize pancreatic beta cell related proteins as antigens, leading to beta cell destruction. An altered peptide ligand (APL) strategy can be used to target autoreactive T cells in T1D. GAD 546-554 (SEQ ID NO: 7) is reported as a dominant epitope recognized by autoreactive T cells, in the non-obese diabetic mouse model, that can cause destruction of beta cells. Nine APLs which have single alanine substitution, at different positions of GAD 546-554 (SEQ ID NO: 7), were screened. When GAD 546-554 (SEQ ID NO: 7) specific CD8 T cell clone was incubated with different APLs and antigen presenting cells, APL9 (SEQ ID NO: 8) inhibited both IFN-γ and TNF-α release. In order to improve antigen presentation and endosomal escape of APL9 (SEQ ID NO: 8), a bioconjugate platform of a liposome containing a Formula I bioconjugate of APL9 (SEQ ID NO: 8) and the toll like receptor ligand, Pam$_3$CysSK$_4$ ("CysSK$_4$" disclosed as SEQ ID NO: 16), as well as antibody against macrophage and dendritic cell protein, F4/80, was developed. This immunotherapy strategy is beneficial to prevent T1D by rendering autoreactive immune cells more tolerant of beta cells. By altering the peptide to change a lysine to an alanine, T cell activity may be blocked such that T cells cannot respond to the pathogenic peptide.

GAD 546-554 (SEQ ID NO: 7) specific CD8 T cell clone (CTL.546L) was used in order to study the efficiency of GAD 546-554 (SEQ ID NO: 7) bioconjugate. This CD8T cell clone recognizes the GAD 546-554 peptide (SEQ ID NO: 7) presented by MHC class I molecules on the antigen presenting cells (APC). M12C3B7, B cell line, was used as an APC. APCs ($0.5 \times 10^5$ cells/well) were treated with bioconjugate GAD 546-554 (SEQ ID NO: 7) for 3 hours. Later, these cells were co-cultured with CTL.546.L ($2 \times 10^5$ cells/well) for 24 hours. After 24 hours of incubation, supernatants were collected for studying the interferon gamma release.

Figure 29:
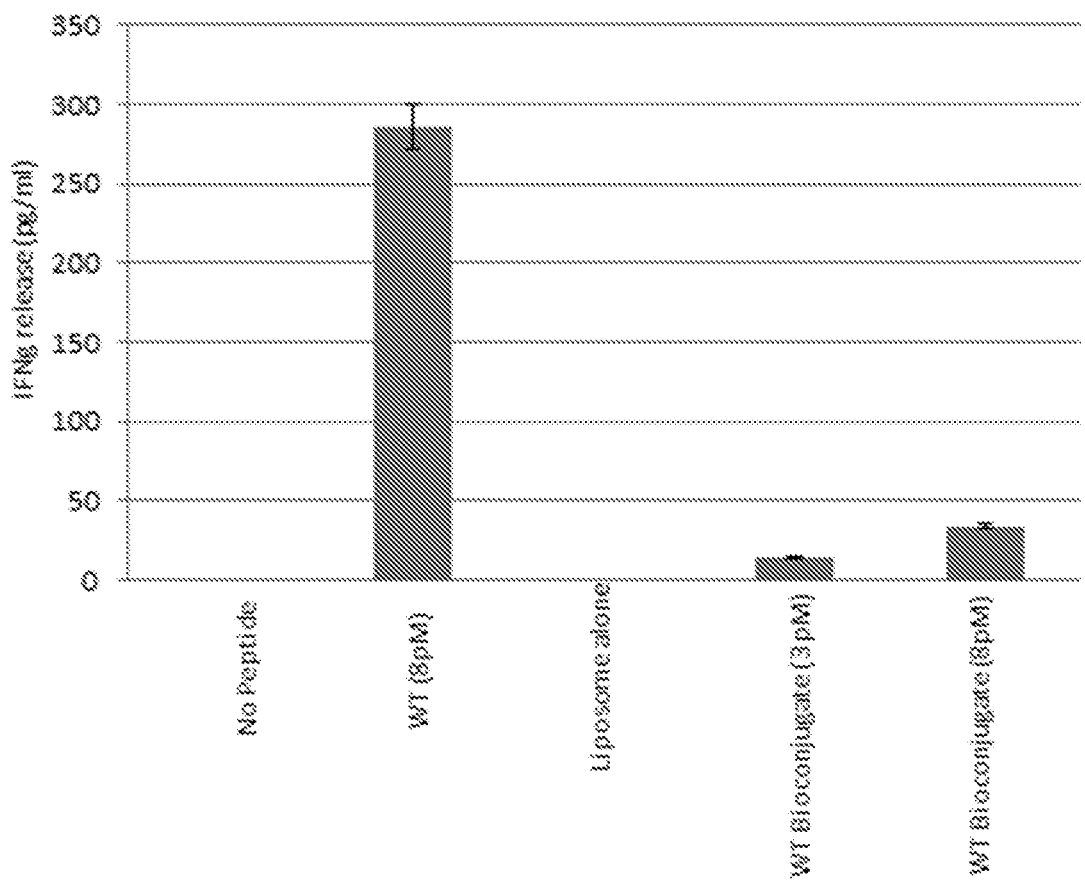
FIG. 29: Effect of GAD 546-554 (WT) peptide (SEQ ID NO: 7) and GAD 546-554 (SEQ ID NO: 7) bioconjugate on GAD 546-554 (SEQ ID NO: 7) specific CD8T cells using M12C3.B7 as APCs.

IFNγ release was significantly lower with bioconjugate 546-554 (SEQ ID NO: 7) than free peptide, GAD 546-544 (SEQ ID NO: 7). (FIG. 29.) This may be due to the particular bioconjugate being too short to get processed and presented on MHC I molecule as it is. Therefore, a bioconjugate of GAD 541-554 (SEQ ID NO: 6) with F/80 antibody was designed in order to improve the presentation and processing of bioconjugate by APCs. The same assay for studying the effect of bioconjugate GAD 541-554 (SEQ ID NO: 6) was used. M12C3.B7 cells ($0.5 \times 10^5$ per well) were incubated with bioconjugate GAD 541-554 (SEQ ID NO: 6) for three hours. GAD 546-554 (SEQ ID NO: 7) specific CD8T cells ($0.5 \times 10^5$ per well) were added in the pretreated M12C3.B7 cells. Co-culture was incubated for 24 hours at 37° C. Supernatants were used to study the IFNγ release.

Figure 30:
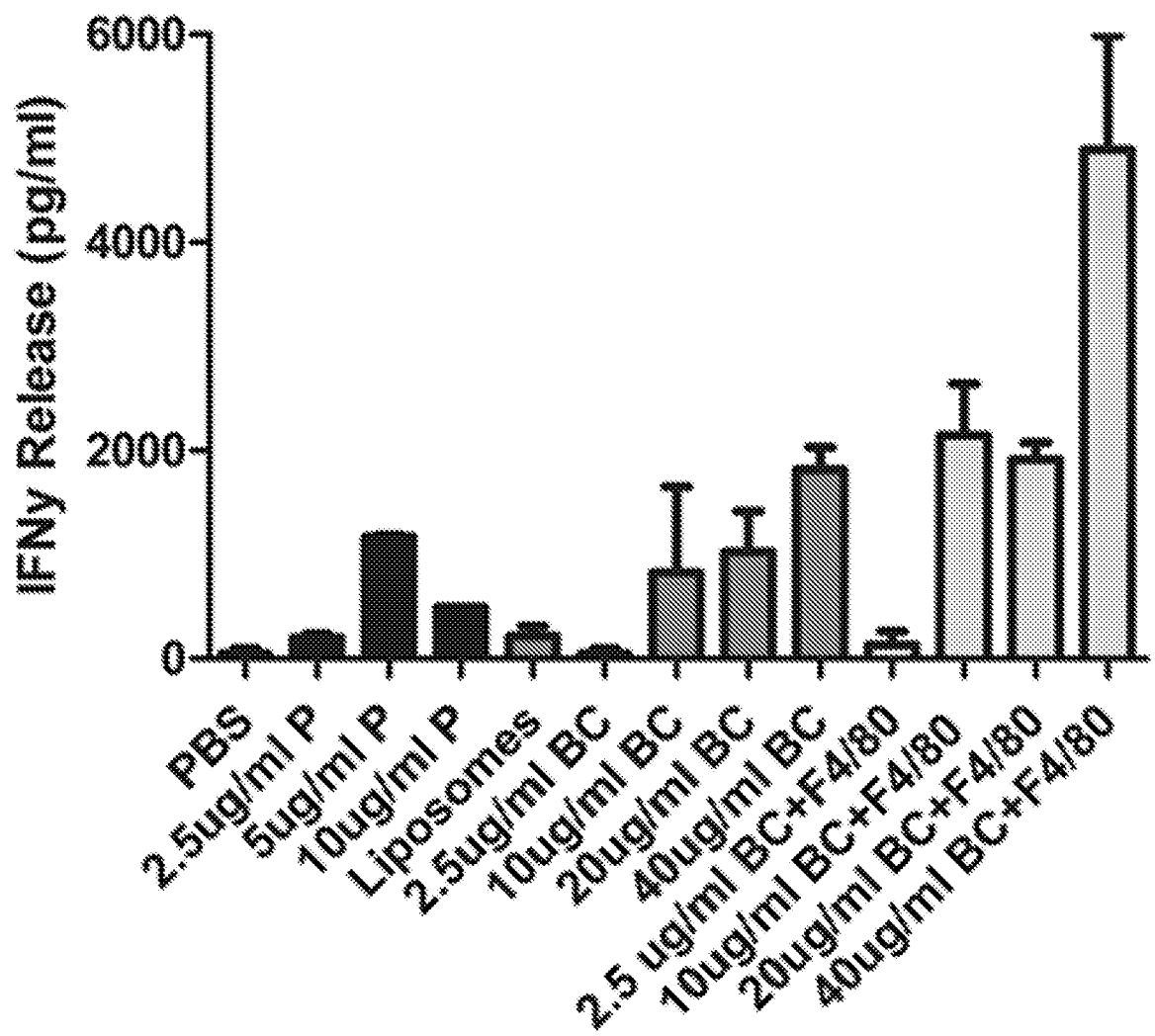
FIG. 30: Effect of GAD 546-554 (WT) peptide (SEQ ID NO: 7) and GAD 541-554 (SEQ ID NO: 6) bioconjugate on GAD 546-554 (SEQ ID NO: 7) specific CD8T cells using M12C3.B7 as APCs.

A significant increase in IFNγ released by GAD 546-554 (SEQ ID NO: 7) specific CD8 T cells clone was observed on stimulation with GAD 541-554 (SEQ ID NO: 6) bioconjugate with F4/80 antibody as compared to peptide alone. (FIG. 30.) Further, this system was studied in non-diabetic non-obese diabetic model (NOD). Six weeks old NOD female mice (n=3) were treated with PBS, bioconjugate GAD 541-554 (SEQ ID NO: 6), or bioconjugate GAD 541-554 (SEQ ID NO: 6) with F4/80 antibody, for three consecutive weeks. These mice were sacrificed and their spleens were collected for performing T stimulation assay using IFNγ secreting ELISPOT kit. Splenocytes ($1 \times 10^6$ cells/well) were treated with PBS or bioconjugate GAD 541-554 (SEQ ID NO: 6) or bioconjugate GAD 541-554 (SEQ ID NO: 6) with F4/80 antibody for 36 hours. After 36 hours of incubation, IFNγ secreting cells were looked for.

Figure 31:
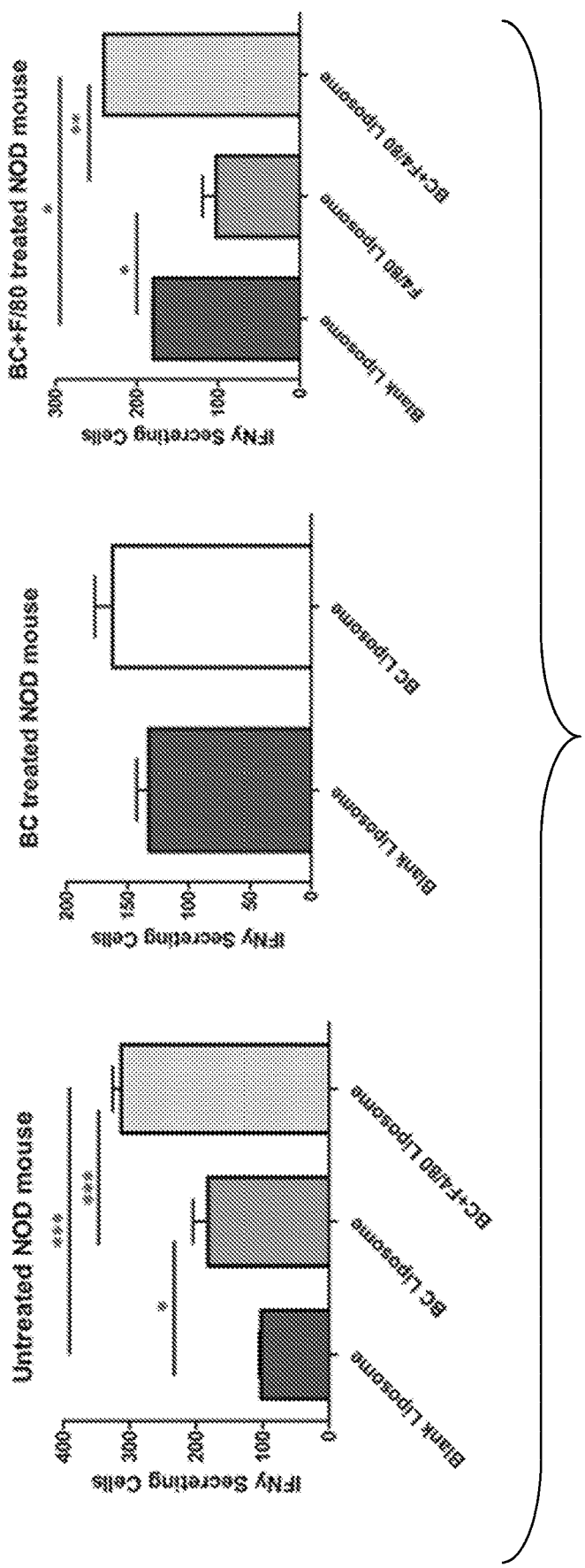
FIG. 31: Effect of GAD 546-554 peptide (SEQ ID NO: 7) and GAD 541-554 (SEQ ID NO: 6) bioconjugate on GAD 546-554 (SEQ ID NO: 7) specific CD8T cells using M12C3.B7 as APCs.

Splenocytes from vehicle treated mice showed an increase in number of IFNγ secreting cells after treatment with bioconjugate. (FIG. 31.) This indicates that the bioconjugate is getting processed and presented by APCs and NOD mice have T cells that are specific for GAD 541-554 (SEQ ID NO: 6). Further, animals primed with either bioconjugate or bioconjugate with F4/80 also showed an increase in number of IFNγ secreting cells after treating them with either bioconjugate or bioconjugate with F4/80.

This example indicates that compositions of Formula I such as the adjuvant altered diabetic peptide conjugate (15), which includes SEQ ID NO: 9, having a single alanine substitution from GAD 541-554 (SEQ ID NO: 6), may be useful as anti-diabetic vaccines.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising Formula I:

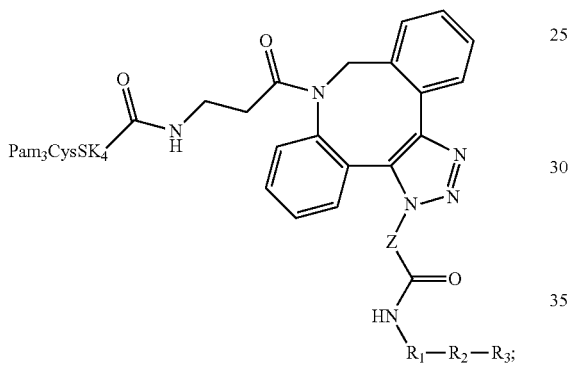

Formula I wherein:
the dashed line indicates $R_3$ is optional;
Z is —$(CH_2)_5$ or —$(CH_2)_2$;
$R_1$ is a heterologous helper T-cell epitope consisting of a sequence of from 7 to 30 amino acids, or a bond;
$R_2$ is a B or T cell epitope consisting of from 7 to 30 amino acids, optionally a TACA incorporated into the peptide sequence; and
$R_3$, when present, is an O-linked xenoantigen attached to an amino acid either via an alpha or beta linkage;
provided, however, that $R_1$ and $R_2$ can together be a single epitope selected from (i) a B cell epitope in the form of a carbohydrate antigen derived from bacterial cells, viral envelopes, or other infected cell lines; and (ii) a B or T cell epitope consisting of from 7 to 30 amino acids, optionally including a TACA incorporated into the peptide sequence;
and salts, stereoisomers, racemates, hydrates, and solvates thereof.

2. The composition of claim 1, wherein the composition is formulated in liposomes.

3. The composition of claim 2, wherein the liposomes comprise 1,2-dipalmitoyl-sn-glycero-3-phosphocholine (DPPC), cholesterol, and 1,2-distearoyl-sn-glycero-3-phosphoethanolamine-N-[maleimide(polyethylene glycol)-2000] (DSPE-PEG-MAL).

4. The composition of claim 2, wherein the liposomes comprise cholesterol-TEG-Rha, cholesterol, and 1,2-dipalmitoyl-sn-glycero-3-phosphocholine (DPPC).

5. The composition of claim 2, wherein the liposomes are conjugated to an antibody.

6. The composition of claim 5, wherein the antibody comprises anti-mouse F4/80.

7. The composition of claim 1, wherein the T-cell epitope is selected from the group consisting of: QYIKANSKFIGI-TEL (SEQ ID NO: 1); KLFAVWKITYKDTG (SEQ ID NO: 2); YAFKYARHANVGRNAFELFL (SEQ ID NO: 3); ISQAVHAAHAEINEAGR (SEQ ID NO: 4); and A' KZVAAWTLKAA' (SEQ ID NO: 5), wherein A' is D-alanine, and Z is L-cyclohexylalanine.

8. The composition of claim 1, wherein $R_2$ comprises an antigen-amino acid construct selected from the group consisting of:

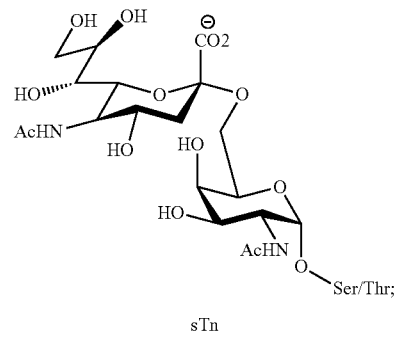

sTn

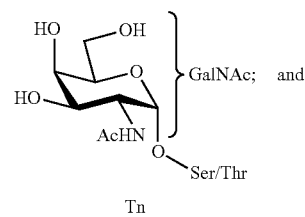

Tn

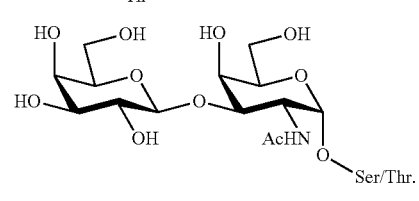

TF(T)

9. The composition of claim 1, wherein $R_1$ and $R_2$ are together an epitope comprising a tumor glycopeptide sequence having an incorporated TACA, selected from the group consisting of:

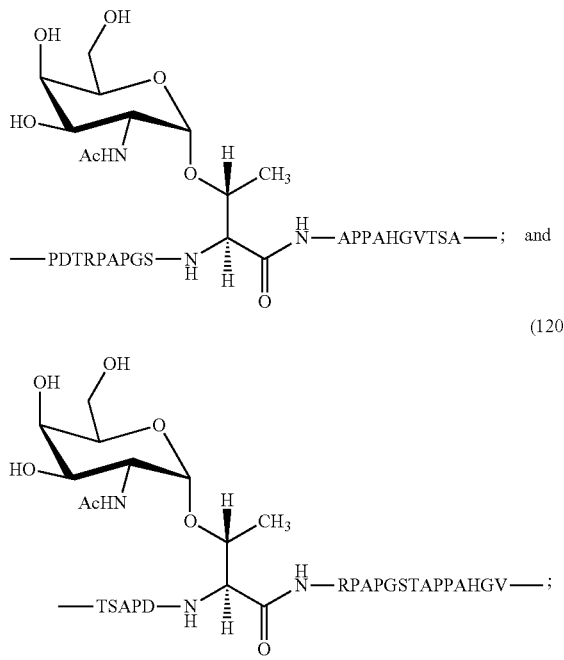

and wherein no $R_3$ group is present.

10. The composition of claim 1, wherein $R_1$ and $R_2$ together are a T-cell epitope comprising a pathogenic or altered diabetic peptide sequence selected from the group consisting of: GTTMVSYQPLGDKV (SEQ ID NO: 6), SYQPLGDKV (SEQ ID NO: 7), SYQPLGDAV (SEQ ID NO: 8), GTTMVSYQPLGDAV (SEQ ID NO: 9), SYQPLGDKA (SEQ ID NO: 10), and GTTMVSYQPLGDKA (SEQ ID NO: 11).

11. The composition of claim 9, wherein $R_3$ comprises a xenoantigen attached to either serine (S) or threonine (T).

12. The composition of claim 9, wherein $R_3$ comprises a xenoantigen-amino acid construct selected from the group consisting of:

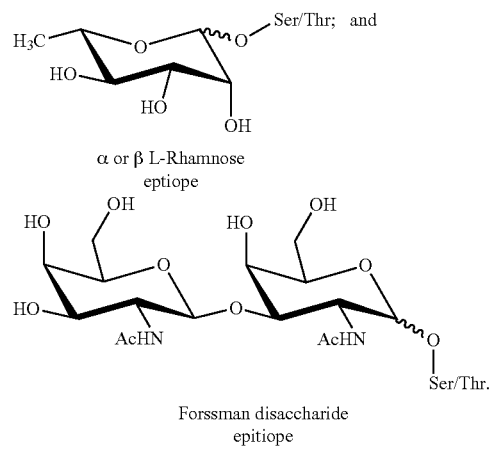

13. The composition of claim 9, wherein $R_3$ comprises a cluster of two or more Rhamnose epitopes.

14. The composition of claim 9, wherein $R_3$ comprises a cluster of three Rhamnose epitopes.

15. The composition of claim 1, wherein the composition comprises glycopeptide (11):

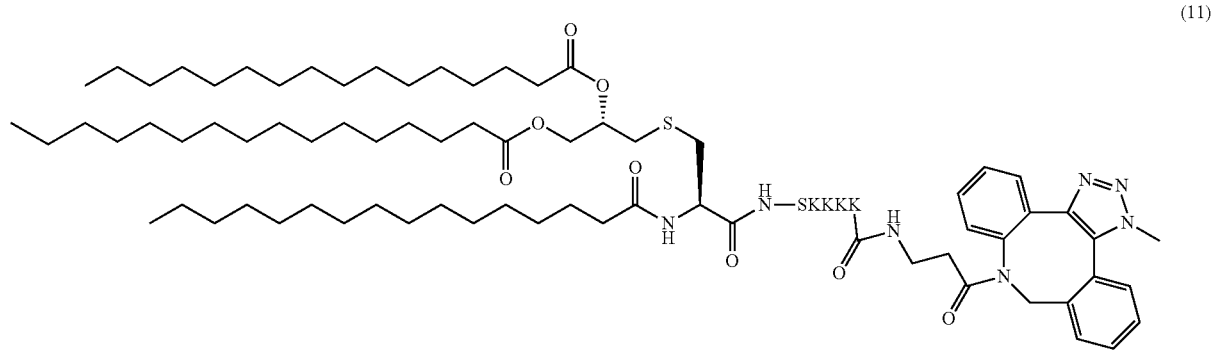

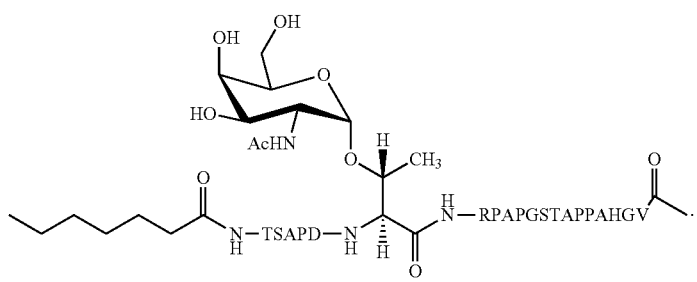

16. The composition of claim 1, wherein the composition comprises adjuvant pathogenic diabetic peptide conjugate (13):
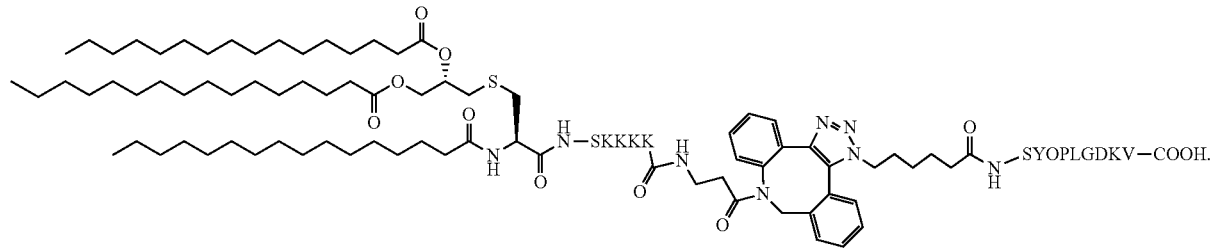
(13)
17. The composition of claim 1, wherein the composition comprises adjuvant altered diabetic peptide conjugate (15):
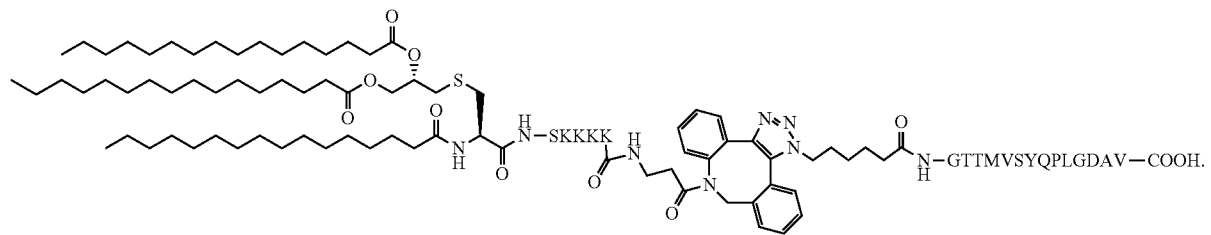
(15)
18. The composition of claim 1, wherein the composition comprises MUC1 lipoglycopeptide (22):

(22)
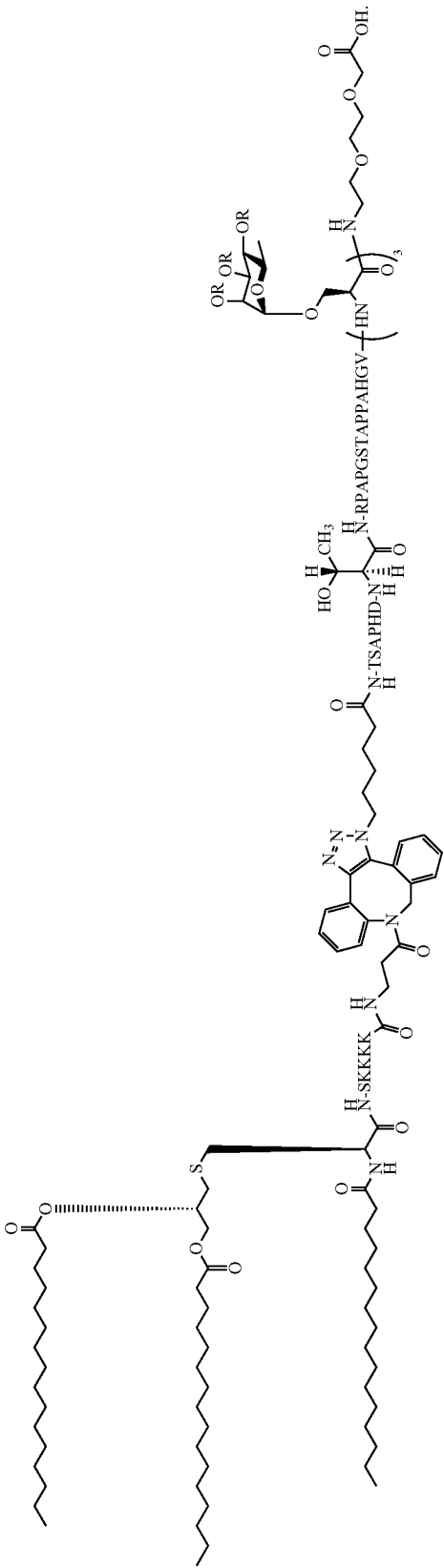

19. The composition of claim 1, wherein the composition comprises pathogenic peptide (30):
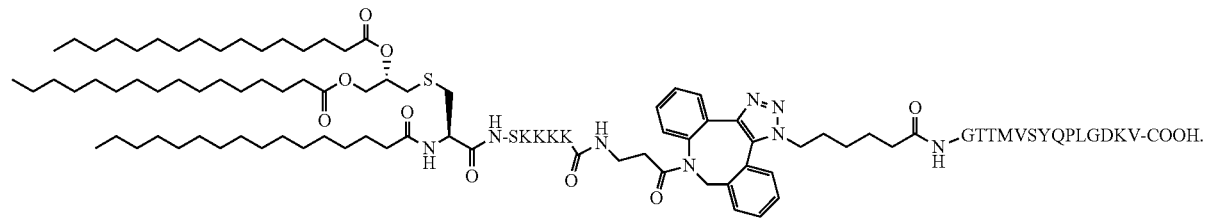
(30)
20. A vaccine composition comprising:
a therapeutically effective amount of a composition of claim 1; and
a pharmaceutically acceptable carrier, excipient, or diluent.
* * * * *

SEQUENCE LISTING

```
<160> NUMBER OF SEQ ID NOS: 20

<210> SEQ ID NO 1
<211> LENGTH: 15
<212> TYPE: PRT
<213> ORGANISM: Unknown
<220> FEATURE:
<223> OTHER INFORMATION: Description of Unknown:
      Tetanus toxoid epitope

<400> SEQUENCE: 1

Gln Tyr Ile Lys Ala Asn Ser Lys Phe Ile Gly Ile Thr Glu Leu
1               5                   10                  15

<210> SEQ ID NO 2
<211> LENGTH: 14
<212> TYPE: PRT
<213> ORGANISM: Neisseria meningitidis

<400> SEQUENCE: 2

Lys Leu Phe Ala Val Trp Lys Ile Thr Tyr Lys Asp Thr Gly
1               5                   10

<210> SEQ ID NO 3
<211> LENGTH: 20
<212> TYPE: PRT
<213> ORGANISM: Neisseria meningitidis

<400> SEQUENCE: 3

Tyr Ala Phe Lys Tyr Ala Arg His Ala Asn Val Gly Arg Asn Ala Phe
1               5                   10                  15

Glu Leu Phe Leu
            20

<210> SEQ ID NO 4
<211> LENGTH: 17
<212> TYPE: PRT
<213> ORGANISM: Unknown
<220> FEATURE:
<223> OTHER INFORMATION: Description of Unknown:
      Epitope derived from ovalbumin

<400> SEQUENCE: 4

Ile Ser Gln Ala Val His Ala Ala His Ala Glu Ile Asn Glu Ala Gly
1               5                   10                  15

Arg

<210> SEQ ID NO 5
<211> LENGTH: 12
<212> TYPE: PRT
<213> ORGANISM: Unknown
<220> FEATURE:
<223> OTHER INFORMATION: Description of Unknown:
      Pan DR epitope
<220> FEATURE:
```

```
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (3)..(3)
<223> OTHER INFORMATION: L-cyclohexylalanine
<220> FEATURE:
<221> NAME/KEY: MOD_RES
<222> LOCATION: (12)..(12)
<223> OTHER INFORMATION: D-Ala

<400> SEQUENCE: 5

Ala Lys Xaa Val Ala Ala Trp Thr Leu Lys Ala Ala
1               5                   10

<210> SEQ ID NO 6
<211> LENGTH: 14
<212> TYPE: PRT
<213> ORGANISM: Unknown
<220> FEATURE:
<223> OTHER INFORMATION: Description of Unknown:
      Diabetic peptide sequence

<400> SEQUENCE: 6

Gly Thr Thr Met Val Ser Tyr Gln Pro Leu Gly Asp Lys Val
1               5                   10

<210> SEQ ID NO 7
<211> LENGTH: 9
<212> TYPE: PRT
<213> ORGANISM: Unknown
<220> FEATURE:
<223> OTHER INFORMATION: Description of Unknown:
      Diabetic peptide sequence

<400> SEQUENCE: 7

Ser Tyr Gln Pro Leu Gly Asp Lys Val
1               5

<210> SEQ ID NO 8
<211> LENGTH: 9
<212> TYPE: PRT
<213> ORGANISM: Unknown
<220> FEATURE:
<223> OTHER INFORMATION: Description of Unknown:
      Diabetic peptide sequence

<400> SEQUENCE: 8

Ser Tyr Gln Pro Leu Gly Asp Ala Val
1               5

<210> SEQ ID NO 9
<211> LENGTH: 14
<212> TYPE: PRT
<213> ORGANISM: Unknown
<220> FEATURE:
<223> OTHER INFORMATION: Description of Unknown:
      Diabetic peptide sequence

<400> SEQUENCE: 9

Gly Thr Thr Met Val Ser Tyr Gln Pro Leu Gly Asp Ala Val
1               5                   10

<210> SEQ ID NO 10
<211> LENGTH: 9
<212> TYPE: PRT
<213> ORGANISM: Unknown
<220> FEATURE:
```

-continued

```
<223> OTHER INFORMATION: Description of Unknown:
      Diabetic peptide sequence

<400> SEQUENCE: 10

Ser Tyr Gln Pro Leu Gly Asp Lys Ala
1               5

<210> SEQ ID NO 11
<211> LENGTH: 14
<212> TYPE: PRT
<213> ORGANISM: Unknown
<220> FEATURE:
<223> OTHER INFORMATION: Description of Unknown:
      Diabetic peptide sequence

<400> SEQUENCE: 11

Gly Thr Thr Met Val Ser Tyr Gln Pro Leu Gly Asp Lys Ala
1               5                   10

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Asp Thr Arg Pro Ala Pro Gly Ser Thr Ala Pro Pro Ala His Gly
1               5                   10                  15

Val Thr Ser Ala
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Ser Ala Pro Asp Thr Arg Pro Ala Pro Gly Ser Thr Ala Pro Pro
1               5                   10                  15

Ala His Gly Val
            20

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Lys Lys Lys Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Pro Asp Thr Arg Pro
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Ser Lys Lys Lys Lys
1               5

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-azido hexanoic acid

<400> SEQUENCE: 17

Xaa Thr Ser Ala Pro Asp Thr Arg Pro Ala Pro Gly Ser Thr Ala Pro
1               5                   10                  15

Pro Ala His Gly Val
            20

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-azido hexanoic acid

<400> SEQUENCE: 18

Xaa Ser Tyr Gln Pro Leu Gly Asp Lys Val
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-azido hexanoic acid

<400> SEQUENCE: 19

Xaa Gly Thr Thr Met Val Ser Tyr Gln Pro Leu Gly Asp Ala Val
1               5                   10                  15

<210> SEQ ID NO 20
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-azido hexanoic acid

<400> SEQUENCE: 20

Xaa Thr Ser Ala Pro His Asp Thr Arg Pro Ala Pro Gly Ser Thr Ala
1               5                   10                  15

Pro Pro Ala His Gly Val
            20
```